United States Patent
Kemble et al.

(10) Patent No.: US 7,550,149 B2
(45) Date of Patent: Jun. 23, 2009

(54) ATTENUATION OF CYTOMEGALOVIRUS VIRULENCE

(75) Inventors: George Kemble, Saratoga, CA (US); Gregory M. Duke, Redwood City, CA (US); Richard Spaete, Emerald Hills, CA (US)

(73) Assignee: MedImmune, LLC, Gaitherburg, MD (US)

( * ) Notice: Subject to any disclaimer, the term of this patent is extended or adjusted under 35 U.S.C. 154(b) by 28 days.

(21) Appl. No.: 11/614,141

(22) Filed: Dec. 21, 2006

(65) Prior Publication Data

US 2007/0292455 A1    Dec. 20, 2007

Related U.S. Application Data

(62) Division of application No. 09/724,935, filed on Nov. 28, 2000, now Pat. No. 7,204,990.

(51) Int. Cl.
*A61K 39/12* (2006.01)
*A61K 39/245* (2006.01)
*C12Q 1/70* (2006.01)

(52) U.S. Cl. .............. 424/204.1; 424/205.1; 424/230.1; 435/5

(58) Field of Classification Search .............. None
See application file for complete search history.

(56) References Cited

U.S. PATENT DOCUMENTS

| 5,721,354 A | 2/1998 | Spaete et al. |
| 2008/0019945 A1 | 1/2008 | Kemble |

OTHER PUBLICATIONS

Beisel, 2000, "Cytomegalovirus Vaccine Development," Jordan Reprt, 105-110.
Cha et al., Human Cytomegalovirus Clinical Isolates carry at Least 19 Genes Not Found In Laboratory Strans, 1996, J Virol 70:78-83.
Chee et al., Analysis of the Protein-Coding of the Sequence of Human Cytomegalovirus Strain AD169, 1990, Curr Top Microbiol Immunol. 154, 125-169.
Cihlar et al., Characterization of Drug Resistance-Associated Mutations in the Human Cytomegalovirus DNA Polymerase Gene by Using Recombiant . . . 1998, J Virol 72:5927-36.
Haberland et al., Variation Within the Glycoprotein B Gene of Human Cytomegalovirus is Due to Homologous Recombination, 1999, J Gen Virol 80:1495-1500.
Kemble et al., 1996, "A New Generation of Live, Attenuated Cytomegalovirus (CMV) Vaccine Strains," Interscience Conf. Antimicrob. Agents and Chem, H88.
Kemble et al., 1996, "Genetic Deteminanats of CMV Virulence," 21st Herpesvirus Workshop; 315.
Kemble et al., 1997, "Derivation of Novel, Recombinant, Live, Attenuated CMV Vaccine Strains," 6th Int. Cytomegalovirus Workshop, A-25(49).
Kemble et al., Jul. 1999, "Development of Live, Attenuated Human Cytomegalovirus Vaccine Candidates," 24th Inter. Herpesvirus Workshop; 13.007.
Kemble et al., Apr. 1999, "Towne/Toledo Vaccine Development," 7th Intl. Cytomegalovirus Workshop, Brighton, U.K.,.
Mocarski et al., A Delection Mutant in the Human Cytomegalovirus Gene Encoding IEI-491aa is Replication Defective Due to a Failure in Autoregulation, 1996, PNAS 93:11321-11326.
Pande et al., Cloning and Physical Mapping of a Gene Fragment Coding for a 64-kilodalton Major Late Antigen of Human Cytomegalovirus, 1984, PNAS 54:817-24.
Plotkin, Apr. 1999, "Vaccination Against Cytomegalovirus, The Changeling Demon," Pediatr Infect Dis J., 18:313-326.
Spaete et al., 1997, Progress in Developing a CMV Vaccine, Virology Seminar; Max-von-Pettenkofer Institute und Genz, Munchen,Germany;1-13.
Spaete et al., "Controlling CMV through Vaccination," Mar. 20-22, 1998, Science Symposium; Tucson AZ.
Spaete et al., 1998, "Progress in Developing a CMV Vaccine,"Virology Seminar; University of California—Irvine.
Spector et al., Cleavage Maps for Human Cytomegalovirus DNA Strain AD169 for Restriction Endonucleases EcoRI, BglII, and HindIII, 1982, J Virol 42:558-82.
U.S. Appl. No. 11/614,035, filed Dec. 20, 2006, Kemble.

*Primary Examiner*—Stacy B Chen

(57) ABSTRACT

A method is provided for attenuating a cytomegalovirus comprising functionally disrupting an open reading frame of a Toledo genome region or its homolog and making chimeric CMV virus genomes.

6 Claims, 36 Drawing Sheets

```
              10         20         30         40         50         60
        CGCTGTAGGG ATAAATAGTG CGATGGCGTT TGTGGGAGAA CGCAGTAGCG ATGGGTTGCG
        GCGACATCCC TATTTATCAC GCTACCGCAA ACACCCTCTT GCGTCATCGC TACCCAACGC
              100        80         90         100        110        120
        ACGTGCACGA TCCTTCGTGG CAATGCCAAT GGGGCGTTCC CACGATTATC GTGGCCTGGA
        TGCACGTGCT AGGAAGCACC GTTACGGTTA CCCCGCAAGG GTGCTAATAG CACCGGACCT
              130        140        150        160        170        180
        TAACATGCGC GGCTTTAGGA ATTTGGTGTT TGGCGGGATC GTCGGCGGAT GTCTCTTCGG
        ATTGTACGCG CCGAAATCCT TAAACCACAA ACCGCCCTAG CAGCCGCCTA CAGAGAAGCC
              190        200        210        220        230        240
        GACCCGGCAT CGCAGCCGTA GTCGGCTGTT CTGTTTTCAT GATTTTCCTC TGCGCGTATC
        CTGGGCCGTA GCGTCGGCAT CAGCCGACAA GACAAAAGTA CTAAAAGGAG ACGCGCATAG
              250        260        270        280        290        300
        TCATCCGTTA CCGGGAATTC TTCAAAGACT CCGTAATCGA CCTCCTTACC TGCCGATGGG
        AGTAGGCAAT GGCCCTTAAG AAGTTTCTGA GGCATTAGCT GGAGGAATGG ACGGCTACCC
              310        320        330        340        350        360
        TTCGCTACTG CAGCTGCAGC TGTAAGTGCA GCTGCAAATG CATCTCGGGC CCCTGTAGCC
        AAGCGATGAC GTCGACGTCG ACATTCACGT CGACGTTTAC GTAGAGCCCG GGGACATCGG
              370        380        390        400        410        420
        GCTGCTGTTC AGCGTGTTAC AAGGAGACGA TGATTTACGA CATGGTCCAA TACGGTCATC
        CGACGACAAG TCGCACAATG TTCCTCTGCT ACTAAATGCT GTACCAGGTT ATGCCAGTAG
              430        440        450        460        470        480
        GACGGCGTCC CGGACACGGC GACGATCCCG ACAGGGTGAT CTGCGAGATA GTCGAGAGTC
        CTGCCGCAGG GCCTGTGCCG CTGCTAGGGC TGTCCCACTA GACGCTCTAT CAGCTCTCAG
              490        500        510        520        530        540
        CCCCGGTTTC GGCGCCGACG GTGTCCGTCC CCCCGCCGTC GGAGGAGTCC CACCAGCCCG
        GGGGCCAAAG CCGCGGCTGC CACAGGCAGG GGGGCGGCAG CCTCCTCAGG GTGGTCGGGC
              550        560        570        580        590        600
        TCATCCCACC GCAGCCGCCA GCACCGACAT CGGAACCCAA ACCGAAGAAA GGTAGGGCGA
        AGTAGGGTGG CGTCGGCGGT CGTGGCTGTA GCCTTGGGTT TGGCTTCTTT CCATCCCGCT
              610        620        630        640        650        660
        AAGATAAACC GAAGGGTAGA CCGAAAGACA AACCTCCGTG CGAACCGACG GTGAGTTCAC
        TTCTATTTGG CTTCCCATCT GGCTTTCTGT TTGGAGGCAC GCTTGGCTGC CACTCAAGTG
              670        680        690        700        710        720
        AACCACCGTC GCAGCCGACG GCAATGCCCG GCGGTCCGCC CGACGCGCCT CCCCCCGCCA
        TTGGTGGCAG CGTCGGCTGC CGTTACGGGC CGCCAGGCGG GCTGCGCGGA GGGGGGCGGT
              730        740        750        760        770        780
        TGCCGCAGAT GCCACCCGGC GTGGCCGAGG CGGTACAAGC TGCCGTGCAG GCGGCCGTGG
        ACGGCGTCTA CGGTGGGCCG CACCGGCTCC GCCATGTTCG ACGGCACGTC CGCCGGCACC
              790        800        810        820        830        840
        CCGCGGCTCT ACAACAACAG CAGCAGCATC AGACCGGAAC GTAACCCGCC CCCGGTGCGA
        GGCGCCGAGA TGTTGTTGTC GTCGTCGTAG TCTGGCCTTG CATTGGGCGG GGGCCACGCT
              850        860        870        880        890        900
        TAAGGAATTT TCCGACTTGG CGCACATCTC CTTCCTCAAT GTTTGGACAA TAAACACATT
        ATTCCTTAAA AGGCTGAACC GCGTGTAGAG GAAGGAGTTA CAAACCTGTT ATTTGTGTAA
              910        920        930        940        950        960
        CCTTGCCAAA AAATGACGTT TCCAGAAATC CAAGGCATAA ATGTCCGTAC ACCGGCCCTT
        GGAACGGTTT TTTACTGCAA AGGTCTTTAG GTTCCGTATT TACAGGCATG TGGCCGGGAA
              970        980        990        1000       1010       1020
        CCCAACACGG AGTTTGAGAT TCCAAGCAGG AGAGAAGATC ATGGTGTGGA TATGGCTCGG
        GGGTTGTGCC TCAAACTCTA AGGTTCGTCC TCTCTTCTAG TACCACACCT ATACCGAGCC
```

Fig. 1A (SEQ ID NO: 1)

```
              1030       1040       1050       1060       1070       1080
         CATCGGGCTC CTCGGCGGTA CCGGACTGGC TTCCCTGGTC CTGGCCATTT CCTTATTTAC
         GTAGCCCGAG GAGCCGCCAT GGCCTGACCG AAGGGACCAG GACCGGTAAA GGAATAAATG 1090       1100       1110       1120       1130       1140
         CCAGCGCCGA GGCCGCAAGC GATCCGACGA GACTTCGTCG CGAGGCCGGC TCCCGGGTGC
         GGTCGCGGCT CCGGCGTTCG CTAGGCTGCT CTGAAGCAGC GCTCCGGCCG AGGGCCCACG 1150       1160       1170       1180       1190       1200
         TGCTTCTGAT AAGCGTGGTG CCTGCGCGTG CTGCTATCGA AATCCGAAAG AAGACGTCGT
         ACGAAGACTA TTCGCACCAC GGACGCGCAC GACGATAGCT TTAGGCTTTC TTCTGCAGCA 1210       1220       1230       1240       1250       1260
         CGAGCCGCTG GATCTGGAAC TGGGGCTCAT GCGGGTGGAC ACCCACCCGC CGACGCCGCA
         GCTCGGCGAC CTAGACCTTG ACCCCGAGTA CGCCCACCTG TGGGTGGGCG GCTGCGGCGT 1270       1280       1290       1300       1310       1320
         GGTGCCGCGG TGTACGTCGC TCTACATAGG AGAGGATGGT CTGCCGATAG ATAAACCCGA
         CCACGGCGCC ACATGCAGCG AGATGTATCC TCTCCTACCA GACGGCTATC TATTTGGGCT 1330       1340       1350       1360       1370       1380
         GTTTCCTCCG GCGCGGTTCG AGATCCCCGA CGTATCCACG CCGGGAACGC CGACCAGCAT
         CAAAGGAGGC CGCGCCAAGC TCTAGGGGCT GCATAGGTGC GGCCCTTGCG GCTGGTCGTA 1390       1400       1410       1420       1430       1440
         CGGCCGATCT CCGTCGCATT GCTCCTCGTC GAGCTCTTTG TCGTCCTCGA CCAGCGTCGA
         GCCGGCTAGA GGCAGCGTAA CGAGGAGCAG CTCGAGAAAC AGCAGGAGCT GGTCGCAGCT 1450       1460       1470       1480       1490       1500
         CACGGTGCTG TATCAGCCGC CGCCATCCTG GAAGCCACCT CCGCCGCCCG GGCGCAAGAA
         GTGCCACGAC ATAGTCGGCG GCGGTAGGAC CTTCGGTGGA GGCGGCGGGC CCGCGTTCTT 1510       1520       1530       1540       1550       1560
         GCGGCCGCCT ACGCCGCCGG TCCGGGCCCC CACCACGCGG CTGTCGTCGC ACAGACCCCC
         CGCCGGCGGA TGCGGCGGCC AGGCCCGGGG GTGGTGCGCC GACAGCAGCG TGTCTGGGGG 1570       1580       1590       1600       1610       1620
         GACGCCGATA CCCGCGCCGC GTAAGAACCT GAGCACGCCG CCCACCAAGA AAACGCCGCC
         CTGCGGCTAT GGGCGCGGCG CATTCTTGGA CTCGTGCGGC GGGTGGTTCT TTTGCGGCGG 1630       1640       1650       1660       1670       1680
         GCCCACGAAA CCCAAGCCGG TCGGCTGGAC ACCGCCGGTG ACACCCAGGC CCTTCCCGAA
         CGGGTGCTTT GGGTTCGGCC AGCCGACCTG TGGCGGCCAC TGTGGGTCCG GGAAGGGCTT 1690       1700       1710       1720       1730       1740
         AACGCCGACG CCACAAAAGC CGCCGCGGAA TCCGAGACTA CCGCGCACCG TCGGTCTGGA
         TTGCGGCTGC GGTGTTTTCG GCGGCGCCTT AGGCTCTGAT GGCGCGTGGC AGCCAGACCT 1750       1760       1770       1780       1790       1800
         GAATCTCTCG AAGGTGGGAC TCTCGTGTCC CTGTCCCCGA CCCCGCACGC CGACGGAGCC
         CTTAGAGAGC TTCCACCCTG AGAGCACAGG GACAGGGGCT GGGGCGTGCG GCTGCCTCGG 1810       1820       1830       1840       1850       1860
         GACCACGCTG CCTATCGTGT CGGTTTCCGA GCTAGCCCCG CCTCCTCGAT GGTCGGACAT
         CTGGTGCGAC GGATAGCACA GCCAAAGGCT CGATCGGGGC GGAGGAGCTA CCAGCCTGTA 1870       1880       1890       1900       1910       1920
         CGAGGAACTC TTGGAACAGG CGGTGCAGAG CGTCATGAAG GACGCCGAGT CGATGCAGAT
         GCTCCTTGAG AACCTTGTCC GCCACGTCTC GCAGTACTTC CTGCGGCTCA GCTACGTCTA 1930       1940       1950       1960       1970       1980
         GACCTGAGAC CGAAAGAGCG AGCGCGTCCG TTGTACAGTT GTATAGCAGC ACACGCCTTC
         CTGGACTCTG GCTTTCTCGC TCGCGCAGGC AACATGTCAA CATATCGTCG TGTGCGGAAG 1990       2000       2010       2020       2030       2040
         CCTCTTTTTC ACCGCAGCTA AGAGAGAGAA AGAGAGTATG TCAGTCAAGG GCGTGGAGAT
         GGAGAAAAAG TGGCGTCGAT TCTCTCTCTT TCTCTCATAC AGTCAGTTCC CGCACCTCTA
```

Fig. 1B (SEQ ID NO: 1)

```
            2050        2060        2070        2080        2090        2100
        GCCAGAAATG  ACGTGGGACT  TGGACGTTAG  AAATAAATGG  CGGCGTCGAA  AGGCCCTGAG
        CGGTCTTTAC  TGCACCCTGA  ACCTGCAATC  TTTATTTACC  GCCGCAGCTT  TCCGGGACTC 2110        2120        2130        2140        2150        2160
        TCGCATTCAC  CGGTTCTGGG  AATGTCGGCT  ACGGGTGTGG  TGGCTGAGTG  ACGCCGGCGT
        AGCGTAAGTG  GCCAAGACCC  TTACAGCCGA  TGCCCACACC  ACCGACTCAC  TGCGGCCGCA 2170        2180        2190        2200        2210        2220
        AAGAGAAACC  GACCCACCGC  GTCCCCGACG  CCGCCCGACT  TGGATGACCG  CGGTGTTTCA
        TTCTCTTTGG  CTGGGTGGCG  CAGGGGCTGC  GGCGGGCTGA  ACCTACTGGC  GCCACAAAGT 2230        2240        2250        2260        2270        2280
        CGTTATCTGT  GCCGTTTTGC  TTACGCTTAT  GATTATGGCC  ATCGGCGCGC  TCATCGCGTA
        GCAATAGACA  CGGCAAAACG  AATGCGAATA  CTAATACCGG  TAGCCGCGCG  AGTAGCGCAT 2290        2300        2310        2320        2330        2340
        CTTAAGATAT  TACCACCAGG  ACAGTTGGCG  AGACATGCTC  CACGATCTAT  TTTGCGGCTG
        GAATTCTATA  ATGGTGGTCC  TGTCAACCGC  TCTGTACGAG  GTGCTAGATA  AAACGCCGAC 2350        2360        2370        2380        2390        2400
        TCATTATCCC  GAGAAGTGCC  GTCGGCACCA  CGAGCGGCAG  AGAAGGAGAC  GGCAAGCCAT
        AGTAATAGGG  CTCTTCACGG  CAGCCGTGGT  GCTCGCCGTC  TCTTCCTCTG  CCGTTCGGTA 2410        2420        2430        2440        2450        2460
        GGATGTGCCC  GACCCGGAAC  TCGGCGACCC  GGCCCGCCGG  CCGTTGAACG  GAGCTATGTA
        CCTACACGGG  CTGGGCCTTG  AGCCGCTGGG  CCGGGCGGCC  GGCAACTTGC  CTCGATACAT 2470        2480        2490        2500        2510        2520
        CTACGGCAGC  GGCTGTCGCT  TCGACACGGT  GGAAATGGTG  GACGAGACGA  GACCCGCGCC
        GATGCCGTCG  CCGACAGCGA  AGCTGTGCCA  CCTTTACCAC  CTGCTCTGCT  CTGGGCGCGG 2530        2540        2550        2560        2570        2580
        GCCGGCGCTG  TCATCGCCCG  AAACCGGCGA  CGATAGCAAC  GACGACGCGG  TTGCCGGCGG
        CGGCCGCGAC  AGTAGCGGGC  TTTGGCCGCT  GCTATCGTTG  CTGCTGCGCC  AACGGCCGCC 2590        2600        2610        2620        2630        2640
        AGGTGCTGGC  GGGGTAACAT  CACCCGCGAC  TCGTACGACG  TCGCCGAACG  CACTGCTGCC
        TCCACGACCG  CCCCATTGTA  GTGGGCGCTG  AGCATGCTGC  AGCGGCTTGC  GTGACGACGG 2650        2660        2670        2680        2690        2700
        AGAATGGATG  GATGCGGTGC  ATGTGGCGGT  CCAAGCCGCC  GTTCAAGCGA  CCGTGCAAGT
        TCTTACCTAC  CTACGCCACG  TACACCGCCA  GGTTCGGCGG  CAAGTTCGCT  GGCACGTTCA 2710        2720        2730        2740        2750        2760
        AAGTGGCCCG  CGGGAGAACG  CCGTATCTCC  CGCTACGTAA  GAGGGTTGAG  GGGGCCGTTC
        TTCACCGGGC  GCCCTCTTGC  GGCATAGAGG  GCGATGCATT  CTCCCAACTC  CCCCGGCAAG 2770        2780        2790        2800        2810        2820
        CCGCGCGAGT  GCTGTACAAA  AGAGAGAGAC  TGGGACGTAG  ATCCGGACAG  AGGACGGTCA
        GGCGCGCTCA  CGACATGTTT  TCTCTCTCTG  ACCCTGCATC  TAGGCCTGTC  TCCTGCCAGT 2830        2840        2850        2860        2870        2880
        CCATGGACGA  TCTGCCGCTG  AATGTCGGGT  TACCCATCAT  CGGCGTGATG  CTCGTGCTGA
        GGTACCTGCT  AGACGGCGAC  TTACAGCCCA  ATGGGTAGTA  GCCGCACTAC  GAGCACGACT 2890        2900        2910        2920        2930        2940
        TCGTGGCCAT  CCTCTGCTAT  CTGGCTTACC  ACTGGCACGA  CACCTTCAAA  CTGGTGCGCA
        AGCACCGGTA  GGAGACGATA  GACCGAATGG  TGACCGTGCT  GTGGAAGTTT  GACCACGCGT 2950        2960        2970        2980        2990        3000
        TGTTTCTGAG  CTACCGCTGG  CTGATCCGCT  GTTGCGAGCT  GTACGGGGAG  TACGAGCGCC
        ACAAAGACTC  GATGGCGACC  GACTAGGCGA  CAACGCTCGA  CATGCCCCTC  ATGCTCGCGG 3010        3020        3030        3040        3050        3060
        GGTTCGCGGA  CCTGTCGTCT  CTGGGCCTCG  GCGCCGTACG  GCGGGAGTCG  GACAGACGAT
        CCAAGCGCCT  GGACAGCAGA  GACCCGGAGC  CGCGGCATGC  CGCCCTCAGC  CTGTCTGCTA
```

Fig. 1C (SEQ ID NO: 1)

```
           3070       3080       3090       3100       3110       3120
      ACCGTTTCTC CGAACGGCCC GACGAGATCT TGGTCCGTTG GGAGGAAGTG TCTTCCCAGT
      TGGCAAAGAG GCTTGCCGGG CTGCTCTAGA ACCAGGCAAC CCTCCTTCAC AGAAGGGTCA 3130       3140       3150       3160       3170       3180
      GCAGCTACGC GTCGTCGCGG ATAACAGACC GCCGTGTGGG TTCATCGTCT TCGTCGTCGG
      CGTCGATGCG CAGCAGCGCC TATTGTCTGG CGGCACACCC AAGTAGCAGA AGCAGCAGCC 3190       3200       3210       3220       3230       3240
      TCCACGTCGC TAGCCAGAGA AACAGCGTGC CTCCGCCGGA CATGGCGGTG ACGGCGCCGC
      AGGTGCAGCG ATCGGTCTCT TTGTCGCACG GAGGCGGCCT GTACCGCCAC TGCCGCGGCG 3250       3260       3270       3280       3290       3300
      TGACCGACGT CGATCTGTTG AAACCCGTGA CGGGATCCGC GACGCAGTTC ACCACCGTAG
      ACTGGCTGCA GCTAGACAAC TTTGGGCACT GCCCTAGGCG CTGCGTCAAG TGGTGGCATC 3310       3320       3330       3340       3350       3360
      CCATGGTACA TTATCATCAA GAGTACACGT GAATGAGAAA AAGAAAAAAG AGGGGAGCGG
      GGTACCATGT AATAGTAGTT CTCATGTGCA CTTACTCTTT TTCTTTTTTC TCCCCTCGCC 3370       3380       3390       3400       3410       3420
      ATCGCGATAA TGTCGCTTTG ACATTCTCTG CTCGATCTAC TCAGCGTCTG CACGAAACGG
      TAGCGCTATT ACAGCGAAAC TGTAAGAGAC GAGCTAGATG AGTCGCAGAC GTGCTTTGCC 3430       3440       3450       3460       3470       3480
      CATCCGCACG GAGGCGAGCC CAAGCGTATC TGCAGCAAGC GGTTCTTTCC CTCGGTGATG
      GTAGGCGTGC CTCCGCTCGG GTTCGCATAG ACGTCGTTCG CCAAGAAAGG GAGCCACTAC 3490       3500       3510       3520       3530       3540
      GTGGCAGCAT CGGTGGCGGG AGCTTGTTCG GACGATGGAC GGTGAGGAGT CCCTGGCGAT
      CACCGTCGTA GCCACCGCCC TCGAACAAGC CTGCTACCTG CCACTCCTCA GGGACCGCTA 3550       3560       3570       3580       3590       3600
      CAGGCGGCTC CCGGGTGTGG AGTTCAACGG GTGGTAATGG TGGCGGTGAT CGGTGTTAGA
      GTCCGCCGAG GGCCCACACC TCAAGTTGCC CACCATTACC ACCGCCACTA GCCACAATCT 3610       3620       3630       3640       3650       3660
      AAACGGTGGC CCTGGCAAAC ATATATCTAC TGTAAACCCT CTGCTCTGTT AATAAAAAGC
      TTTGCCACCG GGACCGTTTG TATATAGATG ACATTTGGGA GACGAGACAA TTATTTTTCG 3670       3680       3690       3700       3710       3720
      ACACTTTTCA CATGAGTTCG TAATTTTATT GTGTAGTGGA AATTTTTACG TCATTGGGAA
      TGTGAAAAGT GTACTCAAGC ATTAAAATAA CACATCACCT TTAAAAATGC AGTAACCCTT 3730       3740       3750       3760       3770       3780
      ACCCCAGAAT GAAAGAGTAT AATGTGCATA TCACCGGGGG TTCCCTGTCA GTACGAATGT
      TGGGGTCTTA CTTTCTCATA TTACACGTAT AGTGGCCCCC AAGGGACAGT CATGCTTACA 3790       3800       3810       3820       3830       3840
      ACACAACGCG GGTTACATTA CGATAAACTT TCCGGTAAAA CGATGCCGAT ACAGCGTGTA
      TGTGTTGCGC CCAATGTAAT GCTATTTGAA AGGCCATTTT GCTACGGCTA TGTCGCACAT 3850       3860       3870       3880       3890       3900
      TAACGCTGAT TGTTACGACA AACGAGTTGG TATATCCATT ATATAGTAAC GAACATGCTG
      ATTGCGACTA ACAATGCTGT TTGCTCAACC ATATAGGTAA TATATCATTG CTTGTACGAC 3910       3920       3930       3940       3950       3960
      TGGATATTAG TTTTATTTGC ACTCGCCGCA TCGGCGAGTG AAACCACTAC AGGTACCAGC
      ACCTATAATC AAAATAAACG TGAGCGGCGT AGCCGCTCAC TTTGGTGATG TCCATGGTCG 3970       3980       3990       4000       4010       4020
      TCTAATTCCA GTCAATCTAC TAGTGCTACC GCCAACACGA CCGTATCGAC ATGTATTAAT
      AGATTAAGGT CAGTTAGATG ATCACGATGG CGGTTGTGCT GGCATAGCTG TACATAATTA 4030       4040       4050       4060       4070       4080
      GCCTCTAACG GCAGTAGCTG GACAGTACCA CAGCTCGCGC TGCTTGCCGC TAGCGGCTGG
      CGGAGATTGC CGTCATCGAC CTGTCATGGT GTCGAGCGCG ACGAACGGCG ATCGCCGACC
```

Fig. 1D (SEQ ID NO: 1)

```
            4090       4100       4110       4120       4130       4140
       ACATTATCTG GACTCCTTCT CTTATTTACC TGCTGCTTTT GCTGCTTTTG GCTAGTACGT
       TGTAATAGAC CTGAGGAAGA GAATAAATGG ACGACGAAAA CGACGAAAAC CGATCATGCA 4150       4160       4170       4180       4190       4200
       AAAATCTGCA GCTGCTGCGG CAACTCCTCC GAGTCAGAGA GCAAAACAAC CCACGCGTAC
       TTTTAGACGT CGACGACGCC GTTGAGGAGG CTCAGTCTCT CGTTTTGTTG GGTGCGCATG 4210       4220       4230       4240       4250       4260
       ACCAATGCCG CATTCACTTC TTCCGACGCA ACGTTACCCA TGGGCACTAC AGGGTCGTAC
       TGGTTACGGC GTAAGTGAAG AAGGCTGCGT TGCAATGGGT ACCCGTGATG TCCCAGCATG 4270       4280       4290       4300       4310       4320
       ACTCCCCCAC AGGACGGCTC ATTTCCACCT CCGCCTCGGT GACGTAGGCT AAACCGAAAC
       TGAGGGGGTG TCCTGCCGAG TAAAGGTGGA GGCGGAGCCA CTGCATCCGA TTTGGCTTTG 4330       4340       4350       4360       4370       4380
       CCACGTTGAA CCTAACGCGG TTTCGGAAGG CCTGAGACGT CACTTTCACA ATGACGTCCG
       GGTGCAACTT GGATTGCGCC AAAGCCTTCC GGACTCTGCA GTGAAAGTGT TACTGCAGGC 4390       4400       4410       4420       4430       4440
       TATACACGTT CATCATAAAA CACCGTAGAG GCTAAGGCTT CGGTAGGGAG AGACCTCAAC
       ATATGTGCAA GTAGTATTTT GTGGCATCTC CGATTCCGAA GCCATCCCTC TCTGGAGTTG 4450       4460       4470       4480       4490       4500
       TGTTCCTGAT GAGCACCCGT GCTCTCATCT CTTCAGACTT GTCATGACCC CCGCTCAGAC
       ACAAGGACTA CTCGTGGGCA CGAGAGTAGA GAAGTCTGAA CAGTACTGGG GGCGAGTCTG 4510       4520       4530       4540       4550       4560
       TAACGCGACT ACCACCGTGC ACCCGCACGA CGCAAAAAAC GGCAGCGGCG GTAGTGCCCT
       ATTGCGCTGA TGGTGGCACG TGGGCGTGCT GCGTTTTTTG CCGTCGCCGC CATCACGGGA 4570       4580       4590       4600       4610       4620
       GCCGACCCTC GTCGTTTTCG GCTTTATCGT TACGCTACTT TTCTTTCTCT TTATGCTCTA
       CGGCTGGGAG CAGCAAAAGC CGAAATAGCA ATGCGATGAA AAGAAAGAGA AATACGAGAT 4630       4640       4650       4660       4670       4680
       CTTTTGGAAC AACGACGTGT TCCGTAAGCT GCTCCGTGCG CTTGGATCCA GCGCTGTTGC
       GAAAACCTTG TTGCTGCACA AGGCATTCGA CGAGGCACGC GAACCTAGGT CGCGACAACG 4690       4700       4710       4720       4730       4740
       GACCGCTTCG ACGCGTGGCA AGACGAGGTC ATCTACCGTC GTCCATCACG TCGTTCCCAG
       CTGGCGAAGC TGCGCACCGT TCTGCTCCAG TAGATGGCAG CAGGTAGTGC AGCAAGGGTC 4750       4760       4770       4780       4790       4800
       AGCGACGACG AGAGTCGTAC TAACAGCGTG TCATCGTACG TTCTTTTATC ACCCGCGTCC
       TCGCTGCTGC TCTCAGCATG ATTGTCGCAC AGTAGCATGC AAGAAAATAG TGGGCGCAGG 4810       4820       4830       4840       4850       4860
       GATGGCGGTT TTGACAACCC GGCACTGACA GAGGCCGTCG ACAGCGTGGA CGACTGGGCG
       CTACCGCCAA AACTGTTGGG CCGTGACTGT CTCCGGCAGC TGTCGCACCT GCTGACCCGC 4870       4880       4890       4900       4910       4920
       ACCACCTCGG TTTTCTACGC CACGTCCGAC GAAACGGCGG ACGCCGAGCG CCGAGACTCG
       TGGTGGAGCC AAAAGATGCG GTGCAGGCTG CTTTGCCGCC TGCGGCTCGC GGCTCTGAGC 4930       4940       4950       4960       4970       4980
       CAGCAACTGC TCATCGAGCT TCCGCCGGAG CCGCTCCCGC CCGACGTGGT GGCGGCCATG
       GTCGTTGACG AGTAGCTCGA AGGCGGCCTC GGCGAGGGCG GGCTGCACCA CCGCCGGTAC 4990       5000       5010       5020       5030       5040
       CAGAAAGCAG TGAAACGCGC TGTACAGAAC GCACTACGAC ACAGCCACGA CTCTTGGCAG
       GTCTTTCGTC ACTTTGCGCG ACATGTCTTG CGTGATGCTG TGTCGGTGCT GAGAACCGTC 5050       5060       5070       5080       5090       5100
       CTTCATCAGA CCCTGTGACG CCAGATGAAC GTTCCTTCTT AAACATCCGA GGTAGCAATG
       GAAGTAGTCT GGGACACTGC GGTCTACTTG CAAGGAAGAA TTTGTAGGCT CCATCGTTAC
```

Fig. 1E (SEQ ID NO: 1)

```
        5110       5120       5130       5140       5150       5160
AGACAGGTCG CGTACCGCCG GCGACGCGAG AGTTCCTGCG CGGTGCTGGT CCACCACGTC
TCTGTCCAGC GCATGGCGGC CGCTGCGCTC TCAAGGACGC GCCACGACCA GGTGGTGCAG
        5170       5180       5190       5200       5210       5220
GGCCGCGACG GCGACGGCGA GGGGGAGGCA GCAAAAAAGA CCTGCAAAAA AACCGGACGC
CCGGCGCTGC CGCTGCCGCT CCCCCTCCGT CGTTTTTTCT GGACGTTTTT TTGGCCTGCG
        5230       5240       5250       5260       5270       5280
TCAGTTGCGG GCATCCCGGG CGAGAAGCTG CGTCGCACGG TGGTCACCAC CACGCCGGCC
AGTCAACGCC CGTAGGGCCC GCTCTTCGAC GCAGCGTGCC ACCAGTGGTG GTGCGGCCGG
        5290       5300       5310       5320       5330       5340
CGACGTTTGA GCGGCCGACA CACGGAGCAG GAGCAGGCGG GCATGCGTCT CTGTGAAAAA
GCTGCAAACT CGCCGGCTGT GTGCCTCGTC CTCGTCCGCC CGTACGCAGA GACACTTTTT
        5350       5360       5370       5380       5390       5400
GGGAAGAAAA GAATCATCAT GTGCCGCCGG GAGTCGCTCC GAACTCTGCC GTGGCTGTTC
CCCTTCTTTT CTTAGTAGTA CACGGCGGCC CTCAGCGAGG CTTGAGACGG CACCGACAAG
        5410       5420       5430       5440       5450       5460
TGGGTGCTGT TGAGCTGCCC GCGACTCCTC GAATATTCTT CCTCTTCGTT CCCCTTCGCC
ACCCACGACA ACTCGACGGG CGCTGAGGAG CTTATAAGAA GGAGAAGCAA GGGGAAGCGG
        5470       5480       5490       5500       5510       5520
ACCGCTGACA TTGCCGAAAA GATGTGGGCC GAGAATTATG AGACCACGTC GCCGGCGCCG
TGGCGACTGT AACGGCTTTT CTACACCCGG CTCTTAATAC TCTGGTGCAG CGGCCGCGGC
        5530       5540       5550       5560       5570       5580
GTGTTGGTCG CCGAGGGAGA GCAAGTTACC ATCCCCTGCA CGGTCATGAC ACACTCCTGG
CACAACCAGC GGCTCCCTCT CGTTCAATGG TAGGGGACGT GCCAGTACTG TGTGAGGACC
        5590       5600       5610       5620       5630       5640
CCCATGGTCT CCATTCGCGC ACGTTTCTGT CGTTCCCACG ACGGCAGCGA CGAGCTCATC
GGGTACCAGA GGTAAGCGCG TGCAAAGACA GCAAGGGTGC TGCCGTCGCT GCTCGAGTAG
        5650       5660       5670       5680       5690       5700
CTGGACGCCG TCAAAGGCCA TCGGCTGATG AACGGACTCC AGTACCGCCT GCCGTACGCC
GACCTGCGGC AGTTTCCGGT AGCCGACTAC TTGCCTGAGG TCATGGCGGA CGGCATGCGG
        5710       5720       5730       5740       5750       5760
ACTTGGAATT TCTCGCAATT GCATCTCGGC CAAATATTCT CGCTTACTTT TAACGTATCG
TGAACCTTAA AGAGCGTTAA CGTAGAGCCG GTTTATAAGA GCGAATGAAA ATTGCATAGC
        5770       5780       5790       5800       5810       5820
ATGGACACAG CCGGCATGTA CGAATGCGTG CTACGCAACT ACAGCCACGG CCTCATCATG
TACCTGTGTC GGCCGTACAT GCTTACGCAC GATGCGTTGA TGTCGGTGCC GGAGTAGTAC
        5830       5840       5850       5860       5870       5880
CAACGCTTCG TAATTCTCAC GCAGCTGGAG ACGCTCAGCC GGCCCGACGA ACCTTGCTGC
GTTGCGAAGC ATTAAGAGTG CGTCGACCTC TGCGAGTCGG CCGGGCTGCT TGGAACGACG
        5890       5900       5910       5920       5930       5940
ACACCGGCGT TAGGTCGCTA CTCGCTGGGA GACCAGATCT GGTCGCCGAC GCCCTGGCGT
TGTGGCCGCA ATCCAGCGAT GAGCGACCCT CTGGTCTAGA CCAGCGGCTG CGGGACCGCA
        5950       5960       5970       5980       5990       6000
CTACGGAATC ACGACTGCGG AACGTACCGC GGCTTTCAAC GCAACTACTT CTATATCGGC
GATGCCTTAG TGCTGACGCC TTGCATGGCG CCGAAAGTTG CGTTGATGAA GATATAGCCG
        6010       6020       6030       6040       6050       6060
CGCGCCGACG CCGAGGATTG CTGGAAACCC GCATGTCCGG ACGAGGAACC CGACCGCTGT
GCGCGGCTGC GGCTCCTAAC GACCTTTGGG CGTACAGGCC TGCTCCTTGG GCTGGCGACA
        6070       6080       6090       6100       6110       6120
TGGACAGTGA TACAGCGTTA CCGGCTCCCC GGCGACTGCT ACCGTTCGCA GCCACACCCG
ACCTGTCACT ATGTCGCAAT GGCCGAGGGG CCGCTGACGA TGGCAAGCGT CGGTGTGGGC
```

Fig. 1F (SEQ ID NO: 1)

```
           6130       6140       6150       6160       6170       6180
      CCGAAATTTT TACCGGTGAC GCCAGCACCG CCGGCCGACA TAGACACCGG GATGTCTCCC
      GGCTTTAAAA ATGGCCACTG CGGTCGTGGC GGCCGGCTGT ATCTGTGGCC CTACAGAGGG
           6190       6200       6210       6220       6230       6240
      TGGGCCACTC GGGGAATCGC GGCGTTTTTG GGGTTTTGGA GTATTTTTAC CGTATGTTTC
      ACCCGGTGAG CCCCTTAGCG CCGCAAAAAC CCCAAAACCT CATAAAAATG GCATACAAAG
           6250       6260       6270       6280       6290       6300
      CTATGCTACC TGTGTTATCT GCAGTGTTGT GGACGCTGGT GTCCCACGCC GGGAAGGGGA
      GATACGATGG ACACAATAGA CGTCACAACA CCTGCGACCA CAGGGTGCGG CCCTTCCCCT
           6310       6320       6330       6340       6350       6360
      CGACGAGGCG GTGAGGGCTA TCGACGCCTA CCGACTTACG ATAGTTACCC CGGTGTTAGA
      GCTGCTCCGC CACTCCCGAT AGCTGCGGAT GGCTGAATGC TATCAATGGG GCCACAATCT
           6370       6380       6390       6400       6410       6420
      AAGATGAAGA GGTGAGAACA CGTATAAAAT AAAAAAATAA TATGTTAAAA AATGCAGTGT
      TTCTACTTCT CCACTCTTGT GCATATTTTA TTTTTTTATT ATACAATTTT TTACGTCACA
           6430       6440       6450       6460       6470       6480
      GTGAAGTGTG AATAGTGTGA TTAAAATATG CGGATTGAAT GGGTGTGGTG GTTATTCGGA
      CACTTCACAC TTATCACACT AATTTTATAC GCCTAACTTA CCCACACCAC CAATAAGCCT
           6490       6500       6510       6520       6530       6540
      TACTTTGTGT CATCCGTTGG GAGCGAACGG TCATTATCCT ATCGTTACCA CTTGGAATCT
      ATGAAACACA GTAGGCAACC CTCGCTTGCC AGTAATAGGA TAGCAATGGT GAACCTTAGA
           6550       6560       6570       6580       6590       6600
      AATTCATCTA CCAACGTGGT TTGCAACGGA AACATTTCCG TGTTTGTAAA CGGCACCCTA
      TTAAGTAGAT GGTTGCACCA AACGTTGCCT TTGTAAAGGC ACAAACATTT GCCGTGGGAT
           6610       6620       6630       6640       6650       6660
      GGTGTGCGGT ATAACATTAC GGTAGGAATC AGTTCGTCTT TATTAATAGG ACACCTTACT
      CCACACGCCA TATTGTAATG CCATCCTTAG TCAAGCAGAA ATAATTATCC TGTGGAATGA
           6670       6680       6690       6700       6710       6720
      ATACAAGTAT TGGAATCATG GTTCACACCC TGGGTCCAAA ATAAAAGTTA CAACAAACAA
      TATGTTCATA ACCTTAGTAC CAAGTGTGGG ACCCAGGTTT TATTTTCAAT GTTGTTTGTT
           6730       6740       6750       6760       6770       6780
      CCCCTAGGTG ACACTGAAAC GCTTTATAAT ATAGATAGCG AAAACATTCA TCGCGTATCT
      GGGGATCCAC TGTGACTTTG CGAAATATTA TATCTATCGC TTTTGTAAGT AGCGCATAGA
           6790       6800       6810       6820       6830       6840
      CAATATTTTC ACACAAGATG GATAAAATCT CTGCAAGAGA ATCACACTTG CGACCTCACA
      GTTATAAAAG TGTGTTCTAC CTATTTAGA GACGTTCTCT TAGTGTGAAC GCTGGAGTGT
           6850       6860       6870       6880       6890       6900
      AACAGTACAC CTACCTATAC ATATCAAGTA AACGTGAACA ACACGAATTA CCTAACACTA
      TTGTCATGTG GATGGATATG TATAGTTCAT TTGCACTTGT TGTGCTTAAT GGATTGTGAT
           6910       6920       6930       6940       6950       6960
      ACATCCTCGG GATGGCAAGA CCGTCTAAAT TACACCGTCA TAAATAGTAC ACACTTTAAC
      TGTAGGAGCC CTACCGTTCT GGCAGATTTA ATGTGGCAGT ATTTATCATG TGTGAAATTG
           6970       6980       6990       7000       7010       7020
      CTCACAGAAT CGAACATAAC CAGCATTCAA AAATATCTCA ACACTACCTG CATAGAAAGA
      GAGTGTCTTA GCTTGTATTG GTCGTAAGTT TTTATAGAGT TGTGATGGAC GTATCTTTCT
           7030       7040       7050       7060       7070       7080
      CTCCGTAACT ACACCTTGGA GTCCGTATAC ACCACAACTG TGCCTCAAAA CATAACAACA
      GAGGCATTGA TGTGGAACCT CAGGCATATG TGGTGTTGAC ACGGAGTTTT GTATTGTTGT
           7090       7100       7110       7120       7130       7140
      TCTCAACACG CAACAACCAC TATGCACACA ATACCTCCAA ATACAATAAC AATTCAAAAT
      AGAGTTGTGC GTTGTTGGTG ATACGTGTGT TATGGAGGTT TATGTTATTG TTAAGTTTTA
```

Fig. 1G (SEQ ID NO: 1)

```
              7150       7160       7170       7180       7190       7200
        ACAACTCAAA GCCATACTGT ACAGACGCCG TCTTTTAACG ACACACATAA CGTGACGAAA
        TGTTGAGTTT CGGTATGACA TGTCTGCGGC AGAAAATTGC TGTGTGTATT GCACTGCTTT
              7210       7220       7230       7240       7250       7260
        CACACGTTAA ACATAAGCTA CGTTTTATCA CAAAAAACGA ATAACACAAC ATCACCGTGG
        GTGTGCAATT TGTATTCGAT GCAAAATAGT GTTTTTTGCT TATTGTGTTG TAGTGGCACC
              7270       7280       7290       7300       7310       7320
        ATATATGCCA TACCTATGGG CGCTACAGCC ACAATAGGCG CCGGTTTATA TATCGGGAAA
        TATATACGGT ATGGATACCC GCGATGTCGG TGTTATCCGC GGCCAAATAT ATAGCCCTTT
              7330       7340       7350       7360       7370       7380
        CACTTTACGC CGGTTAAGTT CGTATACGAG GTATGGCGCG GTCAGTAAAG ACGATTCGGA
        GTGAAATGCG GCCAATTCAA GCATATGCTC CATACCGCGC CAGTCATTTC TGCTAAGCCT
              7390       7400       7410       7420       7430       7440
        TTCAACACAT ATACTCCCCA CGATCCTCGA ACACCTTACA GCATATGAGC AAAAAACAAG
        AAGTTGTGTA TATGAGGGGT GCTAGGAGCT TGTGGAATGT CGTATACTCG TTTTTTGTTC
              7450       7460       7470       7480       7490       7500
        AAAGTATAGC CACAATCACA TTTGGGCGAA TAACATGCTG TCATCCACTA GCGTCTATTA
        TTTCATATCG GTGTTAGTGT AAACCCGCTT ATTGTACGAC AGTAGGTGAT CGCAGATAAT
              7510       7520       7530       7540       7550       7560
        ATCTAATGTT TAACGGGAGC TGTACTGTCA CCGTTAAAAT ATCCATGGGA ATCAACGGGT
        TAGATTACAA ATTGCCCTCG ACATGACAGT GGCAATTTTA TAGGTACCCT TAGTTGCCCA
              7570       7580       7590       7600       7610       7620
        CAACCAACGT CCATCAGCTT GTGATTGTGC TCCATCTGGG TAACCGCTGT CAGCCTTGGC
        GTTGGTTGCA GGTAGTCGAA CACTAACACG AGGTAGACCC ATTGGCGACA GTCGGAACCG
              7630       7640       7650       7660       7670       7680
        GACAGGTGTA ATCACAGCTG TCACATAACT CACGAAGCCT CCAATCACAG CAGCACACAT
        CTGTCCACAT TAGTGTCGAC AGTGTATTGA GTGCTTCGGA GGTTAGTGTC GTCGTGTGTA
              7690       7700       7710       7720       7730       7740
        AGTCCTAACG CCATTGGCGT GTATAAAAGT TCGGAAAACT TGACGGTTGT ACGGCACGAC
        TCAGGATTGC GGTAACCGCA CATATTTTCA AGCCTTTTGA ACTGCCAACA TGCCGTGCTG
              7750       7760       7770       7780       7790       7800
        AAATCGATGT AGTGGTATGT TTTTCCAGCA GAGACCGTGT GCGGTCTCTT AGGTTCGCTA
        TTTAGCTACA TCACCATACA AAAAGGTCGT CTCTGGCACA CGCCAGAGAA TCCAAGCGAT
              7810       7820       7830       7840       7850       7860
        TACTGTGGCT GGAAACTGGT TACCTGTGAA GATGGCTAAC TATCCTGTTC TGTCCTGGAA
        ATGACACCGA CCTTTGACCA ATGGACACTT CTACCGATTG ATAGGACAAG ACAGGACCTT
              7870       7880       7890       7900       7910       7920
        AAACTTTTGG CGTCGTAGGT GGACTTTGCA GTATGCGGGT TAGTGAAGTT ATGTCATTTA
        TTTGAAAACC GCAGCATCCA CCTGAAACGT CATACGCCCA ATCACTTCAA TACAGTAAAT
              7930       7940       7950       7960       7970       7980
        TTTACGTTTA CGATCTCGTA TTACAAACCG CGGAGAGGAT GATACCGTTC GGCCCCATGA
        AAATGCAAAT GCTAGAGCAT AATGTTTGGC GCCTCTCCTA CTATGGCAAG CCGGGGTACT
              7990       8000       8010       8020       8030       8040
        GTTATTTTTA TTCTTCCGGT AGGAGGCATG AAGCCTCTGA TAATGCTCAT CTGCTTTGCT
        CAATAAAAAT AAGAAGGCCA TCCTCCGTAC TTCGGAGACT ATTACGAGTA GACGAAACGA
              8050       8060       8070       8080       8090       8100
        GTGATATTAT TGCAGCTTGG AGTGACTAAA GTGTGTCAGC ATAATGAAGT GCAACTGGGC
        CACTATAATA ACGTCGAACC TCACTGATTT CACACAGTCG TATTACTTCA CGTTGACCCG
              8110       8120       8130       8140       8150       8160
        AATGAGTGCT GCCCTCCGTG TGGTTCGGGA CAAAGAGTTA CTAAAGTATG CACGGATTAT
        TTACTCACGA CGGGAGGCAC ACCAAGCCCT GTTTCTCAAT GATTTCATAC GTGCCTAATA
```

Fig. 1H (SEQ ID NO: 1)

```
            8170       8180       8190       8200       8210       8220
       ACCAGTGTAA CGTGTACCCC TTGCCCCAAC GGCACGTATG TATCGGGACT TTACAACTGT
       TGGTCACATT GCACATGGGG AACGGGGTTG CCGTGCATAC ATAGCCCTGA AATGTTGACA
            8230       8240       8250       8260       8270       8280
       ACCGATTGCA CTCAATGTAA CGTCACTCAG GTCATGATTC GTAACTGCAC TTCCACCAAT
       TGGCTAACGT GAGTTACATT GCAGTGAGTC CAGTACTAAG CATTGACGTG AAGGTGGTTA
            8290       8300       8310       8320       8330       8340
       AATACCGTAT GCGCACCTAA GAACCATACG TACTTTTCCA CTCCAGGCGT CCAACATCAC
       TTATGGCATA CGCGTGGATT CTTGGTATGC ATGAAAAGGT GAGGTCCGCA GGTTGTAGTG
            8350       8360       8370       8380       8390       8400
       AAACAACGAC AGCAAAATCA TACCGCACAT ATAACCGTCA ACAAGGAAA AAGCGGTCGT
       TTTGTTGCTG TCGTTTTAGT ATGGCGTGTA TATTGGCAGT TGTTCCTTT TTCGCCAGCA
            8410       8420       8430       8440       8450       8460
       CATACTCTAG CCTGGTTGTC TCTCTTTATC TTTCTTGTGG GTATCATACT TTTAATTCTC
       GTATGAGATC GGACCAACAG AGAGAAATAG AAAGAACACC CATAGTATGA AAATTAAGAG
            8470       8480       8490       8500       8510       8520
       TATCTTATAG CCGCCTATCG GAGTGAGAGA TGCCAACAGT GTTGCTCAAT CGGCAAAATT
       ATAGAATATC GGCGGATAGC CTCACTCTCT ACGGTTGTCA CAACGAGTTA GCCGTTTTAA
            8530       8540       8550       8560       8570       8580
       TTCTACCGCA CCCTGTAAGC TTCCTGTTGT TGTTTTTACA TCACGGTACG ATGAAGTCAC
       AAGATGGCGT GGGACATTCG AAGGACAACA ACAAAAATGT AGTGCCATGC TACTTCAGTG
            8590       8600       8610       8620       8630       8640
       ACAGATAATT ACAGATGAGC TGTTCATATT TTTTATTATT TTTTCCAATT CCTGCACTAA
       TGTCTATTAA TGTCTACTCG ACAAGTATAA AAAATAATAA AAAAGGTTAA GGACGTGATT
            8650       8660       8670       8680       8690       8700
       AAAAAGAAGC ACTTTACGGA ACCGTGTCTG AGTATCTGTG GGGAATTTAG GTACTTTTTG
       TTTTTCTTCG TGAAATGCCT TGGCACAGAC TCATAGACAC CCCTTAAATC CATGAAAAAC
            8710       8720       8730       8740       8750       8760
       CCGACGTCAG GAAAAATAAG TGTCGCCTAC ATAAGAGCCC GGTGCTATCG TGCTGTCACT
       GGCTGCAGTC CTTTTTATTC ACAGCGGATG TATTCTCGGG CCACGATAGC ACGACAGTGA
            8770       8780       8790       8800       8810       8820
       CTTTCTTGTT GCCTTCGATG TACGGCGTCC TGGCTCATTA CTACTCCTTC ATCAGTAGCC
       GAAAGAACAA CGGAAGCTAC ATGCCGCAGG ACCGAGTAAT GATGAGGAAG TAGTCATCGG
            8830       8840       8850       8860       8870       8880
       CCAGCGTTAT GGTTAATTTT AAGCATCATA ACGCCGTGCA GCTGTTATGT GCACGGACCC
       GGTCGCAATA CCAATTAAAA TTCGTAGTAT TGCGGCACGT CGACAATACA CGTGCCTGGG
            8890       8900       8910       8920       8930       8940
       GAGACGCACT GCCGGATGGG AACGTTTAAC CCATCATGCG TCGTATCACG CGAACTACGG
       CTCTGCGTGA CGGCCTACCC TTGCAAATTG GGTAGTACGC AGCATAGTGC GCTTGATGCC
            8950       8960       8970       8980       8990       9000
       GGCATACGCC GTGTTGATGG CTACATCGCA AAGAAAGTCC CTAGTGTTAC ATCGATACAG
       CCGTATGCGG CACAACTACC GATGTAGCGT TTCTTCAGG GATCACAATG TAGCTATGTC
            9010       9020       9030       9040       9050       9060
       TGCCGTGACA GCCGTGGCCC TGCAGCTCAT GCCTGTTGAG ATCGTCCGCA AGCTAGATCA
       ACGGCACTGT CGGCACCGGG ACGTCGAGTA CGGACAACTC TAGCAGGCGT TCGATCTAGT
            9070       9080       9090       9100       9110       9120
       GTCGGACTGG GTGCGGGGTG CCTGGATCGT GTCAGAGACT TTTCCAACTA GCGACCCCAA
       CAGCCTGACC CACGCCCCAC GGACCTAGCA CAGTCTCTGA AAAGGTTGAT CGCTGGGGTT
            9130       9140       9150       9160       9170       9180
       AGGAGTTTGG AGCGACGATG ACTCCTCGAT GGGTGGAAGT GATGATTGAT GATGAGAACC
       TCCTCAAACC TCGCTGCTAC TGAGGAGCTA CCCACCTTCA CTACTAACTA CTACTCTTGG
```

Fig. 1I (SEQ ID NO: 1)

```
            9190       9200       9210       9220       9230       9240
      TGACAAGAAA GACGAGAGAG AAATTTAGAG CTGTCATTGT AGAATTAGTC TAGATTCCTG
      ACTGTTCTTT CTGCTCTCTC TTTAAATCTC GACAGTAACA TCTTAATCAG ATCTAAGGAC
            9250       9260       9270       9280       9290       9300
      ATAATAAACA GTATCGATTT TGAAACCTAA TTGACGTGTG ATCGATTTTT AAACCTCTGT
      TATTATTTGT CATAGCTAAA ACTTTGGATT AACTGCACAC TAGCTAAAAA TTTGGAGACA
            9310       9320       9330       9340       9350       9360
      GTTGTGTGAT TGATTGGTAT GTGGGGGGAT CCGATTTCAA AGGGGGGTAC TTATCGGGAA
      CAACACACTA ACTAACCATA CACCCCCCTA GGCTAAAGTT TCCCCCCATG AATAGCCCTT
            9370       9380       9390       9400       9410       9420
      TTGATGTGTC ATGGACGCAG TTTTGAGCGA TTTTCCGGGA ATACCGGATA TTACGAATTA
      AACTACACAG TACCTGCGTC AAAACTCGCT AAAAGGCCCT TATGGCCTAT AATGCTTAAT
            9430       9440       9450       9460       9470       9480
      CTGGTAGTGA CGTAGATAAT AAAATTATAA TGCGATTAAT TTTTGGTGCG TTGATTATTT
      GACCATCACT GCATCTATTA TTTTAATATT ACGCTAATTA AAAACCACGC AACTAATAAA
            9490       9500       9510       9520       9530       9540
      TTTTAGCATA TGTGTATCAT TATGAGGTGA ATGGAACAGA ATTACGCTGC AGATGTCTTC
      AAAATCGTAT ACACATAGTA ATACTCCACT TACCTTGTCT TAATGCGACG TCTACAGAAG
            9550       9560       9570       9580       9590       9600
      ATAGAAAATG GCCGCCTAAT AAAATTATAT TGGGTAATTA TTGGCTTCAT CGCGATCCCA
      TATCTTTTAC CGGCGGATTA TTTTAATATA ACCCATTAAT AACCGAAGTA GCGCTAGGGT
            9610       9620       9630       9640       9650       9660
      GAGGGCCCGG ATGCGATAAA AATGAACATT TATTGTATCC AGACGGAAGG AAACCGCCTG
      CTCCCGGGCC TACGCTATTT TTACTTGTAA ATAACATAGG TCTGCCTTCC TTTGGCGGAC
            9670       9680       9690       9700       9710       9720
      GACCTGGAGT ATGTTTATCG CCCGATCACC TCTTCTCAAA ATGGTTAGAC AAACACAACG
      CTGGACCTCA TACAAATAGC GGGCTAGTGG AGAAGAGTTT TACCAATCTG TTTGTGTTGC
            9730       9740       9750       9760       9770       9780
      ATAATAGGTG GTATAATGTT AACATAACGA AATCACCAGG ACCGAGACGA ATAAATATAA
      TATTATCCAC CATATTACAA TTGTATTGCT TTAGTGGTCC TGGCTCTGCT TATTTATATT
            9790       9800       9810       9820       9830       9840
      CCTTGATAGG TGTTAGAGGA TAATATTTAA TGTATGTTTT CAAACAGACA AGTTCGTTAA
      GGAACTATCC ACAATCTCCT ATTATAAATT ACATACAAAA GTTTGTCTGT TCAAGCAATT
            9850       9860       9870       9880       9890       9900
      AACAAAATAT TACAGTATGT GTTTAATATG GTGCTAACAT GGTTGCACCA TCCGGTTTCA
      TTGTTTTATA ATGTCATACA CAAATTATAC CACGATTGTA CCAACGTGGT AGGCAAAGT
            9910       9920       9930       9940       9950       9960
      AACTCGCATA TCAATCTGTT ATCGGTACGA CACCTGTCAT TAATCGCATA TATGTTACTT
      TTGAGCGTAT AGTTAGACAA TAGCCATGCT GTGGACAGTA ATTAGCGTAT ATACAATGAA
            9970       9980       9990      10000      10010      10020
      ACCATATGTC CCCTAGCCGT CCATGTTTTA GAACTAGAAG ATTACGACAG GCGCTGCCGT
      TGGTATACAG GGGATCGGCA GGTACAAAAT CTTGATCTTC TAATGCTGTC CGCGACGGCA
           10030      10040      10050      10060      10070      10080
      TGCAACAACC AAATTCTGTT GAATACCCTG CCGGTCGGAA CCGAATTGCT TAAGCCAATC
      ACGTTGTTGG TTTAAGACAA CTTATGGGAC GGCCAGCCTT GGCTTAACGA ATTCGGTTAG
           10090      10100      10110      10120      10130      10140
      GCAGCGAGCG AAAGCTGCAA TCGTCAGGAA GTGCTGGCTA TTTTAAAGGA CAAGGGAACC
      CGTCGCTCGC TTTCGACGTT AGCAGTCCTT CACGACCGAT AAAATTTCCT GTTCCCTTGG
           10150      10160      10170      10180      10190      10200
      AAGTGTCTCA ATCCTAACGC GCAAGCCGTG CGTCGTCACA TCAACCGGCT ATTTTTTCGG
      TTCACAGAGT TAGGATTGCG CGTTCGGCAC GCAGCAGTGT AGTTGGCCGA TAAAAAAGCC
```

Fig. 1J (SEQ ID NO: 1)

```
           10210      10220      10230      10240      10250      10260
       TTAATCTTAG ACGAGGAACA ACGCATTTAC GACGTAGTGT CTACCAATAT TGAGTTCGGT
       AATTAGAATC TGCTCCTTGT TGCGTAAATG CTGCATCACA GATGGTTATA ACTCAAGCCA
           10270      10280      10290      10300      10310      10320
       GCCTGGCCAG TCCCTACGGC CTACAAAGCC TTTCTTTGGA AATACGCCAA GAGACTGAAC
       CGGACCGGTC AGGGATGCCG GATGTTTCGG AAAGAAACCT TTATGCGGTT CTCTGACTTG
           10330      10340      10350      10360      10370      10380
       TACCACCACT TCAGACTGCG CTGGTGATCA TGTCCCTATT TTACCGTGCG GTAGCTCTGG
       ATGGTGGTGA AGTCTGACGC GACCACTAGT ACAGGGATAA AATGGCACGC CATCGAGACC
           10390      10400      10410      10420      10430      10440
       GCACGCTAAG CGCTTTGGTG TGGTACAGCA CTAGCATCCT CGCAGAGATT AACGAAAATT
       CGTGCGATTC GCGAAACCAC ACCATGTCGT GATCGTAGGA GCGTCTCTAA TTGCTTTTAA
           10450      10460      10470      10480      10490      10500
       CCTGCTCCTC ATCTTCTGCG GATCACGAAG ACTGCGAGGA ACCGGACGAG ATCGTTCGCG
       GGACGAGGAG TAGAAGACGC CTAGTGCTTC TGACGCTCCT TGGCCTGCTC TAGCAAGCGC
           10510      10520      10530      10540      10550      10560
       AAGAGCAAGA CTATCGGGCT CTGCTGGCCT TTTCCCTAGT GATTTGCGGT ACGCTCCTCG
       TTCTCGTTCT GATAGCCCGA GACGACCGGA AAAGGGATCA CTAAACGCCA TGCGAGGAGC
           10570      10580      10590      10600      10610      10620
       TCACTTGTGT GATCTGAGAC GTCATGCTGG TAGCGTTTAT GAGTCGGGCG GTGGCCGACA
       AGTGAACACA CTAGACTCTG CAGTACGACC ATCGCAAATA CTCAGCCCGC CACCGGCTGT
           10630      10640      10650      10660      10670      10680
       CGCCGCATTT CCTAACCCGC GCAGCATGTT GCGCTTGCTG TTCACGCTCG TCCTGCTGGC
       GCGGCGTAAA GGATTGGGCG CGTCGTACAA CGCGAACGAC AAGTGCGAGC AGGACGACCG
           10690      10700      10710      10720      10730      10740
       CCTCCACGGG CAGTCTGTCG GCGCTAGCCG CGACTATGTG CATGTTCGGC TACTGAGCTA
       GGAGGTGCCC GTCAGACAGC CGCGATCGGC GCTGATACAC GTACAAGCCG ATGACTCGAT
           10750      10760      10770      10780      10790      10800
       CCGAGGCGAC CCCCTGGTCT TCAAGCACAC TTTCTCGGGT GTGCGTCGAC CCTTCACCGA
       GGCTCCGCTG GGGGACCAGA AGTTCGTGTG AAAGAGCCCA CACGCAGCTG GGAAGTGGCT
           10810      10820      10830      10840      10850      10860
       GCTAGGCTGG GCTGCGTGTC GCGACTGGGA CAGTATGCAT TGCACACCCT TCTGGTCTAC
       CGATCCGACC CGACGCACAG CGCTGACCCT GTCATACGTA ACGTGTGGGA AGACCAGATG
           10870      10880      10890      10900      10910      10920
       CGATCTGGAG CAGATGACCG ACTCGGTGCG GCGTTACAGC ACGGTGAGCC CCGGCAAGGA
       GCTAGACCTC GTCTACTGGC TGAGCCACGC CGCAATGTCG TGCCACTCGG GGCCGTTCCT
           10930      10940      10950      10960      10970      10980
       AGTGACGCTT CAGCTTCACG GGAACCAAAC CGTACAGCCG TCGTTTCTAA GCTTTACGTG
       TCACTGCGAA GTCGAAGTGC CCTTGGTTTG GCATGTCGGC AGCAAAGATT CGAAATGCAC
           10990      11000      11010      11020      11030      11040
       CCGCCTGCAG CTAGAACCCG TGGTGGAAAA TGTTGGCCTC TACGTGGCCT ACGTGGTCAA
       GGCGGACGTC GATCTTGGGC ACCACCTTTT ACAACCGGAG ATGCACCGGA TGCACCAGTT
           11050      11060      11070      11080      11090      11100
       CGACGGCGAA CGCCCACAAC AGTTTTTTAC ACCGCAGGTA GACGTGGTAC GCTTGCTCT
       GCTGCCGCTT GCGGGTGTTG TCAAAAAATG TGGCGTCCAT CTGCACCATG CGAAACGAGA
           11110      11120      11130      11140      11150      11160
       ATATCTAGAA ACACTCTCCC GGATCGTGGA ACCGTTAGAA TCAGGTCGCC TGGCAGTGGA
       TATAGATCTT TGTGAGAGGG CCTAGCACCT TGGCAATCTT AGTCCAGCGG ACCGTCACCT
           11170      11180      11190      11200      11210      11220
       ATTTGATACG CCTGACCTAG CTCTGGCGCC CGATTTAGTA AGCAGCCTCT TCGTGGCCGG
       TAAACTATGC GGACTGGATC GAGACCGCGG GCTAAATCAT TCGTCGGAGA AGCACCGGCC
```

Fig. 1K (SEQ ID NO: 1)

```
          11230       11240       11250       11260       11270       11280
     ACACGGCGAG  ACCGACTTTT  ACATGAACTG  GACGCTGCGT  CGCAGTCAGA  CCCACTACCT
     TGTGCCGCTC  TGGCTGAAAA  TGTACTTGAC  CTGCGACGCA  GCGTCAGTCT  GGGTGATGGA
          11290       11300       11310       11320       11330       11340
     GGAGGAGATG  GCCTTACAGG  TGGAGATTCT  AAAACCCCGC  GGCGTACGTC  ACCGCGCTAT
     CCTCCTCTAC  CGGAATGTCC  ACCTCTAAGA  TTTTGGGGCG  CCGCATGCAG  TGGCGCGATA
          11350       11360       11370       11380       11390       11400
     TATCCACCAT  CCGAAGCTAC  AGCCGGGCGT  TGGCCTGTGG  ATAGATTTCT  GCGTGTACCG
     ATAGGTGGTA  GGCTTCGATG  TCGGCCCGCA  ACCGGACACC  TATCTAAAGA  CGCACATGGC
          11410       11420       11430       11440       11450       11460
     CTACAACGCG  CGCCTGACCC  GCGGCTACGT  ACGATACACC  CTGTCACCGA  AAGCGCGCTT
     GATGTTGCGC  GCGGACTGGG  CGCCGATGCA  TGCTATGTGG  GACAGTGGCT  TTCGCGCGAA
          11470       11480       11490       11500       11510       11520
     GCCCGCAAAA  GCAGAGGGTT  GGCTGGTGTC  ACTAGACAGA  TTCATCGTGC  AGTACCTCAA
     CGGGCGTTTT  CGTCTCCCAA  CCGACCACAG  TGATCTGTCT  AAGTAGCACG  TCATGGAGTT
          11530       11540       11550       11560       11570       11580
     CACATTGCTG  ATTACAATGA  TGGCGGCGAT  ATGGGCTCGC  GTTTTGATAA  CCTACCTGGT
     GTGTAACGAC  TAATGTTACT  ACCGCCGCTA  TACCCGAGCG  CAAAACTATT  GGATGGACCA
          11590       11600       11610       11620       11630       11640
     GTCGCGGCGT  CGGTAGAGGC  TTGCGGAAAC  CACGTCCTCG  TCACACGTCG  TTCGCGGACA
     CAGCGCCGCA  GCCATCTCCG  AACGCCTTTG  GTGCAGGAGC  AGTGTGCAGC  AAGCGCCTGT
          11650       11660       11670       11680       11690       11700
     TAGCAAGAAA  TCCACGTCGC  CACATCTCGA  GAATGCCGGC  CTTGCGGGGT  CCCCTTCGCG
     ATCGTTCTTT  AGGTGCAGCG  GTGTAGAGCT  CTTACGGCCG  GAACGCCCCA  GGGGAAGCGC
          11710       11720       11730       11740       11750       11760
     CAACATTCCT  GGCCCTGGTC  GCGTTCGGGT  TGCTGCTTCA  GATAGACCTC  AGCGACGCTA
     GTTGTAAGGA  CCGGGACCAG  CGCAAGCCCA  ACGACGAAGT  CTATCTGGAG  TCGCTGCGAT
          11770       11780       11790       11800       11810       11820
     CGAATGTGAC  CAGCAGCACA  AAAGTCCCTA  CTAGCACCAG  CAACAGAAAT  AACGTCGACA
     GCTTACACTG  GTCGTCGTGT  TTTCAGGGAT  GATCGTGGTC  GTTGTCTTTA  TTGCAGCTGT
          11830       11840       11850       11860       11870       11880
     ACGCCACGAG  TAGCGGACCC  ACAACCGGGA  TCAACATGAC  CACCACCCAC  GAGTCTTCCG
     TGCGGTGCTC  ATCGCCTGGG  TGTTGGCCCT  AGTTGTACTG  GTGGTGGGTG  CTCAGAAGGC
          11890       11900       11910       11920       11930       11940
     TTCACAACGT  GCGCAATAAC  GAGATCATGA  AAGTGCTGGC  TATCCTCTTC  TACATCGTGA
     AAGTGTTGCA  CGCGTTATTG  CTCTAGTACT  TTCACGACCG  ATAGGAGAAG  ATGTAGCACT
          11950       11960       11970       11980       11990       12000
     CAGGCACCTC  CATTTTCAGC  TTCATAGCGG  TACTGATCGC  GGTAGTTTAC  TCCTCGTGTT
     GTCCGTGGAG  GTAAAAGTCG  AAGTATCGCC  ATGACTAGCG  CCATCAAATG  AGGAGCACAA
          12010       12020       12030       12040       12050       12060
     GCAAGCACCC  GGGCCGCTTT  CGTTTCGCCG  ACGAAGAGGC  CGTCAACCTG  TTGGACGACA
     CGTTCGTGGG  CCCGGCGAAA  GCAAAGCGGC  TGCTTCTCCG  GCAGTTGGAC  AACCTGCTGT
          12070       12080       12090       12100       12110       12120
     CGGACGACAG  TGGCGGCAGC  AGCCCGTTTG  GCAGCGGTTC  CCGACGAGGT  TCTCAGATCC
     GCCTGCTGTC  ACCGCCGTCG  TCGGGCAAAC  CGTCGCCAAG  GGCTGCTCCA  AGAGTCTAGG
          12130       12140       12150       12160       12170       12180
     CCGCCGGATT  TTGTTCCTCG  AGCCCTTATC  AGCGGTTGGA  AACTCGGGAC  TGGGACGAGG
     GGCGGCCTAA  AACAAGGAGC  TCGGGAATAG  TCGCCAACCT  TTGAGCCCTG  ACCCTGCTCC
          12190       12200       12210       12220       12230       12240
     AGGAGGAGGC  GTCCGCGGCC  CGCGAGCGCA  TGAAACATGA  TCCTGAGAAC  GTCATCTATT
     TCCTCCTCCG  CAGGCGCCGG  GCGCTCGCGT  ACTTTGTACT  AGGACTCTTG  CAGTAGATAA
```

Fig. 1L (SEQ ID NO: 1)

```
           12250      12260      12270      12280      12290      12300
       TCAGAAAGGA TGGCAACTTG GACACGTCGT TCGTGAATCC CAATTATGGG AGAGGCTCGC
       AGTCTTTCCT ACCGTTGAAC CTGTGCAGCA AGCACTTAGG GTTAATACCC TCTCCGAGCG 12310      12320      12330      12340      12350      12360
       CTTTGACCAT CGAATCTCAC CTCTCGGACA ATGAGGAGGA CCCCATCAGG TACTACGTTT
       GAAACTGGTA GCTTAGAGTG GAGAGCCTGT TACTCCTCCT GGGGTAGTCC ATGATGCAAA 12370      12380      12390      12400      12410      12420
       CGGTGTACGA TGAACTGACC GCCTCGGAAA TGGAAGAACC TTCGAACAGC ACCAGCTGGC
       GCCACATGCT ACTTGACTGG CGGAGCCTTT ACCTTCTTGG AAGCTTGTCG TGGTCGACCG 12430      12440      12450      12460      12470      12480
       AGATTCCCAA ACTAATGAAA GTTGCCATGC AACCCGTCTC GCTCAGAGAT CCCGAGTACG
       TCTAAGGGTT TGATTACTTT CAACGGTACG TTGGGCAGAG CGAGTCTCTA GGGCTCATGC 12490      12500      12510      12520      12530      12540
       ACTAGGCTTT TTTTTTTGTC TTTCGGTTCC AACTCTTTCC CCGCCCCATC ACCTCGCCTG
       TGATCCGAAA AAAAAAACAG AAAGCCAAGG TTGAGAAAGG GGCGGGGTAG TGGAGCGGAC 12550      12560      12570      12580      12590      12600
       TACTATGTGT ATGATGTCTC ATAATAAAGC TTTCTTTCTC AGTCTGCAAC ATGCAGCTGT
       ATGATACACA TACTACAGAG TATTATTTCG AAAGAAAGAG TCAGACGTTG TACGTCGACA 12610      12620      12630      12640      12650      12660
       GTCGGGTGTG GCTGTCTGTT TGTCTGTGCG CCGTGGTGCT GGGTCAGTGC CAGCGGGAAA
       CAGCCCACAC CGACAGACAA ACAGACACGC GGCACCACGA CCCAGTCACG GTCGCCCTTT 12670      12680      12690      12700      12710      12720
       CCGCGGAAAA AAACGATTAT TACCGAGTAC CGCATTACTG GGACGCGTGC TCTCGCGCGC
       GGCGCCTTTT TTTGCTAATA ATGGCTCATG GCGTAATGAC CCTGCGCACG AGAGCGCGCG 12730      12740      12750      12760      12770      12780
       TGCCCGACCA AACCCGTTAC AAGTATGTGG AACAGCTCGT GGACCTCACG TTGAACTACC
       ACGGGCTGGT TTGGGCAATG TTCATACACC TTGTCGAGCA CCTGGAGTGC AACTTGATGG 12790      12800      12810      12820      12830      12840
       ACTACGATGC GAGCCACGGC TTGGACAACT TTGACGTGCT CAAGAGGTGA GGGTACGCGC
       TGATGCTACG CTCGGTGCCG AACCTGTTGA AACTGCACGA GTTCTCCACT CCCATGCGCG 12850      12860      12870      12880      12890      12900
       TAAAGGTGCA TGACAACGGG AAGGTAAGGG CGAACGGGTA ACGGCTAAGT AACCGCATGG
       ATTTCCACGT ACTGTTGCCC TTCCATTCCC GCTTGCCCAT TGCCGATTCA TTGGCGTACC 12910      12920      12930      12940      12950      12960
       GGTATGAAAT GACGTTTGGA ACCTGTGCTT GCAGAATCAA CGTGACCGAG GTGTCGTTGC
       CCATACTTTA CTGCAAACCT TGGACACGAA CGTCTTAGTT GCACTGGCTC CACAGCAACG 12970      12980      12990      13000      13010      13020
       TCATCAGCGA CTTTAGACGT CAGAACCGTC GCGGCGGCAC CAACAAAAGG ACCACGTTCA
       AGTAGTCGCT GAAATCTGCA GTCTTGGCAG CGCCGCCGTG GTTGTTTTCC TGGTGCAAGT 13030      13040      13050      13060      13070      13080
       ACGCCGCCGG TTCGCTGGCG CCACACGCCC GGAGCCTCGA GTTCAGCGTG CGGCTCTTTG
       TGCGGCGGCC AAGCGACCGC GGTGTGCGGG CCTCGGAGCT CAAGTCGCAC GCCGAGAAAC 13090      13100      13110      13120      13130      13140
       CCAACTAGCC TGCGTCACGG GAAATAATAT GCTGCGGCTT CTGCTTCGTC ACCACTTTCA
       GGTTGATCGG ACGCAGTGCC CTTTATTATA CGACGCCGAA GACGAAGCAG TGGTGAAAGT 13150      13160      13170      13180      13190      13200
       CTGCCTGCTT CTGTGCGCGG TTTGGGCAAC GCCCTGTCTG GCGTCTCCGT GGTCGACGCT
       GACGGACGAA GACACGCGCC AAACCCGTTG CGGGACAGAC CGCAGAGGCA CCAGCTGCGA 13210      13220      13230      13240      13250      13260
       AACGGCAAAC CAGAATCCGT CCCCGCCATG GTCTAAACTG ACGTATTCCA AACCGCATGA
       TTGCCGTTTG GTCTTAGGCA GGGGCGGTAC CAGATTTGAC TGCATAAGGT TTGGCGTACT
```

Fig. 1M (SEQ ID NO: 1)

```
       13270      13280      13290      13300      13310      13320
  CGCGGCGACG TTTTACTGTC CTTTTCTCTA TCCCTCGCCC CCACGGTCCC CCTTGCAATT
  GCGCCGCTGC AAAATGACAG GAAAAGAGAT AGGGAGCGGG GGTGCCAGGG GGAACGTTAA
       13330      13340      13350      13360      13370      13380
  CTCGGGGTTC CAGCAGGTAT CAACGGGTCC CGAGTGTCGC AACGAGACCC TGTATCTGCT
  GAGCCCCAAG GTCGTCCATA GTTGCCCAGG GCTCACAGCG TTGCTCTGGG ACATAGACGA
       13390      13400      13410      13420      13430      13440
  GTACAACCGG GAAGGCCAGA CCTTGGTGGA GAGAAGCTCC ACCTGGGTGA AAAAGGTGAT
  CATGTTGGCC CTTCCGGTCT GGAACCACCT CTCTTCGAGG TGGACCCACT TTTTCCACTA
       13450      13460      13470      13480      13490      13500
  CTGGTATCTG AGCGGTCGCA ACCAGACCAT CCTCCAACGG ATGCCCCAAA CGGCTTCGAA
  GACCATAGAC TCGCCAGCGT TGGTCTGGTA GGAGGTTGCC TACGGGGTTT GCCGAAGCTT
       13510      13520      13530      13540      13550      13560
  ACCGAGCGAC GGAAACGTGC AGATCAGCGT GGAAGACGCC AAGATTTTTG GAGCGCACAT
  TGGCTCGCTG CCTTTGCACG TCTAGTCGCA CCTTCTGCGG TTCTAAAAAC CTCGCGTGTA
       13570      13580      13590      13600      13610      13620
  GGTGCCCAAG CAGACCAAGC TGCTACGCTT CGTCGTCAAC GATGGCACGC GTTATCAGAT
  CCACGGGTTC GTCTGGTTCG ACGATGCGAA GCAGCAGTTG CTACCGTGCG CAATAGTCTA
       13630      13640      13650      13660      13670      13680
  GTGTGTGATG AAGCTGGAGA GCTGGGCCCA CGTCTTCCGG GACTACAGCG TGTCTTTTCA
  CACACACTAC TTCGACCTCT CGACCCGGGT GCAGAAGGCC CTGATGTCGC ACAGAAAAGT
       13690      13700      13710      13720      13730      13740
  GGTGCGATTG ACGTTCACCG AGGCCAATAA CCAGACTTAC ACCTTCTGTA CCCATCCCAA
  CCACGCTAAC TGCAAGTGGC TCCGGTTATT GGTCTGAATG TGGAAGACAT GGGTAGGGTT
       13750      13760      13770      13780      13790      13800
  TCTCATCATT TGAGCCCGTC GCGCGCGCAG GGAATTTTGA AAACCGCGCG TCATGAGTCC
  AGAGTAGTAA ACTCGGGCAG CGCGCGCGTC CCTTAAAACT TTTGGCGCGC AGTACTCAGG
       13810      13820      13830      13840      13850      13860
  CAAAGACCTG ACGCCGTTCT TGACGACGTT GTGGCTGCTA TTGGGTCACA GCCGCGTGCC
  GTTTCTGGAC TGCGGCAAGA ACTGCTGCAA CACCGACGAT AACCCAGTGT CGGCGCACGG
       13870      13880      13890      13900      13910      13920
  GCGGGTGCGC GCAGAAGAAT GTTGCGAATT CATAAACGTC AACCACCCGC CGGAACGCTG
  CGCCCACGCG CGTCTTCTTA CAACGCTTAA GTATTTGCAG TTGGTGGGCG GCCTTGCGAC
       13930      13940      13950      13960      13970      13980
  TTACGATTTC AAAATGTGCA ATCGCTTCAC CGTCGCGTAC GTATTTTCAT GATTGTCTGC
  AATGCTAAAG TTTTACACGT TAGCGAAGTG GCAGCGCATG CATAAAAGTA CTAACAGACG
       13990      14000      14010      14020      14030      14040
  GTTCTGTGGT GCGTCTGGAT TTGTCTCTCG ACGTTTCTGA TAGCCATGTT CCATCGACGA
  CAAGACACCA CGCAGACCTA ACAGAGAGC TGCAAAGACT ATCGGTACAA GGTAGCTGCT
       14050      14060      14070      14080      14090      14100
  TCCTCGGGAA TGCCAGAGTA GATTTTCATG AATCCACAGG CTGCGGTGTC CGGACGGCGA
  AGGAGCCCTT ACGGTCTCAT CTAAAAGTAC TTAGGTGTCC GACGCCACAG GCCTGCCGCT
       14110      14120      14130      14140      14150      14160
  AGTCTGCTAC AGTCCCGAGA AAACGGCTGA GATTCGCGGG ATCGTCACCA CCATGACCCA
  TCAGACGATG TCAGGGCTCT TTTGCCGACT CTAAGCGCCC TAGCAGTGGT GGTACTGGGT
       14170      14180      14190      14200      14210      14220
  TTCATTGACA CGCCAGGTCG TACACAACAA ACTGACGAGC TGCAACTACA ATCCGTAAGT
  AAGTAACTGT GCGGTCCAGC ATGTGTTGTT TGACTGCTCG ACGTTGATGT TAGGCATTCA
       14230      14240      14250      14260      14270      14280
  CTCTTCCTCG AGGGCCTTAC AGCCTATGGG AGAGTAAGAC AGAGAGGGAC AAAACATCAT
  GAGAAGGAGC TCCCGGAATG TCGGATACCC TCTCATTCTG TCTCTCCCTG TTTTGTAGTA
```

Fig. 1N (SEQ ID NO: 1)

```
            14290      14300      14310      14320      14330      14340
       TAAAAAAAAA AGTCTAATTT CACGTTTTGT ACCCCCCTTC CCCTCCGTGT TGTAGCCCAT
       ATTTTTTTTT TCAGATTAAA GTGCAAAACA TGGGGGGAAG GGGAGGCACA ACATCGGGTA
            14350      14360      14370      14380      14390      14400
       CGGCCGCGGC GATCTCCTAG TAACACTCGT CCGACACTTC CACCATCTCC AGCTCGGCCG
       GCCGGCGCCG CTAGAGGATC ATTGTGAGCA GGCTGTGAAG GTGGTAGAGG TCGAGCCGGC
            14410      14420      14430      14440      14450      14460
       GCGGTTCGGC ATCCTCTACC AGCGGCGTCG TCTCATCTTT GCCGCAGCAG CGGACGCACA
       CGCCAAGCCG TAGGAGATGG TCGCCGCAGC AGAGTAGAAA CGGCGTCGTC GCCTGCGTGT
            14470      14480      14490      14500      14510      14520
       CCTTCTCCAG GCAGAACGCC ACCAGCTGCC GCCGAACGTA CCACAGGTAC ACGTGCAGAC
       GGAAGAGGTC CGTCTTGCGG TGGTCGACGG CGGCTTGCAT GGTGTCCATG TGCACGTCTG
            14530      14540      14550      14560      14570      14580
       CTGCGAACAG GACTACGGAG GTCATGACCA CCACGACGCA CACGGGAATC CAGGGATCGA
       GACGCTTGTC CTGATGCCTC CAGTACTGGT GGTGCTGCGT GTGCCCTTAG GTCCCTAGCT
            14590      14600      14610      14620      14630      14640
       GATTGTTGCT GGAACTCATG GCTATCGCCA CCGACGTGCC CGCGTCTGTC TCACCGCCGC
       CTAACAACGA CCTTGAGTAC CGATAGCGGT GGCTGCACGG GCGCAGACAG AGTGGCGGCG
            14650      14660      14670      14680      14690      14700
       TCGCCCGATG TCGCGCGGCT TGTTATACGC TAGCCCGTCG CCGCCTCGGG GCACGGTGCC
       AGCGGGCTAC AGCGCGCCGA ACAATATGCG ATCGGGCAGC GGCGGAGCCC CGTGCCACGG
            14710      14720      14730      14740      14750      14760
       CTCCTACCCA CGTAACTTCC TCCGTGACTT AAAGTCGCGT GTGGTAGATC TCCTGCTCCG
       GAGGATGGGT GCATTGAAGG AGGCACTGAA TTTCAGCGCA CACCATCTAG AGGACGAGGC
            14770      14780      14790      14800      14810      14820
       TGGACGAACC GTCCGGCAGG ATAGCGGTTA AGGATTCGGT GCTAAGGCCG TGTCGCCAAC
       ACCTGCTTGG CAGGCCGTCC TATCGCCAAT TCCTAAGCCA CGATTCCGGC ACAGCGGTTG
            14830      14840      14850      14860      14870      14880
       GTCGAATGCT ACGTTGCAAC AGCTTCGACG GACGGCCATC CCCTCTCTCA TCGCAATAAT
       CAGCTTACGA TGCAACGTTG TCGAAGCTGC CTGCCGGTAG GGGAGAGAGT AGCGTTATTA
            14890      14900      14910      14920      14930      14940
       AAAACACCAG CAGCGCGCAC GACGCGATCA CGGTGACACC CATGATTAGA CCCACGCAGA
       TTTTGTGGTC GTCGCGCGTG CTGCGCTAGT GCCACTGTGG GTACTAATCT GGGTGCGTCT
            14950      14960      14970      14980      14990      15000
       TAGCCAGCCC CGCTAGCGTA TCTAGCGCCA TCCCGTTCGC TCCCGTTGTC TCCTGAGCGA
       ATCGGTCGGG GCGATCGCAT AGATCGCGGT AGGGCAAGCG AGGGCAACAG AGGACTCGCT
            15010      15020      15030      15040      15050      15060
       AGCAACTTCT CGGTCCCCGT TTTCAACAGT TTTTGTTTCC TTCTCCGCGA CTAGATGTTA
       TCGTTGAAGA GCCAGGGGCA AAAGTTGTCA AAAACAAAGG AAGAGGCGCT GATCTACAAT
            15070      15080      15090      15100      15110      15120
       ACGCCCGCGG TCTTTCCGGC CGTGCTCTAC CTCCTGGCGC TTGTCGTCTG GGTTGAGATG
       TGCGGGCGCC AGAAAGGCCG GCACGAGATG GAGGACCGCG AACAGCAGAC CCAACTCTAC
            15130      15140      15150      15160      15170      15180
       TTCTGCCTCG TCGCCGTAGC CGTCGTCGAG CGCGAGATCG CCTGGGCGCT GCTGCTGCGG
       AAGACGGAGC AGCGGCATCG GCAGCAGCTC GCGCTCTAGC GGACCCGCGA CGACGACGCC
            15190      15200      15210      15220      15230      15240
       ATGCTGGTCG TTGGCCTGAT GGTGGAAGTC GGCGCCGCCG CCGCTTGGAC CTTCGTGCGT
       TACGACCAGC AACCGGACTA CCACCTTCAG CCGCGGCGGC GGCGAACCTG GAAGCACGCA
            15250      15260      15270      15280      15290      15300
       TGTCTTGCCT ATCAGCGCTC CTTCCCCGTG CTTACGGCCT TCCCCTGAAA CCCACGTTAA
       ACAGAACGGA TAGTCGCGAG GAAGGGGCAC GAATGCCGGA AGGGGACTTT GGGTGCAATT
```

Fig. 1O (SEQ ID NO: 1)

```
       15310      15320      15330      15340      15350      15360
   CCGACCGTCC CAAAAACGCC GGTGTTAACA CAGGAAAAAA AGAAACCACG CAGGAACCGC
   GGCTGGCAGG GTTTTTGCGG CCACAATTGT GTCCTTTTTT TCTTTGGTGC GTCCTTGGCG 15370      15380      15390      15400      15410      15420
   GCAGGAACCA CGCGGAACAT GGGACACTAT CTGGAAATCC TGTTCAACGT CATCGTCTTC
   CGTCCTTGGT GCGCCTTGTA CCCTGTGATA GACCTTTAGG ACAAGTTGCA GTAGCAGAAG 15430      15440      15450      15460      15470      15480
   ACTCTGCTGC TCGGCGTCAT GGTCAGTATC GTCGCTTGGT ACTTCACGTG AACCACCGTC
   TGAGACGACG AGCCGCAGTA CCAGTCATAG CAGCGAACCA TGAAGTGCAC TTGGTGGCAG 15490      15500      15510      15520      15530      15540
   GTCCCGGTTT AAAAACCATC ATCGACGGCC GTTATAAAGC CACCCGGACA CGCGCCGCGG
   CAGGGCCAAA TTTTTGGTAG TAGCTGCCGG CAATATTTCG GTGGGCCTGT GCGCGGCGCC 15550      15560      15570      15580      15590      15600
   CACTTGCCTA CGGCGCTGCT TCAGGGAAAC TCCTCTTCCT TCTGCTCTTC CTCCTTCACC
   GTGAACGGAT GCCGCGACGA AGTCCCTTTG AGGAGAAGGA AGACGAGAAG GAGGAAGTGG 15610      15620      15630      15640      15650      15660
   GCAGGGATCG TTTCCCTCGA CCAGGGACTC GCCGAAGCAA CCGCCGGAGC AACCTGGAGG
   CGTCCCTAGC AAAGGGAGCT GGTCCCTGAG CGGCTTCGTT GGCGGCCTCG TTGGACCTCC 15670      15680      15690      15700      15710      15720
   AGTCGCGGCA TGACGGCGCC CAAGTGTGTC ACCACCAGTA CTTATCTGGT CAAGACCAAG
   TCAGCGCCGT ACTGCCGCGG GTTCACACAG TGGTGGTCAT GAATAGACCA GTTCTGGTTC 15730      15740      15750      15760      15770      15780
   GAACAGCCCT GGTGGCCCGA CAACGCCATC AGGAGATGGT GGATCAGTGT TGCTATCGTC
   CTTGTCGGGA CCACCGGGCT GTTGCGGTAG TCCTCTACCA CCTAGTCACA ACGATAGCAG 15790      15800      15810      15820      15830      15840
   ATCTTCATCG GAGTCTGTCT GGTGGCCCTG ATGTACTTTA CGCAGCAGCA GGCACGCAGC
   TAGAAGTAGC CTCAGACAGA CCACCGGGAC TACATGAAAT GCGTCGTCGT CCGTGCGTCG 15850      15860      15870      15880      15890      15900
   GGGAGCAGCA GCGGCTAGAC AAGTCTCTGG CGGCTACAGC TCCAAGCGCC GTAGCCGGGC
   CCCTCGTCGT CGCCGATCTG TTCAGAGACC GCCGATGTCG AGGTTCGCGG CATCGGCCCG 15910      15920      15930      15940      15950      15960
   CGCCTGCCGA TCGCGACGTC GTGGACCATC GAACAGAGAC TCACGCGTAC GAGACCCCGA
   GCGGACGGCT AGCGCTGCAG CACCTGGTAG CTTGTCTCTG AGTGCGCATG CTCTGGGGCT 15970      15980      15990      16000      16010      16020
   GGTACGCCAC GCGGTGCCTA ACGCGGTATA CCACACCCGT ACGGTCTGCA GTGCGGCGTA
   CCATGCGGTG CGCCACGGAT TGCGCCATAT GGTGTGGGCA TGCCAGACGT CACGCCGCAT 16030      16040      16050      16060      16070      16080
   CAACGTGTGG AAAACGCGTT GCGTCGCAGA GTCCGCCACG TTCCTGTCTT GTCGCTCCCC
   GTTGCACACC TTTTGCGCAA CGCAGCGTCT CAGGCGGTGC AAGGACAGAA CAGCGAGGGG 16090      16100      16110      16120      16130      16140
   AATCGTCTCC CGCACACCCC CCGCGACACC CAGAGGGCGG GTGAGCCAAG TATTCTTAAG
   TTAGCAGAGG GCGTGTGGGG GGCGCTGTGG GTCTCCCGCC CACTCGGTTC ATAAGAATTC 16150      16160      16170      16180      16190      16200
   GCCGTTCTTT GTTCCATAGC CCATAAATTG TTGATTCCGG AGCTCGTTGG CGCGGAAATA
   CGGCAAGAAA CAAGGTATCG GGTATTTAAC AACTAAGGCC TCGAGCAACC GCGCCTTTAT 16210      16220      16230      16240      16250      16260
   GCCGGATAAG GGGAGCAACA ACCGTTGGCG AAAGCCGTCC CGCTCATTCA GTCCGGGTTT
   CGGCCTATTC CCCTCGTTGT TGGCAACCGC TTTCGGCAGG GCGAGTAAGT CAGGCCCAAA 16270      16280      16290      16300      16310      16320
   CGCGTCCAGT CGGACGTGTG ACCGTTGGGC AACGGAACGG CGTTTCACTG CCAAAATCGT
   GCGCAGGTCA GCCTGCACAC TGGCAACCCG TTGCCTTGCC GCAAAGTGAC GGTTTTAGCA
```

Fig. 1P (SEQ ID NO: 1)

```
           16330      16340      16350      16360      16370      16380
      ATCGGGTAGT GTACGAGACG TCGGCGGTGC AGAATGCGAC TCGCGGCGTA GCTCGCCGTC
      TAGCCCATCA CATGCTCTGC AGCCGCCACG TCTTACGCTG AGCGCCGCAT CGAGCGGCAG 16390      16400      16410      16420      16430      16440
      GCTATGCGGC TCGTCGCCGT GTGGCGCGGC CTGGCCGGCT GTCTGCGTCC AGATCTGTTG
      CGATACGCCG AGCAGCGGCA CACCGCGCCG GACCGGCCGA CAGACGCAGG TCTAGACAAC 16450      16460      16470      16480      16490      16500
      GCCTTTTGGT TCCTCTGGCT GCTGCTGCGT GTGTGCTTTG GTAGACGCGG TGGCAGTTTG
      CGGAAAACCA AGGAGACCGA CGACGACGCA CACACGAAAC CATCTGCGCC ACCGTCAAAC 16510      16520      16530      16540      16550      16560
      CGGTCTGCGG TAAGTGAGGA TGTCGCCGAG CAAACGCACT TGCGGCGCGT GGGCGGCACG
      GCCAGACGCC ATTCACTCCT ACAGCGGCTC GTTTGCGTGA ACGCCGCGCA CCCGCCGTGC 16570      16580      16590      16600      16610      16620
      CGTGTCATTG TAGGTTCGTT GCCAGATGGC AAGTGCTGTC AACAGCAGGC GTTGTGGGCG
      GCACAGTAAC ATCCAAGCAA CGGTCTACCG TTCACGACAG TTGTCGTCCG CAACACCCGC 16630      16640      16650      16660      16670      16680
      GTCGGTGTAT TTTTGTGGGT TGCGGTGAGA GTCGGCACTC GGTGTTTTGT GAGTCATCTC
      CAGCCACATA AAAACACCCA ACGCCACTCT CAGCCGTGAG CCACAAAACA CTCAGTAGAG 16690      16700      16710      16720      16730      16740
      AACTATCTGT GTTGCTTTGA GCAGCGTCCA GAACAGCGAC GCGACTTTGG GGATGGCCTC
      TTGATAGACA CAACGAAACT CGTCGCAGGT CTTGTCGCTG CGCTGAAACC CCTACCGGAG 16750      16760      16770      16780      16790      16800
      GTGCTCACCT CCGCGGAGAG CGCCGCCGGA CCTGCTCGTC AGCAGCGAGC TACGCAGACG
      CACGAGTGGA GGCGCCTCTC GCGGCGGCCT GGACGAGCAG TCGTCGCTCG ATGCGTCTGC 16810      16820      16830      16840      16850      16860
      GAATATCTGG AGGAGAGTTA CGTGTGTCAC AGGAGAGCGC GGGTCTCCGG CGGTAACGAC
      CTTATAGACC TCCTCTCAAT GCACACAGTG TCCTCTCGCG CCCAGAGGCC GCCATTGCTG 16870      16880      16890      16900      16910      16920
      GGCGGTGTCG TCGACACGTG TGCGGCCTGT TGTGCTCTGC GGAAAAGTGC CGGTCTCGGA
      CCGCCACAGC AGCTGTGCAC ACGCCGGACA ACACGAGACG CCTTTTCACG GCCAGAGCCT 16930      16940      16950      16960      16970      16980
      GACCGTGGAC GAAAAAGAGA ACGCAGCAGC TACCGCTGGC GGCGGCGGCG TTAATGCAGC
      CTGGCACCTG CTTTTTCTCT TGCGTCGTCG ATGGCGACCG CCGCCGCCGC AATTACGTCG 16990      17000      17010      17020      17030      17040
      CGTTGATGTT CGACGTTGTG AGCACTCGGA ACAGCGGTG AGGCAGAAGG TCGATTCTCC
      GCAACTACAA GCTGCAACAC TCGTGAGCCT TTGTCGCCAC TCCGTCTTCC AGCTAAGAGG 17050      17060      17070      17080      17090      17100
      AGGGAACGAC AGTCGATGCG TGGTAGCCGC AGCAGGTGAG GTTGGGGCGG ACAACGTGTT
      TCCCTTGCTG TCAGCTACGC ACCATCGGCG TCGTCCACTC CAACCCCGCC TGTTGCACAA 17110      17120      17130      17140      17150      17160
      GCGGATTGTG GCGAGAACGT CGTCCTCCCC TTCTTCACCG CCCCACCCAC CCTCGGTTGG
      CGCCTAACAC CGCTCTTGCA GCAGGAGGGG AAGAAGTGGC GGGGTGGGTG GGAGCCAACC 17170      17180      17190      17200      17210      17220
      TGTTTCTTTT TTCTTGTGTC CTGCAGATAG TTCCACGGAC AGCGACGGCA AGTCCATAAT
      ACAAAGAAAA AAGAACACAG GACGTCTATC AAGGTGCCTG TCGCTGCCGT TCAGGTATTA 17230      17240      17250      17260      17270      17280
      CAGCGGTGTG CAAGTGGTGG AACACGACGA AGATATCATC GCGCCGCAGA GTTTGTGGTG
      GTCGCCACAC GTTCACCACC TTGTGCTGCT TCTATAGTAG CGCGGCGTCT CAAACACCAC 17290      17300      17310      17320      17330      17340
      CACGGCGTTC AAGGAAGCCC TCTGGGATGT GGCTCTGTTG GAAGTGCCGC GTTGGGCGTG
      GTGCCGCAAG TTCCTTCGGG AGACCCTACA CCGAGACAAC CTTCACGGCG CAACCCGCAC
```

Fig. 1Q (SEQ ID NO: 1)

```
           17350      17360      17370      17380      17390      17400
      GCAGGGCTGG AAGAGGTGGC GCAACAGCGA GGCCGGGCGT CGATGGAGTG CTGGGTCTGC
      CGTCCCGACC TTCTCCACCG CGTTGTCGCT CCGGCCCGCA GCTACCTCAC GACCCAGACG 17410      17420      17430      17440      17450      17460
      GTCGGCTTCC AGCTTGTCTG ACTTGGCGGG CGAGGCCGTT GGAGAATTGG TGGGATCGGT
      CAGCCGAAGG TCGAACAGAC TGAACCGCCC GCTCCGGCAA CCTCTTAACC ACCCTAGCCA 17470      17480      17490      17500      17510      17520
      CGTCGCGTAC GTGATCCTTG AACGTCTGTG GTTGGCAGCC AGAGGTTGGG TGTGCGAAAC
      GCAGCGCATG CACTAGGAAC TTGCAGACAC CAACCGTCGG TCTCCAACCC ACACGCTTTG 17530      17540      17550      17560      17570      17580
      AGGTGTGGAA GCCGAGGAGG CCATGTCGCG GCGGCGACAG CGCATGCTGT GGCGTATTGT
      TCCACACCTT CGGCTCCTCC GGTACAGCGC CGCCGCTGTC GCGTACGACA CCGCATAACA 17590      17600      17610      17620      17630      17640
      TCTCTCGTGG AGGCGACGGC GAATGCAGCA GACGGTGTTC GATGGAGATG GCGTGCGGGG
      AGAGAGCACC TCCGCTGCCG CTTACGTCGT CTGCCACAAG CTACCTCTAC CGCACGCCCC 17650      17660      17670      17680      17690      17700
      AAGAAAGCGC CGTGTTGTGA GCAGACGACG TAGGATGCGG GACGTCGGAG CACATGGGCC
      TTCTTTCGCG GCACAACACT CGTCTGCTGC ATCCTACGCC CTGCAGCCTC GTGTACCCGG 17710      17720      17730      17740      17750      17760
      ATGTGTGGTG GCAGATGGCG GTGTCCGCTG GTGTCTGCTG CGGCAGTGCA TAGACGAAGC
      TACACACCAC CGTCTACCGC CACAGGCGAC CACAGACGAC GCCGTCACGT ATCTGCTTCG 17770      17780      17790      17800      17810      17820
      AACATGTCGC TGTGAAGAGA TAGAGTGTGA GCATAGCTGC ATGCAGCGTT GCGTGTATAA
      TTGTACAGCG ACACTTCTCT ATCTCACACT CGTATCGACG TACGTCGCAA CGCACATATT 17830      17840      17850      17860      17870      17880
      GCGGGGGGGA TTAAGACGTT AATAAAGAAT AGCGGCGGTT CTGATAGGGC GACCGCTGAA
      CGCCCCCCCT AATTCTGCAA TTATTTCTTA TCGCCGCCAA GACTATCCCG CTGGCGACTT 17890      17900      17910      17920      17930      17940
      GTGAGCTGCG TGTGCGTGTG GTTTGTGGAG TCCCCGCCGC CCCCGGTCCC GTGTCCGCCG
      CACTCGACGC ACACGCACAC CAAACACCTC AGGGGCGGCG GGGGCCAGGG CACAGGCGGC 17950      17960      17970      17980      17990      18000
      GCAAAGCCCC CCGGNTCCGC ACACTCCTGG CCGCGCAACC CTCGTCGCTG CAAAAGCCCC
      CGTTTCGGGG GGCCNAGGCG TGTGAGGACC GGCGCGTTGG GAGCAGCGAC GTTTTCGGGG 18010      18020      18030      18040      18050      18060
      CCGTCCCCGC ACACCCCCGC GACCGCCGGT CCCGCGAGTC CCCGTCCCCG CCGCAAAAGG
      GGCAGGGGCG TGTGGGGGCG CTGGCGGCCA GGGCGCTCAG GGGCAGGGGC GGCGTTTTCC 18070      18080      18090      18100      18110      18120
      CCCCCGTCCT CGCCGCAAAC ACCCCCGTCA CCCCCGTCCC TCAGNCCGGG TCCGCGAGTC
      GGGGGCAGGA GCGGCGTTTG TGGGGGCAGT GGGGGCAGGG AGTCNGGCCC AGGCGCTCAG 18130      18140      18150      18160      18170      18180
      CCCGTTCCCA GCGTAATCCC CGTACCCGCA ACGNCCCGGN CCCACCGTCG TCCCGCACAC
      GGGCAAGGGT CGCATTAGGG GCATGGGCGT TGCNGGGCCN GGGTGGCAGC AGGGCGTGTG 18190      18200      18210      18220      18230      18240
      CCCCCGTCCC CCAGCCCGGT GCCCAGCGTG CGAAAAAAGC TCCGTCCCTC ACACCCGCAG
      GGGGGCAGGG GGTCGGGCCA CGGGTCGCAC GCTTTTTTCG AGGCAGGGAG TGTGGGCGTC 18250      18260      18270      18280      18290      18300
      AAAGATCCCT CAGCGCGGTG AAACCCCGTC CCCAGCGCCG TGCCGCTGAC AAAGACCATG
      TTTCTAGGGA GTCGCGCCAC TTTGGGGCAG GGGTCGCGGC ACGGCGACTG TTTCTGGTAC 18310      18320      18330      18340      18350      18360
      GGACGACACG CACAGGCA.. .......... .......... .......... ..........
      CCTGCTGTGC GTGTCCGT.. .......... .......... .......... ..........
```

Fig. 1R (SEQ ID NO: 1)

Toledo UL130 (SEQ ID NO. 2)

```
          10         20         30         40         50         60
   MLRLLLRHHF HCLLLCAVWA TPCLASPWST LTANQNPSPP WSKLTYSKPH DAATFYCPFL 70         80         90        100        110        120
   YPSPPRSPLQ FSGFQQVSTG PECRNETLYL LYNREGQTLV ERSSTWVKKV IWYLSGRNQT 130        140        150        160        170        180
   ILQRMPQTAS KPSDGNVQIS VEDAKIFGAH MVPKQTKLLR FVVNDGTRYQ MCVMKLESWA 190        200        210        220        230        240
   HVFRDYSVSF QVRLTFTEAN NQTYTFCTHP NLII*..... .......... ..........
```

Toledo UL132 (SEQ ID NO. 3)

```
          10         20         30         40         50         60
   MPALRGPLRA TFLALVAFGL LLQIDLSDAT NVTSSTKVPT STSNRNNVDN ATSSGPTTGI 70         80         90        100        110        120
   NMTTTHESSV HNVRNNEIMK VLAILFYIVT GTSIFSFIAV LIAVVYSSCC KHPGRFRFAD 130        140        150        160        170        180
   EEAVNLLDDT DDSGGSSPFG SGSRRGSQIP AGFCSSSPYQ RLETRDWDEE EEASAARERM 190        200        210        220        230        240
   KHDPENVIYF RKDGNLDTSF VNPNYGRGSP LTIESHLSDN EEDPIRYYVS VYDELTASEM 250        260        270        280        290        300
   EEPSNSTSWQ IPKLMKVAMQ PVSLRDPEYD *......... .......... ..........
```

Toledo UL133 (SEQ ID NO. 4)

```
          10         20         30         40         50         60
   MGCDVHDPSW QCQWGVPTII VAWITCAALG IWCLAGSSAD VSSGPGIAAV VGCSVFMIFL 70         80         90        100        110        120
   CAYLIRYREF FKDSVIDLLT CRWVRYCSCS CKCSCKCISG PCSRCCSACY KETMIYDMVQ 130        140        150        160        170        180
   YGHRRRPGHG DDPDRVICEI VESPPVSAPT VSVPPPSEES HQPVIPPQPP APTSEPKPKK 190        200        210        220        230        240
   GRAKDKPKGR PKDKPPCEPT VSSQPPSQPT AMPGGPPDAP PPAMPQMPPG VAEAVQAAVQ 250        260        270        280        290        300
   AAVAAALQQQ QQHQTGT*.. .......... .......... .......... ..........
```

Fig 2A

Toledo UL134 (SEQ ID NO. 5)

```
         10         20         30         40         50         60
MARTREASPV PPRSPMPSHI HTMIFSPAWN LKLRVGKGRC TDIYALDFWK RHFLARNVFI 70         80         90        100        110        120
VQTLRKEMCA KSENSLSHRG RVTFRSDAAA VVVEPRPRPP ARQLVPPRPR RVASAAWRGE 130        140        150        160        170        180
ARRADRRALP SAATVVVNSP SVRTEVCLSV YPSVYLSPYL SSVWVPMSVL AAAVG*.....
```

Toledo UL135 (SEQ ID NO. 6)

```
         10         20         30         40         50         60
MSVHRPFPTR SLRFQAGEKI MVWIWLGIGL LGGTGLASLV LAISLFTQRR GRKRSDETSS 70         80         90        100        110        120
RGRLPGAASD KRGACACCYR NPKEDVVEPL DLELGLMRVD THPPTPQVPR CTSLYIGEDG 130        140        150        160        170        180
LPIDKPEFPP ARFEIPDVST PGTPTSIGRS PSHCSSSSSL SSSTSVDTVL YQPPPSWKPP 190        200        210        220        230        240
PPPGRKKRPP TPPVRAPTTR LSSHRPPTPI PAPRKNLSTP PTKKTPPPTK PKPVGWTPPV 250        260        270        280        290        300
TPRPFPKTPT PQKPPRNPRL PRTVGLENLS KVGLSCPCPR PRTPTEPTTL PIVSVSELAP 310        320        330        340        350        360
PPRWSDIEEL LEQAVQSVMK DAESMQMT*.. .......... .......... ..........
```

Toledo UL136 (SEQ ID NO. 7)

```
         10         20         30         40         50         60
MSVKGVEMPE MTWDLDVRNK WRRRKALSRI HRFWECRLRV WWLSDAGVRE TDPPRPRRRP 70         80         90        100        110        120
TWMTAVFHVI CAVLLTLMIM AIGALIAYLR YYHQDSWRDM LHDLFCGCHY PEKCRRHHER 130        140        150        160        170        180
QRRRQAMDV PDPELGDPAR RPLNGAMYYG SGCRFDTVEM VDETRPAPPA LSSPETGDDS 190        200        210        220        230        240
NDDAVAGGGA GGVTSPATRT TSPNALLPEW MDAVHVAVQA AVQATVQVSG PRENAVSPAT 250        260        270        280        290        300
*......... .......... .......... .......... .......... ..........
```

Fig 2B

Toledo UL137 (SEQ ID NO. 8)

```
           10         20         30         40         50         60
    MATISTSITP MMGNPTFSGR SSMVTVLCPD LRPSLSLLYS TRAGTAPSTL LRSGRYGVLP 70         80         90        100        110        120
    RATYLHGRLN GGLDRHMHRI HPFWQQCVRR RRTSRG*... .......... ..........
```

Toledo UL138 (SEQ ID NO. 9)

```
           10         20         30         40         50         60
    MDDLPLNVGL PIIGVMLVLI VAILCYLAYH WHDTFKLVRM FLSYRWLIRC CELYGEYERR 70         80         90        100        110        120
    FADLSSLGLG AVRRESDRRY RFSERPDEIL VRWEEVSSQC SYASSRITDR RVGSSSSSSV 130        140        150        160        170        180
    HVASQRNSVP PPDMAVTAPL TDVDLLKPVT GSATQFTTVA MVHYHQEYT* ..........
```

Toledo UL139 (SEQ ID NO. 10)

```
           10         20         30         40         50         60
    MLWILVLFAL AASASETTTG TSSNSSQSTS ATANTTVSTC INASNGSSWT VPQLALLAAS 70         80         90        100        110        120
    GWTLSGLLLL FTCCFCCFWL VRKICSCCGN SSESESKTTH AYTNAAFTSS DATLPMGTTG 130        140        150        160        170        180
    SYTPPQDGSF PPPPR*.... .......... .......... .......... ..........
```

Toledo UL140 (SEQ ID NO. 11)

```
           10         20         30         40         50         60
    MTPAQTNATT TVHPHDAKNG SGGSALPTLV VFGFIVTLLF FLFMLYFWNN DVFRKLLRAL 70         80         90        100        110        120
    GSSAVATAST RGKTRSSTVV HHVVPRATTR VVLTACHRTF FYHPRPMAVL TTRH*.....
```

Fig 2C

Toledo UL141 (SEQ ID NO. 12)

```
         10         20         30         40         50         60
MRQVAYRRRR ESSCAVLVHH VGRDGDGEGE AAKKTCKKTG RSVAGIPGEK LRRTVVTTTP 70         80         90        100        110        120
ARRLSGRHTE QEQAGMRLCE KGKKRIIMCR RESLRTLPWL FWVLLSCPRL LEYSSSSFPF 130        140        150        160        170        180
ATADIAEKMW AENYETTSPA PVLVAEGEQV TIPCTVMTHS WPMVSIRARF CRSHDGSDEL 190        200        210        220        230        240
ILDAVKGHRL MNGLQYRLPY ATWNFSQLHL GQIFSLTFNV SMDTAGMYEC VLRNYSHGLI 250        260        270        280        290        300
MQRFVILTQL ETLSRPDEPC CTPALGRYSL GDQIWSPTPW RLRNHDCGTY RGFQRNYFYI 310        320        330        340        350        360
GRADAEDCWK PACPDEEPDR CWTVIQRYRL PGDCYRSQPH PPKFLPVTPA PPADIDTGMS 370        380        390        400        410        420
PWATRGIAAF LGFWSIFTVC FLCYLCYLQC CGRWCPTPGR GRRGGEGYRR LPTYDSYPGV 430        440        450        460        470        480
RKMKR*.... .......... .......... .......... .......... ..........
```

Toledo UL142 (SEQ ID NO. 13)

```
         10         20         30         40         50         60
MRIEWVWWLF GYFVSSVGSE RSLSYRYHLE SNSSTNVVCN GNISVFVNGT LGVRYNITVG 70         80         90        100        110        120
ISSSLLIGHL TIQVLESWFT PWVQNKSYNK QPLGDTETLY NIDSENIHRV SQYFHTRWIK 130        140        150        160        170        180
SLQENHTCDL TNSTPTYTYQ VNVNNTNYLT LTSSGWQDRL NYTVINSTHF NLTESNITSI 190        200        210        220        230        240
QKYLNTTCIE RLRNYTLESV YTTTVPQNIT TSQHATTTMH TIPPNTITIQ NTTQSHTVQT 250        260        270        280        290        300
PSFNDTHNVT KHTLNISYVL SQKTNNTTSP WIYAIPMGAT ATIGAGLYIG KHFTPVKFVY 310        320        330        340        350        360
EVWRGQ*... .......... .......... .......... .......... ..........
```

Fig 2D

Toledo UL143 (SEQ ID NO. 14)

```
          10         20         30         40         50         60
MARSVKTIRI QHIYSPRSSN TLQHMSKKQE SIATITFGRI TCCHPLASIN LMFNGSCTVT 70         80         90        100        110        120
VKISMGINGS TNVHQLVIVL HLGNRCQPWR QV*....... .......... ..........
```

Toledo UL144 (SEQ ID NO. 15)

```
          10         20         30         40         50         60
MKPLIMLICF AVILLQLGVT KVCQHNEVQL GNECCPPCGS GQRVTKVCTD YTSVTCTPCP 70         80         90        100        110        120
NGTYVSGLYN CTDCTQCNVT QVMIRNCTST NNTVCAPKNH TYFSTPGVQH HKQRQQNHTA 130        140        150        160        170        180
HITVKQGKSG RHTLAWLSLF IFLVGIILLI LYLIAAYRSE RCQQCCSIGK IFYRTL*...
```

Toledo UL145 (SEQ ID NO. 16)

```
          10         20         30         40         50         60
MCTDPRRTAG WERLTHHASY HANYGAYAVL MATSQRKSLV LHRYSAVTAV ALQLMPVEIV 70         80         90        100        110        120
RKLDQSDWVR GAWIVSETFP TSDPKGVWSD DDSSMGGSDD *......... ..........
```

Toledo UL146 (SEQ ID NO. 17)

```
          10         20         30         40         50         60
MRLIFGALII FLAYVYHYEV NGTELRCRCL HRKWPPNKII LGNYWLHRDP RGPGCDKNEH 70         80         90        100        110        120
LLYPDGRKPP GPGVCLSPDH LFSKWLDKHN DNRWYNVNIT KSPGPRRINI TLIGVRG*..
```

Fig 2E

Toledo UL147 (SEQ ID NO. 18)

```
         10         20         30         40         50         60
MVLTWLHHPV SNSHINLLSV RHLSLIAYML LTICPLAVHV LELEDYDRRC RCNNQILLNT 70         80         90        100        110        120
LPVGTELLKP IAASESCNRQ EVLAILKDKG TKCLNPNAQA VRRHINRLFF RLILDEEQRI 130        140        150        160        170        180
YDVVSTNIEF GAWPVPTAYK AFLWKYAKRL NYHHFRLRW*  .......... ..........
```

Toledo UL148 (SEQ ID NO. 19)

```
         10         20         30         40         50         60
MLRLLFTLVL LALHGQSVGA SRDYVHVRLL SYRGDPLVFK HTFSGVRRPF TELGWAACRD 70         80         90        100        110        120
WDSMHCTPFW STDLEQMTDS VRRYSTVSPG KEVTLQLHGN QTVQPSFLSF TCRLQLEPVV 130        140        150        160        170        180
ENVGLYVAYV VNDGERPQQF FTPQVDVVRF ALYLETLSRI VEPLESGRLA VEFDTPDLAL 190        200        210        220        230        240
APDLVSSLFV AGHGETDFYM NWTLRRSQTH YLEEMALQVE ILKPRGVRHR AIIHHPKLQP 250        260        270        280        290        300
GVGLWIDFCV YRYNARLTRG YVRYTLSPKA RLPAKAEGWL VSLDRFIVQY LNTLLITMMA 310        320        330        340        350        360
AIWARVLITY LVSRRR*... .......... .......... .......... ..........
```

Toledo UL149 (SEQ ID NO. 20)

```
         10         20         30         40         50         60
MVDQCCYRHL HRSLSGGPDV LYAAAGTQRE QQRLDKSLAA TAPSAVAGPP ADRDVVDHRT 70         80         90        100        110        120
ETHAYETPRY ATRCLTRYTT PVRSAVRRTT CGKRVASQSP PRSCLVAPQS SPAHPPRHPE 130        140        150        160        170        180
GG*....... .......... .......... .......... .......... ..........
```

Fig 2F

Toledo UL150 (SEQ ID NO. 21)

```
         10         20         30         40         50         60
MQLCSHSISS QRHVASSMHC RSRHQRTPPS ATTHGPCAPT SRILRRLLTT RRFLPRTPSP 70         80         90        100        110        120
SNTVCCIRRR LHERTIRHSM RCRRRDMASS ASTPVSHTQP LAANHRRSRI TYATTDPTNS 130        140        150        160        170        180
PTASPAKSDK LEADADPALH RRPASLLRHL FQPCHAQRGT SNRATSQRAS LNAVHHKLCG 190        200        210        220        230        240
AMISSSCSTT CTPLIMDLPS LSVELSAGHK KKETPTEGGW GGEEGEDDVL ATIRNTLSAP 250        260        270        280        290        300
TSPAAATTHR LSFPGESTFC LTAVSECSQR RTSTAALTPP PPAVAAAFSF SSTVSETGTF 310        320        330        340        350        360
PQSTTGRTRV DDTAVVTAGD PRSPVTHVTL LQIFRLRSSL LTSRSGGALR GGEHEAIPKV 370        380        390        400        410        420
ASLFWTLLKA TQIVEMTHKT PSADSHRNPQ KYTDRPQRLL LTALAIWQRT YNDTRAAHAP 430        440        450        460        470        480
QVRLLGDILT YRRPQTATAS TKAHTQQQPE EPKGQQIWTQ TAGQAAPHGD EPHSDGELRR 490        500        510        520        530        540
ESHSAPPTSR TLPDTILAVK RRSVAQRSHV RLDAKPGLNE RDGFRQRLLL PLSGYFRANE 550        560        570        580        590        600
LRNQQFMGYG TKNGLKNTWL TRPLGVAGGV RETIGERQDR NVADSATQRV FHTLYAALQT 610        620        630        640        650        660
VRVWYTALGT AWRTSGSRTR ESLFDGPRRR DRQAARLRRL EL*....... ..........
```

Fig 2G

Toledo UL151 (SEQ ID NO. 22)

```
         10         20         30         40         50         60
MVFVSGTALG TGFHRAEGSF CGCEGRSFFR TLGTGLGDGG CAGRRWXRXV AGTGITLGTG 70         80         90        100        110        120
TRGPGLRDGG DGGVCGEDGG LLRRGRGLAG PAVAGVCGDG GLLQRRGLRG QECAXPGGFA 130        140        150        160        170        180
GGHGTGGGGD STNHTHTQLT SAVALSEPPL FFINVLIPPA YTRNAACSYA HTLSLHSDML 190        200        210        220        230        240
LRLCTAAADT SGHRHLPPHM AHVLRRPASY VVCSQHGAFF PARHLHRTPS AAFAVASTRE 250        260        270        280        290        300
QYATACAVAA ATWPPRLPHL FRTPNLWLPT TDVQGSRTRR PIPPILQRPR PPSQTSWKPT 310        320        330        340        350        360
QTQHSIDARP RCCATSSSPA TPNAALPTEP HPRGLP*... .......... ..........
```

Fig 2H

Clinical Strains of CMV Contain Sequences Homologous to the Toledo U$_L$/b' Region Previous Towne Vaccine Strains Hybridize to the Toledo $U_L/b'$ Region

Fig. 8

Cotransfection of Cosmids Regenerates Infectious CMV
Towne•AV
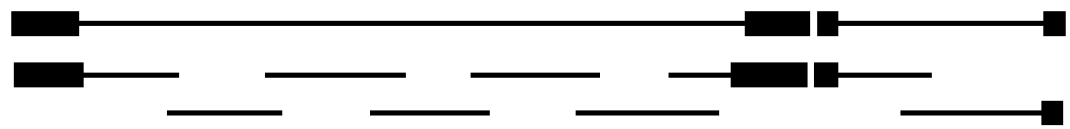
Toledo
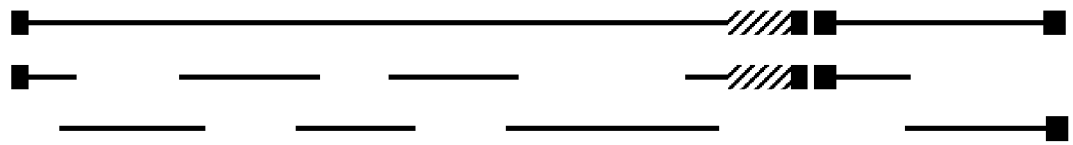
Fig. 9

Comparison of the
Towne (long) and
Towne (short) Genotypes

SEQUENCE LISTING

```
<160> NUMBER OF SEQ ID NOS: 31

<210> SEQ ID NO 1
<211> LENGTH: 18318
<212> TYPE: DNA
<213> ORGANISM: Human cytomegalovirus
<220> FEATURE:
<221> NAME/KEY: misc_feature
<222> LOCATION: (17955)..(17955)
<223> OTHER INFORMATION: n is a, c, g, or t
<220> FEATURE:
<221> NAME/KEY: misc_feature
<222> LOCATION: (18105)..(18105)
<223> OTHER INFORMATION: n is a, c, g, or t
<220> FEATURE:
<221> NAME/KEY: misc_feature
<222> LOCATION: (18154)..(18154)
<223> OTHER INFORMATION: n is a, c, g, or t
<220> FEATURE:
<221> NAME/KEY: misc_feature
<222> LOCATION: (18160)..(18160)
<223> OTHER INFORMATION: n is a, c, g, or t

<400> SEQUENCE: 1
cgctgtaggg ataaatagtg cgatggcgtt tgtgggagaa cgcagtagcg atgggttgcg     60
acgtgcacga tccttcgtgg caatgccaat ggggcgttcc cacgattatc gtggcctgga    120
taacatgcgc ggctttagga atttggtgtt tggcgggatc gtcggcggat gtctcttcgg    180
gacccggcat cgcagccgta gtcggctgtt ctgttttcat gattttcctc tgcgcgtatc    240
tcatccgtta ccgggaattc ttcaaagact ccgtaatcga cctccttacc tgccgatggg    300
ttcgctactg cagctgcagc tgtaagtgca gctgcaaatg catctcgggc ccctgtagcc    360
gctgctgttc agcgtgttac aaggagacga tgatttacga catggtccaa tacggtcatc    420
gacggcgtcc cggacacggc gacgatcccg acagggtgat ctgcgagata gtcgagagtc    480
```

```
ccccggtttc ggcgccgacg gtgtccgtcc ccccgccgtc ggaggagtcc caccagcccg      540
tcatcccacc gcagccgcca gcaccgacat cggaacccaa accgaagaaa ggtagggcga      600
aagataaacc gaagggtaga ccgaaagaca aacctccgtg cgaaccgacg gtgagttcac      660
aaccaccgtc gcagccgacg gcaatgcccg gcggtccgcc cgacgcgcct cccccgcca      720 tgccgcagat gccacccggc gtggccgagg cggtacaagc tgccgtgcag gcggccgtgg      780
ccgcggctct acaacaacag cagcagcatc agaccggaac gtaacccgcc cccggtgcga      840
taaggaattt tccgacttgg cgcacatctc cttcctcaat gtttggacaa taaacacatt      900
ccttgccaaa aaatgacgtt tccagaaatc caaggcataa atgtccgtac accggccctt      960
cccaacacgg agtttgagat tccaagcagg agagaagatc atggtgtgga tatggctcgg     1020
catcgggctc ctcggcggta ccggactggc ttccctggtc ctggccattt ccttatttac     1080
ccagcgccga ggccgcaagc gatccgacga gacttcgtcg cgaggccggc tcccgggtgc     1140
tgcttctgat aagcgtggtg cctgcgcgtg ctgctatcga aatccgaaag aagacgtcgt     1200
cgagccgctg gatctggaac tggggctcat gcgggtggac acccaccgc cgacgccgca     1260 ggtgccgcgg tgtacgtcgc tctacatagg agaggatggt ctgccgatag ataaacccga     1320
gtttcctccg cgcggttcg agatcccga cgtatccacg ccgggaacgc cgaccagcat     1380
cggccgatct ccgtcgcatt gctcctcgtc gagctctttg tcgtcctcga ccagcgtcga     1440
cacggtgctg tatcagccgc cgccatcctg aagccacct ccgccgcccg ggcgcaagaa     1500
gcggccgcct acgccgccgg tccgggcccc caccacgcgg ctgtcgtcgc acagaccccc     1560
gacgccgata cccgcgccgc gtaagaacct gagcacgccg cccaccaaga aaacgccgcc     1620
gcccacgaaa cccaagccgg tcggctggac accgccggtg acacccaggc ccttcccgaa     1680
aacgccgacg ccacaaaagc cgccgcggaa tccgagacta ccgcgcaccg tcggtctgga     1740
gaatctctcg aaggtgggac tctcgtgtcc ctgtccccga ccccgcacgc cgacggagcc     1800
gaccacgctg cctatcgtgt cggtttccga gctagccccg cctcctcgat ggtcggacat     1860
cgaggaactc ttggaacagg cggtgcagag cgtcatgaag gacgccgagt cgatgcagat     1920
gacctgagac cgaaagagcg agcgcgtccg ttgtacagtt gtatagcagc acacgccttc     1980 cctcttttc accgcagcta agagagagaa agagagtatg tcagtcaagg gcgtggagat     2040
gccagaaatg acgtgggact tggacgttag aaataaatgg cggcgtcgaa aggccctgag     2100
tcgcattcac cggttctggg aatgtcggct acgggtgtgg tggctgagtg acgccggcgt     2160
aagagaaacc gacccaccgc gtccccgacg ccgcccgact tggatgaccg cggtgtttca     2220
cgttatctgt gccgttttgc ttacgcttat gattatggcc atcggcgcgc tcatcgcgta     2280
cttaagatat taccaccagg acagttggcg agacatgctc cacgatctat tttgcggctg     2340
tcattatccc gagaagtgcc gtcggcacca cgagcggcag agaaggagac ggcaagccat     2400
ggatgtgccc gacccggaac tcggcgaccc ggcccgccgg ccgttgaacg gagctatgta     2460
ctacggcagc ggctgtcgct tcgacacggt ggaaatggtg gacgagacga gacccgcgcc     2520
gccggcgctg tcatcgcccg aaaccggcga cgatagcaac gacgacgcgg ttgccggcgg     2580
aggtgctggc ggggtaacat cacccgcgac tcgtacgacg tcgccgaacg cactgctgcc     2640
agaatggatg gatgcggtgc atgtggcggt ccaagccgcc gttcaagcga ccgtgcaagt     2700
aagtggcccg cgggagaacg ccgtatctcc cgctacgtaa gagggttgag ggggccgttc     2760
ccgcgcgagt gctgtacaaa agagagagac tgggactag atccggacag aggacggtca     2820
```

-continued

```
ccatggacga tctgccgctg aatgtcgggt tacccatcat cggcgtgatg ctcgtgctga    2880
tcgtggccat cctctgctat ctggcttacc actggcacga caccttcaaa ctggtgcgca    2940
tgtttctgag ctaccgctgg ctgatccgct gttgcgagct gtacggggag tacgagcgcc    3000
ggttcgcgga cctgtcgtct ctgggcctcg gcgccgtacg gcgggagtcg gacagacgat    3060
accgttctc cgaacggccc gacgagatct tggtccgttg ggaggaagtg tcttcccagt     3120
gcagctacgc gtcgtcgcgg ataacagacc gccgtgtggg ttcatcgtct tcgtcgtcgg    3180
tccacgtcgc tagccagaga aacagcgtgc ctccgccgga catggcggtg acggcgccgc    3240
tgaccgacgt cgatctgttg aaacccgtga cgggatccgc gacgcagttc accaccgtag    3300
ccatggtaca ttatcatcaa gagtacacgt gaatgagaaa agaaaaaag aggggagcgg     3360
atcgcgataa tgtcgctttg acattctctg ctcgatctac tcagcgtctg cacgaaacgg    3420
catccgcacg gaggcgagcc caagcgtatc tgcagcaagc ggttctttcc ctcggtgatg    3480
gtggcagcat cggtggcggg agcttgttcg gacgatggac ggtgaggagt ccctggcgat    3540
caggcggctc ccgggtgtgg agttcaacgg gtggtaatgg tggcggtgat cggtgttaga    3600
aaacggtggc cctggcaaac atatatctac tgtaaaccct ctgctctgtt aataaaaagc    3660
acacttttca catgagttcg taattttatt gtgtagtgga aattttacg tcattgggaa     3720
accccagaat gaaagagtat aatgtgcata tcacggggg ttccctgtca gtacgaatgt     3780
acacaacgcg ggttacatta cgataaactt tccggtaaaa cgatgccgat acagcgtgta    3840
taacgctgat tgttacgaca aacgagttgg tatatccatt atatagtaac gaacatgctg    3900
tggatattag ttttatttgc actcgccgca tcggcgagtg aaaccactac aggtaccagc    3960
tctaattcca gtcaatctac tagtgctacc gccaacacga ccgtatcgac atgtattaat    4020
gcctctaacg gcagtagctg gacagtacca cagctcgcgc tgcttgccgc tagcggctgg    4080
acattatctg gactccttct cttatttacc tgctgctttt gctgcttttg gctagtacgt    4140
aaaatctgca gctgctgcgg caactcctcc gagtcagaga gcaaacaac ccacgcgtac     4200
accaatgccg cattcacttc ttccgacgca acgttaccca tgggcactac agggtcgtac    4260
actccccac aggacggctc atttccacct ccgcctcggt gacgtaggct aaaccgaaac     4320
ccacgttgaa cctaacgcgg tttcggaagg cctgagacgt cactttcaca atgacgtccg    4380
tatacacgtt catcataaaa caccgtagag gctaaggctt cggtagggag agacctcaac    4440
tgttcctgat gagcacccgt gctctcatct cttcagactt gtcatgaccc ccgctcagac    4500
taacgcgact accaccgtgc acccgcacga cgcaaaaaac ggcagcggcg gtagtgccct    4560
gccgaccctc gtcgttttcg gctttatcgt tacgctactt ttctttctct ttatgctcta    4620
cttttggaac aacgacgtgt tccgtaagct gctccgtgcg cttggatcca gcgctgttgc    4680
gaccgcttcg acgcgtggca agacgaggtc atctaccgtc gtccatcacg tcgttcccag    4740
agcgacgacg agagtcgtac taacagcgtg tcatcgtacg ttcttttatc acccgcgtcc    4800
gatggcggtt ttgacaaccc ggcactgaca gaggccgtcg acagcgtgga cgactgggcg    4860
accacctcgg ttttctacgc cacgtccgac gaaacggcgg acgccgagcg ccgagactcg    4920
cagcaactgc tcatcgagct tccgccggag ccgctcccgc ccgacgtggt ggcggccatg    4980
cagaaagcag tgaaacgcgc tgtacagaac gcactacgac acagccacga ctcttggcag    5040
cttcatcaga ccctgtgacg ccagatgaac gttccttctt aaacatccga ggtagcaatg    5100
agacaggtcg cgtaccgccg gcgacgcgag agttcctgcg cggtgctggt ccaccacgtc    5160
ggccgcgacg gcgacggcga gggggaggca gcaaaaaaga cctgcaaaaa aaccggacgc    5220
```

```
tcagttgcgg gcatcccggg cgagaagctg cgtcgcacgg tggtcaccac cacgccggcc    5280
cgacgtttga gcggccgaca cacggagcag gagcaggcgg gcatgcgtct ctgtgaaaaa    5340
gggaagaaaa gaatcatcat gtgccgccgg gagtcgctcc gaactctgcc gtggctgttc    5400
tgggtgctgt tgagctgccc gcgactcctc gaatattctt cctcttcgtt ccccttcgcc    5460
accgctgaca ttgccgaaaa gatgtgggcc gagaattatg agaccacgtc gccggcgccg    5520
gtgttggtcg ccgagggaga gcaagttacc atccctgca cggtcatgac acactcctgg    5580
cccatggtct ccattcgcgc acgtttctgt cgttcccacg acggcagcga cgagctcatc    5640
ctggacgccg tcaaaggcca tcggctgatg aacggactcc agtaccgcct gccgtacgcc    5700
acttggaatt tctcgcaatt gcatctcggc caaatattct cgcttacttt taacgtatcg    5760
atggacacag ccggcatgta cgaatgcgtg ctacgcaact acagccacgg cctcatcatg    5820
caacgcttcg taattctcac gcagctggag acgctcagcc ggcccgacga accttgctgc    5880
acaccggcgt taggtcgcta ctcgctggga gaccagatct ggtcgccgac gccctggcgt    5940
ctacggaatc acgactgcgg aacgtaccgc ggctttcaac gcaactactt ctatatcggc    6000
cgcgccgacg ccgaggattg ctggaaaccc gcatgtccgg acgaggaacc cgaccgctgt    6060
tggacagtga tacagcgtta ccggctcccc ggcgactgct accgttcgca gccacacccg    6120
ccgaaatttt taccggtgac gccagcaccg ccggccgaca tagacaccgg gatgtctccc    6180
tgggccactc ggggaatcgc ggcgttttg gggttttgga gtattttttac cgtatgtttc    6240 ctatgctacc tgtgttatct gcagtgttgt ggacgctggt gtcccacgcc gggaagggga    6300
cgacgaggcg gtgagggcta tcgacgccta ccgacttacg atagttaccc cggtgttaga    6360
aagatgaaga ggtgagaaca cgtataaaat aaaaaaataa tatgttaaaa aatgcagtgt    6420
gtgaagtgtg aatagtgtga ttaaaatatg cggattgaat gggtgtggtg gttattcgga    6480
tactttgtgt catccgttgg gagcgaacgg tcattatcct atcgttacca cttggaatct    6540
aattcatcta ccaacgtggt ttgcaacgga acatttccg tgtttgtaaa cggcaccta    6600 ggtgtgcggt ataacattac ggtaggaatc agttcgtctt tattaatagg acaccttact    6660
atacaagtat tggaatcatg gttcacaccc tgggtccaaa ataaaagtta caacaaacaa    6720
cccctaggtg acactgaaac gctttatat atagatagcg aaaacattca tcgcgtatct    6780
caatattttc acacaagatg gataaaatct ctgcaagaga atcacacttg cgacctcaca    6840
aacagtacac ctaccatatac atatcaagta aacgtgaaca acacgaatta cctaacacta    6900
acatcctcgg gatggcaaga ccgtctaaat tacaccgtca taaatagtac acactttaac    6960
ctcacagaat cgaacataac cagcattcaa aaatatctca acactacctg catagaaaga    7020
ctccgtaact acaccttgga gtccgtatac accacaactg tgcctcaaaa cataacaaca    7080
tctcaacacg caacaaccac tatgcacaca ataacctccaa atacaataac aattcaaaat    7140
acaactcaaa gccatactgt acagacgccg tcttttaacg acacacataa cgtgacgaaa    7200
cacacgttaa acataagcta cgttttatca caaaaaacga ataacacaac atcaccgtgg    7260
atatatgcca tacctatggg cgctacagcc acaataggcg ccggtttata tatcgggaaa    7320
cactttacgc cggttaagtt cgtatacgag gtatggcgcg gtcagtaaag acgattcgga    7380
ttcaacacat atactcccca cgatcctcga acaccttaca gcatatgagc aaaaaacaag    7440
aaagtatagc cacaatcaca tttgggcgaa taacatgctg tcatccacta gcgtctatta    7500
atctaatgtt taacgggagc tgtactgtca ccgttaaaat atccatggga atcaacgggt    7560
```

```
caaccaacgt ccatcagctt gtgattgtgc tccatctggg taaccgctgt cagccttggc   7620
gacaggtgta atcacagctg tcacataact cacgaagcct ccaatcacag cagcacacat   7680
agtcctaacg ccattggcgt gtataaaagt tcggaaaact tgacggttgt acggcacgac   7740
aaatcgatgt agtggtatgt ttttccagca gagaccgtgt gcggtctctt aggttcgcta   7800
tactgtggct ggaaactggt tacctgtgaa gatggctaac tatcctgttc tgtcctggaa   7860
aaacttttgg cgtcgtaggt ggactttgca gtatgcgggt tagtgaagtt atgtcattta   7920
tttacgttta cgatctcgta ttacaaaccg cggagaggat gataccgttc ggccccatga   7980
gttattttta ttcttccggt aggaggcatg aagcctctga taatgctcat ctgctttgct   8040
gtgatattat tgcagcttgg agtgactaaa gtgtgtcagc ataatgaagt gcaactgggc   8100
aatgagtgct gccctccgtg tggttcggga caaagagtta ctaaagtatg cacgattat   8160 accagtgtaa cgtgtacccc ttgccccaac ggcacgtatg tatcgggact ttacaactgt   8220
accgattgca ctcaatgtaa cgtcactcag gtcatgattc gtaactgcac ttccaccaat   8280
aataccgtat gcgcacctaa gaaccatacg tacttttcca ctccaggcgt ccaacatcac   8340
aaacaacgac agcaaaatca taccgcacat ataaccgtca aacaaggaaa aagcggtcgt   8400
catactctag cctggttgtc tctctttatc tttcttgtgg gtatcatact tttaattctc   8460
tatcttatag ccgcctatcg gagtgagaga tgccaacagt gttgctcaat cggcaaaatt   8520
ttctaccgca ccctgtaagc ttcctgttgt tgttttttaca tcacggtacg atgaagtcac   8580
acagataatt acagatgagc tgttcatatt ttttattatt ttttccaatt cctgcactaa   8640
aaaaagaagc actttacgga accgtgtctg agtatctgtg gggaatttag gtactttttg   8700
ccgacgtcag gaaaaataag tgtcgcctac ataagagccc ggtgctatcg tgctgtcact   8760 cttcttgtt gccttcgatg tacggcgtcc tggctcatta ctactccttc atcagtagcc   8820
ccagcgttat ggttaattt aagcatcata acgccgtgca gctgttatgt gcacggaccc   8880
gagacgcact gccggatggg aacgtttaac ccatcatgcg tcgtatcacg cgaactacgg   8940
ggcatacgcc gtgttgatgg ctacatcgca aagaaagtcc ctagtgttac atcgatacag   9000
tgccgtgaca gccgtggccc tgcagctcat gcctgttgag atcgtccgca agctagatca   9060
gtcggactgg gtgcggggtg cctggatcgt gtcagagact tttccaacta gcgaccccaa   9120
aggagtttgg agcgacgatg actcctcgat gggtggaagt gatgattgat gatgagaacc   9180
tgacaagaaa gacgagagag aaatttagag ctgtcattgt agaattagtc tagattcctg   9240
ataataaaca gtatcgattt tgaaacctaa ttgacgtgtg atcgattttt aaacctctgt   9300
gttgtgtgat tgattggtat gtgggggat ccgatttcaa agggggtac ttatcgggaa   9360 ttgatgtgtc atggacgcag ttttgagcga ttttccggga ataccggata ttacgaatta   9420
ctggtagtga cgtagataat aaaattataa tgcgattaat ttttggtgcg ttgattattt   9480
ttttagcata tgtgtatcat tatgaggtga atggaacaga attacgctgc agatgtcttc   9540
atagaaaatg gccgcctaat aaaattatat tgggtaatta ttggcttcat cgcgatccca   9600
gagggcccgg atgcgataaa aatgaacatt tattgtatcc agacggaagg aaaccgcctg   9660
gacctggagt atgtttatcg cccgatcacc tcttctcaaa atggttagac aaacacaacg   9720
ataataggtg gtataatgtt aacataacga aatcaccagg accagacga ataaatataa   9780 ccttgatagg tgttagagga taatatttaa tgtatgtttt caaacagaca agttcgttaa   9840
aacaaaatat tacagtatgt gtttaatatg gtgctaacat ggttgcacca tccggtttca   9900
aactcgcata tcaatctgtt atcggtacga cacctgtcat taatcgcata tatgttactt   9960
```

```
accatatgtc ccctagccgt ccatgtttta gaactagaag attacgacag gcgctgccgt    10020
tgcaacaacc aaattctgtt gaataccctg ccggtcggaa ccgaattgct taagccaatc    10080
gcagcgagcg aaagctgcaa tcgtcaggaa gtgctggcta ttttaaagga caagggaacc    10140
aagtgtctca atcctaacgc gcaagccgtg cgtcgtcaca tcaaccggct attttttcgg    10200
ttaatcttag acgaggaaca acgcatttac gacgtagtgt ctaccaatat tgagttcggt    10260
gcctggccag tccctacggc ctacaaagcc tttctttgga aatacgccaa gagactgaac    10320
taccaccact tcagactgcg ctggtgatca tgtccctatt ttaccgtgcg gtagctctgg    10380
gcacgctaag cgctttggtg tggtacagca ctagcatcct cgcagagatt aacgaaaatt    10440
cctgctcctc atcttctgcg gatcacgaag actgcgagga accggacgag atcgttcgcg    10500
aagagcaaga ctatcgggct ctgctggcct tttccctagt gatttgcggt acgctcctcg    10560
tcacttgtgt gatctgagac gtcatgctgg tagcgtttat gagtcgggcg gtggccgaca    10620
cgccgcattt cctaacccgc gcagcatgtt gcgcttgctg ttcacgctcg tcctgctggc    10680
cctccacggg cagtctgtcg gcgctagccg cgactatgtg catgttcggc tactgagcta    10740
ccgaggcgac ccctggtct tcaagcacac tttctcgggt gtgcgtcgac ccttcaccga    10800
gctaggctgg gctgcgtgtc gcgactggga cagtatgcat tgcacaccct tctggtctac    10860
cgatctggag cagatgaccg actcggtgcg gcgttacagc acggtgagcc ccggcaagga    10920
agtgacgctt cagcttcacg ggaaccaaac cgtacagccg tcgtttctaa gctttacgtg    10980
ccgcctgcag ctagaacccg tggtggaaaa tgttggcctc tacgtggcct acgtggtcaa    11040
cgacggcgaa cgcccacaac agttttttac accgcaggta gacgtggtac gctttgctct    11100
atatctagaa acactctccc ggatcgtgga accgttagaa tcaggtcgcc tggcagtgga    11160
atttgatacg cctgacctag ctctggcgcc cgatttagta agcagcctct tcgtggccgg    11220
acacggcgag accgactttt acatgaactg gacgctgcgt cgcagtcaga cccactacct    11280
ggaggagatg gccttacagg tggagattct aaaaccccgc ggcgtacgtc accgcgctat    11340
tatccaccat ccgaagctac agccgggcgt tggcctgtgg atagatttct gcgtgtaccg    11400
ctacaacgcg cgcctgaccc gcggctacgt acgatacacc ctgtcaccga aagcgcgctt    11460
gcccgcaaaa gcagagggtt ggctggtgtc actagacaga ttcatcgtgc agtacctcaa    11520
cacattgctg attacaatga tggcggcgat atgggctcgc gttttgataa cctacctggt    11580
gtcgcggcgt cggtagaggc ttgcggaaac cacgtcctcg tcacacgtcg ttcgcggaca    11640
tagcaagaaa tccacgtcgc cacatctcga gaatgccggc cttgcggggt ccccttcgcg    11700
caacattcct ggccctggtc gcgttcgggt tgctgcttca gatagacctc agcgacgcta    11760
cgaatgtgac cagcagcaca aaagtcccta ctagcaccag caacagaaat aacgtcgaca    11820
acgccacgag tagcggaccc acaaccggga tcaacatgac caccacccac gagtcttccg    11880
ttcacaacgt gcgcaataac gagatcatga aagtgctggc tatcctcttc tacatcgtga    11940
caggcacctc cattttcagc ttcatagcgg tactgatcgc ggtagtttac tcctcgtgtt    12000
gcaagcaccc gggccgcttt cgtttcgccg acgaagaggc cgtcaacctg ttggacgaca    12060
cggacgacag tggcggcagc agcccgtttg gcagcggttc ccgacgaggt tctcagatcc    12120
ccgccggatt ttgttcctcg agcccttatc agcggttgga aactcgggac tgggacgagg    12180
aggaggaggc gtccgcggcc cgcgagcgca tgaaacatga tcctgagaac gtcatctatt    12240
tcagaaagga tggcaacttg gacacgtcgt tcgtgaatcc caattatggg agaggctcgc    12300
```

```
ctttgaccat cgaatctcac ctctcggaca atgaggagga ccccatcagg tactacgttt    12360
cggtgtacga tgaactgacc gcctcggaaa tggaagaacc ttcgaacagc accagctggc    12420
agattcccaa actaatgaaa gttgccatgc aacccgtctc gctcagagat cccgagtacg    12480
actaggcttt ttttttgtc tttcggttcc aactctttcc ccgccccatc acctcgcctg    12540
tactatgtgt atgatgtctc ataataaagc tttctttctc agtctgcaac atgcagctgt    12600
gtcgggtgtg gctgtctgtt tgtctgtgcg ccgtggtgct gggtcagtgc cagcgggaaa    12660
ccgcggaaaa aaacgattat taccgagtac cgcattactg ggacgcgtgc tctcgcgcgc    12720
tgcccgacca aacccgttac aagtatgtgg aacagctcgt ggacctcacg ttgaactacc    12780
actacgatgc gagccacggc ttggacaact ttgacgtgct caagaggtga gggtacgcgc    12840
taaaggtgca tgacaacggg aaggtaaggg cgaacgggta acggctaagt aaccgcatgg    12900
ggtatgaaat gacgtttgga acctgtgctt gcagaatcaa cgtgaccgag gtgtcgttgc    12960
tcatcagcga ctttagacgt cagaaccgtc gcggcggcac caacaaaagg accacgttca    13020
acgccgccgg ttcgctggcg ccacacgccc ggagcctcga gttcagcgtg cggctctttg    13080
ccaactagcc tgccgtcacgg gaaataatat gctgcggctt ctgcttcgtc accactttca    13140
ctgcctgctt ctgtgcgcgg tttgggcaac gccctgtctg gcgtctccgt ggtcgacgct    13200
aacggcaaac cagaatccgt ccccgccatg gtctaaactg acgtattcca aaccgcatga    13260
cgcggcgacg ttttactgtc cttttctcta tccctcgccc ccacggtccc ccttgcaatt    13320
ctcggggttc cagcaggtat caacgggtcc cgagtgtcgc aacgagaccc tgtatctgct    13380
gtacaaccgg gaaggccaga ccttggtgga gagaagctcc acctgggtga aaaggtgat    13440 ctggtatctg agcggtcgca accagaccat cctccaacgg atgccccaaa cggcttcgaa    13500
accgagcgac ggaaacgtgc agatcagcgt ggaagacgcc aagattttg gagcgcacat    13560 ggtgcccaag cagaccaagc tgctacgctt cgtcgtcaac gatggcacgc gttatcagat    13620
gtgtgtgatg aagctggaga gctgggccca cgtcttccgg gactacagcg tgtcttttca    13680
ggtgcgattg acgttcaccg aggccaataa ccagacttac accttctgta cccatcccaa    13740
tctcatcatt tgagcccgtc gcgcgcgcag ggaattttga aaaccgcgcg tcatgagtcc    13800
caaagacctg acgccgttct tgacgacgtt gtggctgcta ttgggtcaca gccgcgtgcc    13860
gcgggtgcgc gcagaagaat gttgcgaatt cataaacgtc aaccaccgc cggaacgctg    13920 ttacgatttc aaaatgtgca atcgcttcac cgtcgcgtac gtattttcat gattgtctgc    13980
gttctgtggt gcgtctggat ttgtctctcg acgtttctga tagccatgtt ccatcgacga    14040
tcctcgggaa tgccagagta gattttcatg aatccacagg ctgcggtgtc cggacggcga    14100
agtctgctac agtcccgaga aaacggctga gattcgcggg atcgtcacca ccatgaccca    14160
ttcattgaca cgccaggtcg tacacaacaa actgacgagc tgcaactaca atccgtaagt    14220
ctcttcctcg agggccttac agcctatggg agagtaagac agagagggac aaaacatcat    14280
taaaaaaaaa agtctaattt cacgttttgt acccccttc ccctccgtgt tgtagcccat    14340
cggccgcggc gatctcctag taacactcgt ccgacacttc caccatctcc agctcggccg    14400
gcggttcggc atcctctacc agcggcgtcg tctcatcttt gccgcagcag cggacgcaca    14460
ccttctccag gcagaacgcc accagctgcc gccgaacgta ccacaggtac acgtgcagac    14520
ctgcgaacag gactacggag gtcatgacca ccacgacgca cacgggaatc cagggatcga    14580
gattgttgct ggaactcatg gctatcgcca ccgacgtgcc cgcgtctgtc tcaccgccgc    14640
tcgcccgatg tcgcgcggct tgttatacgc tagcccgtcg ccgcctcggg gcacggtgcc    14700
```

```
ctcctaccca cgtaacttcc tccgtgactt aaagtcgcgt gtggtagatc tcctgctccg   14760
tggacgaacc gtccggcagg atagcggtta aggattcggt gctaaggccg tgtcgccaac   14820
gtcgaatgct acgttgcaac agcttcgacg gacggccatc ccctctctca tcgcaataat   14880
aaaacaccag cagcgcgcac gacgcgatca cggtgacacc catgattaga cccacgcaga   14940
tagccagccc cgctagcgta tctagcgcca tcccgttcgc tcccgttgtc tcctgagcga   15000
agcaacttct cggtccccgt tttcaacagt ttttgtttcc ttctccgcga ctagatgtta   15060
acgcccgcgg tctttccggc cgtgctctac ctcctggcgc ttgtcgtctg ggttgagatg   15120
ttctgcctcg tcgccgtagc cgtcgtcgag cgcgagatcg cctgggcgct gctgctgcgg   15180
atgctggtcg ttggcctgat ggtggaagtc ggcgccgccg ccgcttggac cttcgtgcgt   15240
tgtcttgcct atcagcgctc cttccccgtg cttacggcct tcccctgaaa cccacgttaa   15300
ccgaccgtcc caaaaacgcc ggtgttaaca caggaaaaaa agaaaccacg caggaaccgc   15360
gcaggaacca cgcggaacat gggacactat ctggaaatcc tgttcaacgt catcgtcttc   15420
actctgctgc tcggcgtcat ggtcagtatc gtcgcttggt acttcacgtg aaccaccgtc   15480
gtcccggttt aaaaaccatc atcgacggcc gttataaagc cacccggaca cgcgccgcgg   15540
cacttgccta cggcgctgct tcagggaaac tcctcttcct tctgctcttc ctccttcacc   15600
gcagggatcg tttccctcga ccagggactc gccgaagcaa ccgccggagc aacctggagg   15660
agtcgcggca tgacggcgcc caagtgtgtc accaccagta cttatctggt caagaccaag   15720
gaacagccct ggtggcccga caacgccatc aggagatggt ggatcagtgt tgctatcgtc   15780
atcttcatcg gagtctgtct ggtggccctg atgtacttta cgcagcagca ggcacgcagc   15840
gggagcagca gcggctagac aagtctctgg cggctacagc tccaagcgcc gtagccgggc   15900
cgcctgccga tcgcgacgtc gtggaccatc gaacagagac tcacgcgtac gagaccccga   15960
ggtacgccac gcggtgccta acgcggtata ccacacccgt acggtctgca gtgcggcgta   16020
caacgtgtgg aaaacgcgtt gcgtcgcaga gtccgccacg ttcctgtctt gtcgctcccc   16080
aatcgtctcc cgcacacccc ccgcgacacc cagagggcgg gtgagccaag tattcttaag   16140
gccgttcttt gttccatagc ccataaattg ttgattccgg agctcgttgg cgcggaaata   16200
gccggataag gggagcaaca accgttggcg aaagccgtcc cgctcattca gtccgggttt   16260
cgcgtccagt cggacgtgtg accgttgggc aacggaacgg cgtttcactg ccaaaatcgt   16320
atcgggtagt gtacgagacg tcggcggtgc agaatgcgac tcgcggcgta gctcgccgtc   16380
gctatgcggc tcgtcgccgt gtggcgcggc ctggccggct gtctgcgtcc agatctgttg   16440
gccttttggt tcctctggct gctgctgcgt gtgtgctttg gtagacgcgg tggcagtttg   16500
cggtctgcgg taagtgagga tgtcgccgag caaacgcact gcggcgcgt gggcggcacg   16560
cgtgtcattg taggttcgtt gccagatggc aagtgctgtc aacagcaggc gttgtgggcg   16620
gtcggtgtat ttttgtgggt tgcggtgaga gtcggcactc ggtgttttgt gagtcatctc   16680
aactatctgt gttgctttga gcagcgtcca gaacagcgac gcgactttgg ggatggcctc   16740
gtgctcacct ccgcggagag cgccgccgga cctgctcgtc agcagcgagc tacgcagacg   16800
gaatatctgg aggagagtta cgtgtgtcac aggagagcgc gggtctccgg cggtaacgac   16860
ggcggtgtcg tcgacacgtg tgcggcctgt tgtgctctgc ggaaaagtgc cggtctcgga   16920
gaccgtggac gaaaaagaga acgcagcagc taccgctggc ggcggcggcg ttaatgcagc   16980
cgttgatgtt cgacgttgtg agcactcgga aacagcggtg aggcagaagg tcgattctcc   17040
```

```
agggaacgac agtcgatgcg tggtagccgc agcaggtgag gttggggcgg acaacgtgtt    17100
gcggattgtg gcgagaacgt cgtcctcccc ttcttcaccg ccccacccac cctcggttgg    17160
tgtttctttt ttcttgtgtc ctgcagatag ttccacggac agcgacggca agtccataat    17220
cagcggtgtg caagtggtgg aacacgacga agatatcatc gcgccgcaga gtttgtggtg    17280
cacggcgttc aaggaagccc tctgggatgt ggctctgttg gaagtgccgc gttgggcgtg    17340
gcagggctgg aagaggtggc gcaacagcga ggccgggcgt cgatggagtg ctgggtctgc    17400
gtcggcttcc agcttgtctg acttggcggg cgaggccgtt ggagaattgg tgggatcggt    17460
cgtcgcgtac gtgatccttg aacgtctgtg gttggcagcc agaggttggg tgtgcgaaac    17520
aggtgtggaa gccgaggagg ccatgtcgcg gcggcgacag cgcatgctgt ggcgtattgt    17580
tctctcgtgg aggcgacggc gaatgcagca gacggtgttc gatggagatg gcgtgcgggg    17640
aagaaagcgc cgtgttgtga gcagacgacg taggatgcgg gacgtcggag cacatgggcc    17700
atgtgtggtg gcagatggcg gtgtccgctg gtgtctgctg cggcagtgca tagacgaagc    17760
aacatgtcgc tgtgaagaga tagagtgtga gcatagctgc atgcagcgtt cgtgtataa     17820 gcggggggga ttaagacgtt aataaagaat agcggcggtt ctgataggc gaccgctgaa     17880 gtgagctgcg tgtgcgtgtg gtttgtggag tccccgccgc ccccggtccc gtgtccgccg    17940
gcaaagcccc ccggntccgc acactcctgg ccgcgcaacc ctcgtcgctg caaaagcccc    18000
ccgtccccgc acaccccgc gaccgccggt cccgcgagtc cccgtccccg ccgcaaaagg     18060
cccccgtcct cgccgcaaac accccgtca ccccgtccc tcagnccggg tccgcgagtc      18120
cccgttccca gcgtaatccc cgtacccgca acgncccggn cccaccgtcg tcccgcacac    18180
cccccgtccc ccagcccggt gcccagcgtg cgaaaaaagc tccgtccctc acacccgcag    18240
aaagatccct cagcgcggtg aaacccgtc cccagcgccg tgccgctgac aaagaccatg     18300
ggacgacacg cacaggca                                                  18318

<210> SEQ ID NO 2
<211> LENGTH: 214
<212> TYPE: PRT
<213> ORGANISM: Human cytomegalovirus

<400> SEQUENCE: 2

Met Leu Arg Leu Leu Arg His His Phe His Cys Leu Leu Leu Cys
 1               5                  10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Gln Val Ser Thr Gly
 65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Gln Thr
        115                 120                 125

Ala Ser Lys Pro Ser Asp Gly Asn Val Gln Ile Ser Val Glu Asp Ala
    130                 135                 140
```

```
Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Ile
        210

<210> SEQ ID NO 3
<211> LENGTH: 270
<212> TYPE: PRT
<213> ORGANISM: Human cytomegalovirus

<400> SEQUENCE: 3

Met Pro Ala Leu Arg Gly Pro Leu Arg Ala Thr Phe Leu Ala Leu Val
1               5                   10                  15

Ala Phe Gly Leu Leu Leu Gln Ile Asp Leu Ser Asp Ala Thr Asn Val
            20                  25                  30

Thr Ser Ser Thr Lys Val Pro Thr Ser Thr Ser Asn Arg Asn Asn Val
        35                  40                  45

Asp Asn Ala Thr Ser Ser Gly Pro Thr Thr Gly Ile Asn Met Thr Thr
50                  55                  60

Thr His Glu Ser Ser Val His Asn Val Arg Asn Asn Glu Ile Met Lys
65                  70                  75                  80

Val Leu Ala Ile Leu Phe Tyr Ile Val Thr Gly Thr Ser Ile Phe Ser
                85                  90                  95

Phe Ile Ala Val Leu Ile Ala Val Val Tyr Ser Ser Cys Cys Lys His
            100                 105                 110

Pro Gly Arg Phe Arg Phe Ala Asp Glu Glu Ala Val Asn Leu Leu Asp
        115                 120                 125

Asp Thr Asp Asp Ser Gly Gly Ser Ser Pro Phe Gly Ser Gly Ser Arg
    130                 135                 140

Arg Gly Ser Gln Ile Pro Ala Gly Phe Cys Ser Ser Ser Pro Tyr Gln
145                 150                 155                 160

Arg Leu Glu Thr Arg Asp Trp Asp Glu Glu Glu Ala Ser Ala Ala
                165                 170                 175

Arg Glu Arg Met Lys His Asp Pro Glu Asn Val Ile Tyr Phe Arg Lys
            180                 185                 190

Asp Gly Asn Leu Asp Thr Ser Phe Val Asn Pro Asn Tyr Gly Arg Gly
        195                 200                 205

Ser Pro Leu Thr Ile Glu Ser His Leu Ser Asn Glu Glu Asp Pro
    210                 215                 220

Ile Arg Tyr Tyr Val Ser Val Tyr Asp Glu Leu Thr Ala Ser Glu Met
225                 230                 235                 240

Glu Glu Pro Ser Asn Ser Thr Ser Trp Gln Ile Pro Lys Leu Met Lys
                245                 250                 255

Val Ala Met Gln Pro Val Ser Leu Arg Asp Pro Glu Tyr Asp
            260                 265                 270

<210> SEQ ID NO 4
<211> LENGTH: 257
<212> TYPE: PRT
<213> ORGANISM: Human cytomegalovirus
```

<400> SEQUENCE: 4

```
Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
            20                  25                  30

Cys Leu Ala Gly Ser Ser Ala Asp Val Ser Ser Gly Pro Gly Ile Ala
        35                  40                  45

Ala Val Val Gly Cys Ser Val Phe Met Ile Phe Leu Cys Ala Tyr Leu
    50                  55                  60

Ile Arg Tyr Arg Glu Phe Phe Lys Asp Ser Val Ile Asp Leu Leu Thr
65                  70                  75                  80

Cys Arg Trp Val Arg Tyr Cys Ser Cys Ser Cys Lys Cys Ser Cys Lys
                85                  90                  95

Cys Ile Ser Gly Pro Cys Ser Arg Cys Cys Ser Ala Cys Tyr Lys Glu
                100                 105                 110

Thr Met Ile Tyr Asp Met Val Gln Tyr Gly His Arg Arg Pro Gly
            115                 120                 125

His Gly Asp Asp Pro Asp Arg Val Ile Cys Glu Ile Val Glu Ser Pro
    130                 135                 140

Pro Val Ser Ala Pro Thr Val Ser Val Pro Pro Ser Glu Glu Ser
145                 150                 155                 160

His Gln Pro Val Ile Pro Pro Gln Pro Pro Ala Pro Thr Ser Glu Pro
                165                 170                 175

Lys Pro Lys Lys Gly Arg Ala Lys Asp Lys Pro Lys Gly Arg Pro Lys
            180                 185                 190

Asp Lys Pro Pro Cys Glu Pro Thr Val Ser Ser Gln Pro Pro Ser Gln
            195                 200                 205

Pro Thr Ala Met Pro Gly Gly Pro Asp Ala Pro Pro Ala Met
        210                 215                 220

Pro Gln Met Pro Pro Gly Val Ala Glu Ala Val Gln Ala Ala Val Gln
225                 230                 235                 240

Ala Ala Val Ala Ala Ala Leu Gln Gln Gln Gln His Gln Thr Gly
                245                 250                 255

Thr
```

<210> SEQ ID NO 5
<211> LENGTH: 175
<212> TYPE: PRT
<213> ORGANISM: Human cytomegalovirus

<400> SEQUENCE: 5

```
Met Ala Arg Thr Arg Glu Ala Ser Pro Val Pro Pro Arg Ser Pro Met
1               5                   10                  15

Pro Ser His Ile His Thr Met Ile Phe Ser Pro Ala Trp Asn Leu Lys
            20                  25                  30

Leu Arg Val Gly Lys Gly Arg Cys Thr Asp Ile Tyr Ala Leu Asp Phe
        35                  40                  45

Trp Lys Arg His Phe Leu Ala Arg Asn Val Phe Ile Val Gln Thr Leu
    50                  55                  60

Arg Lys Glu Met Cys Ala Lys Ser Glu Asn Ser Leu Ser His Arg Gly
65                  70                  75                  80

Arg Val Thr Phe Arg Ser Asp Ala Ala Ala Val Val Val Glu Pro Arg
                85                  90                  95
```

```
Pro Arg Pro Pro Ala Arg Gln Leu Val Pro Pro Arg Pro Arg Arg Val
            100                 105                 110

Ala Ser Ala Ala Trp Arg Gly Glu Ala Arg Arg Ala Asp Arg Arg Ala
            115                 120                 125

Leu Pro Ser Ala Ala Thr Val Val Asn Ser Pro Ser Val Arg Thr
            130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Ala Val Gly
                165                 170                 175

<210> SEQ ID NO 6
<211> LENGTH: 328
<212> TYPE: PRT
<213> ORGANISM: Human cytomegalovirus

<400> SEQUENCE: 6

Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
        35                  40                  45

Arg Arg Gly Arg Lys Arg Ser Asp Glu Thr Ser Ser Arg Gly Arg Leu
50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
                85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
        115                 120                 125

Pro Pro Ala Arg Phe Glu Ile Pro Asp Val Ser Thr Pro Gly Thr Pro
130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
                165                 170                 175

Trp Lys Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
        195                 200                 205

Pro Ile Pro Ala Pro Arg Lys Asn Leu Ser Thr Pro Pro Thr Lys Lys
210                 215                 220

Thr Pro Pro Pro Thr Lys Pro Lys Pro Val Gly Trp Thr Pro Pro Val
225                 230                 235                 240

Thr Pro Arg Pro Phe Pro Lys Thr Pro Thr Pro Gln Lys Pro Pro Arg
            245                 250                 255

Asn Pro Arg Leu Pro Arg Thr Val Gly Leu Glu Asn Leu Ser Lys Val
        260                 265                 270

Gly Leu Ser Cys Pro Cys Pro Arg Pro Arg Thr Pro Thr Glu Pro Thr
275                 280                 285

Thr Leu Pro Ile Val Ser Val Ser Glu Leu Ala Pro Pro Arg Trp
290                 295                 300
```

Ser Asp Ile Glu Glu Leu Leu Glu Gln Ala Val Gln Ser Val Met Lys
305                 310                 315                 320

Asp Ala Glu Ser Met Gln Met Thr
                325

<210> SEQ ID NO 7
<211> LENGTH: 240
<212> TYPE: PRT
<213> ORGANISM: Human cytomegalovirus

<400> SEQUENCE: 7

Met Ser Val Lys Gly Val Glu Met Pro Glu Met Thr Trp Asp Leu Asp
1               5                   10                  15

Val Arg Asn Lys Trp Arg Arg Lys Ala Leu Ser Arg Ile His Arg
            20                  25                  30

Phe Trp Glu Cys Arg Leu Arg Val Trp Trp Leu Ser Asp Ala Gly Val
        35                  40                  45

Arg Glu Thr Asp Pro Pro Arg Pro Arg Arg Pro Thr Trp Met Thr
    50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
                85                  90                  95

Trp Arg Asp Met Leu His Asp Leu Phe Cys Gly Cys His Tyr Pro Glu
            100                 105                 110

Lys Cys Arg Arg His His Glu Arg Gln Arg Arg Arg Gln Ala Met
        115                 120                 125

Asp Val Pro Asp Pro Glu Leu Gly Asp Pro Ala Arg Arg Pro Leu Asn
130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
                165                 170                 175

Gly Asp Asp Ser Asn Asp Asp Ala Val Ala Gly Gly Ala Gly Gly
            180                 185                 190

Val Thr Ser Pro Ala Thr Arg Thr Thr Ser Pro Asn Ala Leu Leu Pro
        195                 200                 205

Glu Trp Met Asp Ala Val His Val Ala Val Gln Ala Ala Val Gln Ala
    210                 215                 220

Thr Val Gln Val Ser Gly Pro Arg Glu Asn Ala Val Ser Pro Ala Thr
225                 230                 235                 240

<210> SEQ ID NO 8
<211> LENGTH: 96
<212> TYPE: PRT
<213> ORGANISM: Human cytomegalovirus

<400> SEQUENCE: 8

Met Ala Thr Ile Ser Thr Ser Ile Thr Pro Met Met Gly Asn Pro Thr
1               5                   10                  15

Phe Ser Gly Arg Ser Ser Met Val Thr Val Leu Cys Pro Asp Leu Arg
            20                  25                  30

Pro Ser Leu Ser Leu Leu Tyr Ser Thr Arg Ala Gly Thr Ala Pro Ser
        35                  40                  45

Thr Leu Leu Arg Ser Gly Arg Tyr Gly Val Leu Pro Arg Ala Thr Tyr
    50                  55                  60

```
Leu His Gly Arg Leu Asn Gly Gly Leu Asp Arg His Met His Arg Ile
 65                  70                  75                  80

His Pro Phe Trp Gln Gln Cys Val Arg Arg Arg Thr Ser Arg Gly
                 85                  90                  95
```

<210> SEQ ID NO 9
<211> LENGTH: 169
<212> TYPE: PRT
<213> ORGANISM: Human cytomegalovirus

<400> SEQUENCE: 9

```
Met Asp Asp Leu Pro Leu Asn Val Gly Leu Pro Ile Ile Gly Val Met
  1               5                  10                  15

Leu Val Leu Ile Val Ala Ile Leu Cys Tyr Leu Ala Tyr His Trp His
                 20                  25                  30

Asp Thr Phe Lys Leu Val Arg Met Phe Leu Ser Tyr Arg Trp Leu Ile
             35                  40                  45

Arg Cys Cys Glu Leu Tyr Gly Glu Tyr Glu Arg Arg Phe Ala Asp Leu
 50                  55                  60

Ser Ser Leu Gly Leu Gly Ala Val Arg Arg Ser Asp Arg Arg Tyr
 65                  70                  75                  80

Arg Phe Ser Glu Arg Pro Asp Glu Ile Leu Val Arg Trp Glu Val
                 85                  90                  95

Ser Ser Gln Cys Ser Tyr Ala Ser Ser Arg Ile Thr Asp Arg Arg Val
                100                 105                 110

Gly Ser Ser Ser Ser Ser Val His Val Ala Ser Gln Arg Asn Ser
                115                 120                 125

Val Pro Pro Asp Met Ala Val Thr Ala Pro Leu Thr Asp Val Asp
    130                 135                 140

Leu Leu Lys Pro Val Thr Gly Ser Ala Thr Gln Phe Thr Thr Val Ala
145                 150                 155                 160

Met Val His Tyr His Gln Glu Tyr Thr
                165
```

<210> SEQ ID NO 10
<211> LENGTH: 135
<212> TYPE: PRT
<213> ORGANISM: Human cytomegalovirus

<400> SEQUENCE: 10

```
Met Leu Trp Ile Leu Val Leu Phe Ala Leu Ala Ala Ser Ala Ser Glu
  1               5                  10                  15

Thr Thr Thr Gly Thr Ser Ser Asn Ser Ser Gln Ser Thr Ser Ala Thr
                 20                  25                  30

Ala Asn Thr Thr Val Ser Thr Cys Ile Asn Ala Ser Asn Gly Ser Ser
             35                  40                  45

Trp Thr Val Pro Gln Leu Ala Leu Leu Ala Ala Ser Gly Trp Thr Leu
 50                  55                  60

Ser Gly Leu Leu Leu Leu Phe Thr Cys Cys Phe Cys Phe Trp Leu
 65                  70                  75                  80

Val Arg Lys Ile Cys Ser Cys Cys Gly Asn Ser Ser Glu Ser Glu Ser
                 85                  90                  95

Lys Thr Thr His Ala Tyr Thr Asn Ala Ala Phe Thr Ser Ser Asp Ala
                100                 105                 110

Thr Leu Pro Met Gly Thr Thr Gly Ser Tyr Thr Pro Pro Gln Asp Gly
                115                 120                 125
```

```
Ser Phe Pro Pro Pro Arg
    130             135

<210> SEQ ID NO 11
<211> LENGTH: 114
<212> TYPE: PRT
<213> ORGANISM: Human cytomegalovirus

<400> SEQUENCE: 11

Met Thr Pro Ala Gln Thr Asn Ala Thr Thr Val His Pro His Asp
1               5                   10                  15

Ala Lys Asn Gly Ser Gly Gly Ser Ala Leu Pro Thr Leu Val Val Phe
            20                  25                  30

Gly Phe Ile Val Thr Leu Leu Phe Phe Leu Phe Met Leu Tyr Phe Trp
        35                  40                  45

Asn Asn Asp Val Phe Arg Lys Leu Leu Arg Ala Leu Gly Ser Ser Ala
    50                  55                  60

Val Ala Thr Ala Ser Thr Arg Gly Lys Thr Arg Ser Ser Thr Val Val
65                  70                  75                  80

His His Val Val Pro Arg Ala Thr Thr Arg Val Val Leu Thr Ala Cys
                85                  90                  95

His Arg Thr Phe Phe Tyr His Pro Arg Pro Met Ala Val Leu Thr Thr
            100                 105                 110

Arg His

<210> SEQ ID NO 12
<211> LENGTH: 425
<212> TYPE: PRT
<213> ORGANISM: Human cytomegalovirus

<400> SEQUENCE: 12

Met Arg Gln Val Ala Tyr Arg Arg Arg Glu Ser Ser Cys Ala Val
1               5                   10                  15

Leu Val His His Val Gly Arg Asp Gly Asp Gly Glu Gly Glu Ala Ala
            20                  25                  30

Lys Lys Thr Cys Lys Lys Thr Gly Arg Ser Val Ala Gly Ile Pro Gly
        35                  40                  45

Glu Lys Leu Arg Arg Thr Val Val Thr Thr Thr Pro Ala Arg Arg Leu
    50                  55                  60

Ser Gly Arg His Thr Glu Gln Glu Gln Ala Gly Met Arg Leu Cys Glu
65                  70                  75                  80

Lys Gly Lys Lys Arg Ile Ile Met Cys Arg Arg Glu Ser Leu Arg Thr
                85                  90                  95

Leu Pro Trp Leu Phe Trp Val Leu Leu Ser Cys Pro Arg Leu Leu Glu
            100                 105                 110

Tyr Ser Ser Ser Phe Pro Phe Ala Thr Ala Asp Ile Ala Glu Lys
        115                 120                 125

Met Trp Ala Glu Asn Tyr Glu Thr Thr Ser Pro Ala Pro Val Leu Val
    130                 135                 140

Ala Glu Gly Glu Gln Val Thr Ile Pro Cys Thr Val Met Thr His Ser
145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
            180                 185                 190
```

```
Gly Leu Gln Tyr Arg Leu Pro Tyr Ala Thr Trp Asn Phe Ser Gln Leu
            195                 200                 205

His Leu Gly Gln Ile Phe Ser Leu Thr Phe Asn Val Ser Met Asp Thr
        210                 215                 220

Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
                245                 250                 255

Asp Glu Pro Cys Cys Thr Pro Ala Leu Gly Arg Tyr Ser Leu Gly Asp
            260                 265                 270

Gln Ile Trp Ser Pro Thr Pro Trp Arg Leu Arg Asn His Asp Cys Gly
        275                 280                 285

Thr Tyr Arg Gly Phe Gln Arg Asn Tyr Phe Tyr Ile Gly Arg Ala Asp
290                 295                 300

Ala Glu Asp Cys Trp Lys Pro Ala Cys Pro Asp Glu Pro Asp Arg
305                 310                 315                 320

Cys Trp Thr Val Ile Gln Arg Tyr Arg Leu Pro Gly Asp Cys Tyr Arg
                325                 330                 335

Ser Gln Pro His Pro Pro Lys Phe Leu Pro Val Thr Pro Ala Pro Pro
            340                 345                 350

Ala Asp Ile Asp Thr Gly Met Ser Pro Trp Ala Thr Arg Gly Ile Ala
        355                 360                 365

Ala Phe Leu Gly Phe Trp Ser Ile Phe Thr Val Cys Phe Leu Cys Tyr
370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Arg Leu Pro Thr Tyr Asp Ser
            405                 410                 415

Tyr Pro Gly Val Arg Lys Met Lys Arg
        420                 425

<210> SEQ ID NO 13
<211> LENGTH: 306
<212> TYPE: PRT
<213> ORGANISM: Human cytomegalovirus

<400> SEQUENCE: 13

Met Arg Ile Glu Trp Val Trp Trp Leu Phe Gly Tyr Phe Val Ser Ser
1               5                   10                  15

Val Gly Ser Glu Arg Ser Leu Ser Tyr Arg Tyr His Leu Glu Ser Asn
            20                  25                  30

Ser Ser Thr Asn Val Val Cys Asn Gly Asn Ile Ser Val Phe Val Asn
        35                  40                  45

Gly Thr Leu Gly Val Arg Tyr Asn Ile Thr Val Gly Ile Ser Ser Ser
    50                  55                  60

Leu Leu Ile Gly His Leu Thr Ile Gln Val Leu Glu Ser Trp Phe Thr
65                  70                  75                  80

Pro Trp Val Gln Asn Lys Ser Tyr Asn Lys Gln Pro Leu Gly Asp Thr
                85                  90                  95

Glu Thr Leu Tyr Asn Ile Asp Ser Glu Asn Ile His Arg Val Ser Gln
            100                 105                 110

Tyr Phe His Thr Arg Trp Ile Lys Ser Leu Gln Glu Asn His Thr Cys
        115                 120                 125

Asp Leu Thr Asn Ser Thr Pro Thr Tyr Thr Tyr Gln Val Asn Val Asn
    130                 135                 140
```

```
Asn Thr Asn Tyr Leu Thr Leu Thr Ser Ser Gly Trp Gln Asp Arg Leu
145                 150                 155                 160

Asn Tyr Thr Val Ile Asn Ser Thr His Phe Asn Leu Thr Glu Ser Asn
                165                 170                 175

Ile Thr Ser Ile Gln Lys Tyr Leu Asn Thr Thr Cys Ile Glu Arg Leu
            180                 185                 190

Arg Asn Tyr Thr Leu Glu Ser Val Tyr Thr Thr Val Pro Gln Asn
                195                 200                 205

Ile Thr Thr Ser Gln His Ala Thr Thr Thr Met His Thr Ile Pro Pro
210                 215                 220

Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
                245                 250                 255

Ser Tyr Val Leu Ser Gln Lys Thr Asn Asn Thr Thr Ser Pro Trp Ile
            260                 265                 270

Tyr Ala Ile Pro Met Gly Ala Thr Ala Thr Ile Gly Ala Gly Leu Tyr
            275                 280                 285

Ile Gly Lys His Phe Thr Pro Val Lys Phe Val Tyr Glu Val Trp Arg
290                 295                 300

Gly Gln
305

<210> SEQ ID NO 14
<211> LENGTH: 92
<212> TYPE: PRT
<213> ORGANISM: Human cytomegalovirus

<400> SEQUENCE: 14

Met Ala Arg Ser Val Lys Thr Ile Arg Ile Gln His Ile Tyr Ser Pro
1               5                   10                  15

Arg Ser Ser Asn Thr Leu Gln His Met Ser Lys Lys Gln Glu Ser Ile
                20                  25                  30

Ala Thr Ile Thr Phe Gly Arg Ile Thr Cys Cys His Pro Leu Ala Ser
            35                  40                  45

Ile Asn Leu Met Phe Asn Gly Ser Cys Thr Val Thr Val Lys Ile Ser
50                  55                  60

Met Gly Ile Asn Gly Ser Thr Asn Val His Gln Leu Val Ile Val Leu
65                  70                  75                  80

His Leu Gly Asn Arg Cys Gln Pro Trp Arg Gln Val
                85                  90

<210> SEQ ID NO 15
<211> LENGTH: 176
<212> TYPE: PRT
<213> ORGANISM: Human cytomegalovirus

<400> SEQUENCE: 15

Met Lys Pro Leu Ile Met Leu Ile Cys Phe Ala Val Ile Leu Leu Gln
1               5                   10                  15

Leu Gly Val Thr Lys Val Cys Gln His Asn Glu Val Gln Leu Gly Asn
                20                  25                  30

Glu Cys Cys Pro Pro Cys Gly Ser Gly Gln Arg Val Thr Lys Val Cys
            35                  40                  45

Thr Asp Tyr Thr Ser Val Thr Cys Thr Pro Cys Pro Asn Gly Thr Tyr
50                  55                  60
```

```
Val Ser Gly Leu Tyr Asn Cys Thr Asp Cys Thr Gln Cys Asn Val Thr
 65                  70                  75                  80

Gln Val Met Ile Arg Asn Cys Thr Ser Thr Asn Asn Thr Val Cys Ala
                 85                  90                  95

Pro Lys Asn His Thr Tyr Phe Ser Thr Pro Gly Val Gln His His Lys
            100                 105                 110

Gln Arg Gln Gln Asn His Thr Ala His Ile Thr Val Lys Gln Gly Lys
            115                 120                 125

Ser Gly Arg His Thr Leu Ala Trp Leu Ser Leu Phe Ile Phe Leu Val
            130                 135                 140

Gly Ile Ile Leu Leu Ile Leu Tyr Leu Ile Ala Ala Tyr Arg Ser Glu
145                 150                 155                 160

Arg Cys Gln Gln Cys Cys Ser Ile Gly Lys Ile Phe Tyr Arg Thr Leu
                165                 170                 175

<210> SEQ ID NO 16
<211> LENGTH: 100
<212> TYPE: PRT
<213> ORGANISM: Human cytomegalovirus

<400> SEQUENCE: 16

Met Cys Thr Asp Pro Arg Arg Thr Ala Gly Trp Glu Arg Leu Thr His
 1               5                  10                  15

His Ala Ser Tyr His Ala Asn Tyr Gly Ala Tyr Ala Val Leu Met Ala
                20                  25                  30

Thr Ser Gln Arg Lys Ser Leu Val Leu His Arg Tyr Ser Ala Val Thr
            35                  40                  45

Ala Val Ala Leu Gln Leu Met Pro Val Glu Ile Val Arg Lys Leu Asp
        50                  55                  60

Gln Ser Asp Trp Val Arg Gly Ala Trp Ile Val Ser Glu Thr Phe Pro
 65                  70                  75                  80

Thr Ser Asp Pro Lys Gly Val Trp Ser Asp Asp Ser Ser Met Gly
                85                  90                  95

Gly Ser Asp Asp
            100

<210> SEQ ID NO 17
<211> LENGTH: 117
<212> TYPE: PRT
<213> ORGANISM: Human cytomegalovirus

<400> SEQUENCE: 17

Met Arg Leu Ile Phe Gly Ala Leu Ile Ile Phe Leu Ala Tyr Val Tyr
 1               5                  10                  15

His Tyr Glu Val Asn Gly Thr Glu Leu Arg Cys Arg Cys Leu His Arg
                20                  25                  30

Lys Trp Pro Pro Asn Lys Ile Ile Leu Gly Asn Tyr Trp Leu His Arg
            35                  40                  45

Asp Pro Arg Gly Pro Gly Cys Asp Lys Asn Glu His Leu Leu Tyr Pro
        50                  55                  60

Asp Gly Arg Lys Pro Pro Gly Pro Gly Val Cys Leu Ser Pro Asp His
 65                  70                  75                  80

Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
            100                 105                 110
```

```
Ile Gly Val Arg Gly
        115

<210> SEQ ID NO 18
<211> LENGTH: 159
<212> TYPE: PRT
<213> ORGANISM: Human cytomegalovirus

<400> SEQUENCE: 18

Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
            20                  25                  30

Ile Cys Pro Leu Ala Val His Val Leu Glu Leu Glu Asp Tyr Asp Arg
        35                  40                  45

Arg Cys Arg Cys Asn Asn Gln Ile Leu Leu Asn Thr Leu Pro Val Gly
    50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Arg Leu Asn Tyr His His Phe Arg Leu Arg Trp
145                 150                 155

<210> SEQ ID NO 19
<211> LENGTH: 316
<212> TYPE: PRT
<213> ORGANISM: Human cytomegalovirus

<400> SEQUENCE: 19

Met Leu Arg Leu Leu Phe Thr Leu Val Leu Ala Leu His Gly Gln
1               5                   10                  15

Ser Val Gly Ala Ser Arg Asp Tyr Val His Val Arg Leu Leu Ser Tyr
            20                  25                  30

Arg Gly Asp Pro Leu Val Phe Lys His Thr Phe Ser Gly Val Arg Arg
        35                  40                  45

Pro Phe Thr Glu Leu Gly Trp Ala Ala Cys Arg Asp Trp Asp Ser Met
    50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln
                85                  90                  95

Leu His Gly Asn Gln Thr Val Gln Pro Ser Phe Leu Ser Phe Thr Cys
            100                 105                 110

Arg Leu Gln Leu Glu Pro Val Val Glu Asn Val Gly Leu Tyr Val Ala
        115                 120                 125

Tyr Val Val Asn Asp Gly Glu Arg Pro Gln Gln Phe Phe Thr Pro Gln
    130                 135                 140

Val Asp Val Val Arg Phe Ala Leu Tyr Leu Glu Thr Leu Ser Arg Ile
145                 150                 155                 160
```

```
Val Glu Pro Leu Glu Ser Gly Arg Leu Ala Val Glu Phe Asp Thr Pro
                165                 170                 175

Asp Leu Ala Leu Ala Pro Asp Leu Val Ser Ser Leu Phe Val Ala Gly
            180                 185                 190

His Gly Glu Thr Asp Phe Tyr Met Asn Trp Thr Leu Arg Arg Ser Gln
        195                 200                 205

Thr His Tyr Leu Glu Glu Met Ala Leu Gln Val Glu Ile Leu Lys Pro
    210                 215                 220

Arg Gly Val Arg His Arg Ala Ile Ile His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg
305                 310                 315

<210> SEQ ID NO 20
<211> LENGTH: 122
<212> TYPE: PRT
<213> ORGANISM: Human cytomegalovirus

<400> SEQUENCE: 20

Met Val Asp Gln Cys Cys Tyr Arg His Leu His Arg Ser Leu Ser Gly
1               5                   10                  15

Gly Pro Asp Val Leu Tyr Ala Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
    50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
        115                 120

<210> SEQ ID NO 21
<211> LENGTH: 642
<212> TYPE: PRT
<213> ORGANISM: Human cytomegalovirus

<400> SEQUENCE: 21

Met Gln Leu Cys Ser His Ser Ile Ser Ser Gln Arg His Val Ala Ser
1               5                   10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
        35                  40                  45
```

```
Thr Thr Arg Arg Phe Leu Pro Arg Thr Pro Ser Pro Ser Asn Thr Val
 50                  55                  60

Cys Cys Ile Arg Arg Arg Leu His Glu Arg Thr Ile Arg His Ser Met
 65                  70                  75                  80

Arg Cys Arg Arg Arg Asp Met Ala Ser Ser Ala Ser Thr Pro Val Ser
                 85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
        115                 120                 125

Asp Lys Leu Glu Ala Asp Ala Asp Pro Ala Leu His Arg Arg Pro Ala
130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Ser Cys Ser Thr Thr Cys Thr
            180                 185                 190

Pro Leu Ile Met Asp Leu Pro Ser Leu Ser Val Glu Leu Ser Ala Gly
        195                 200                 205

His Lys Lys Lys Glu Thr Pro Thr Glu Gly Gly Trp Gly Gly Glu Glu
210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Ala Ala Phe
        275                 280                 285

Ser Phe Ser Ser Thr Val Ser Glu Thr Gly Thr Phe Pro Gln Ser Thr
290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Gly Ala Leu Arg Gly Gly
            340                 345                 350

Glu His Glu Ala Ile Pro Lys Val Ala Ser Leu Phe Trp Thr Leu Leu
        355                 360                 365

Lys Ala Thr Gln Ile Val Glu Met Thr His Lys Thr Pro Ser Ala Asp
370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
            420                 425                 430

Arg Pro Gln Thr Ala Thr Ala Ser Thr Lys Ala His Thr Gln Gln Gln
        435                 440                 445

Pro Glu Glu Pro Lys Gly Gln Gln Ile Trp Thr Gln Thr Ala Gly Gln
450                 455                 460
```

```
Ala Ala Pro His Gly Asp Glu Pro His Ser Asp Gly Glu Leu Arg Arg
465                 470                 475                 480

Glu Ser His Ser Ala Pro Pro Thr Ser Arg Thr Leu Pro Asp Thr Ile
            485                 490                 495

Leu Ala Val Lys Arg Arg Ser Val Ala Gln Arg Ser His Val Arg Leu
        500                 505                 510

Asp Ala Lys Pro Gly Leu Asn Glu Arg Asp Gly Phe Arg Gln Arg Leu
    515                 520                 525

Leu Leu Pro Leu Ser Gly Tyr Phe Arg Ala Asn Glu Leu Arg Asn Gln
530                 535                 540

Gln Phe Met Gly Tyr Gly Thr Lys Asn Gly Leu Lys Asn Thr Trp Leu
545                 550                 555                 560

Thr Arg Pro Leu Gly Val Ala Gly Gly Val Arg Glu Thr Ile Gly Glu
            565                 570                 575

Arg Gln Asp Arg Asn Val Ala Asp Ser Ala Thr Gln Arg Val Phe His
        580                 585                 590

Thr Leu Tyr Ala Ala Leu Gln Thr Val Arg Val Trp Tyr Thr Ala Leu
    595                 600                 605

Gly Thr Ala Trp Arg Thr Ser Gly Ser Arg Thr Arg Glu Ser Leu Phe
610                 615                 620

Asp Gly Pro Arg Arg Arg Asp Arg Gln Ala Ala Arg Leu Arg Arg Leu
625                 630                 635                 640

Glu Leu

<210> SEQ ID NO 22
<211> LENGTH: 336
<212> TYPE: PRT
<213> ORGANISM: Human cytomegalovirus
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 22

Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Phe Arg Thr Leu
            20                  25                  30

Gly Thr Gly Leu Gly Asp Gly Gly Cys Ala Gly Arg Arg Trp Xaa Arg
        35                  40                  45

Xaa Val Ala Gly Thr Gly Ile Thr Leu Gly Thr Gly Thr Arg Gly Pro
    50                  55                  60

Gly Leu Arg Asp Gly Gly Asp Gly Gly Val Cys Gly Glu Asp Gly Gly
65                  70                  75                  80

Leu Leu Arg Arg Gly Arg Gly Leu Ala Gly Pro Ala Val Ala Gly Val
                85                  90                  95

Cys Gly Asp Gly Gly Leu Leu Gln Arg Arg Gly Leu Arg Gly Gln Glu
            100                 105                 110

Cys Ala Xaa Pro Gly Gly Phe Ala Gly Gly His Gly Thr Gly Gly Gly
        115                 120                 125
```

```
Gly Asp Ser Thr Asn His Thr His Thr Gln Leu Thr Ser Ala Val Ala
130                 135                 140

Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
                165                 170                 175

Ser Asp Met Leu Leu Arg Leu Cys Thr Ala Ala Asp Thr Ser Gly
            180                 185                 190

His Arg His Leu Pro Pro His Met Ala His Val Leu Arg Arg Pro Ala
        195                 200                 205

Ser Tyr Val Val Cys Ser Gln His Gly Ala Phe Phe Pro Ala Arg His
    210                 215                 220

Leu His Arg Thr Pro Ser Ala Ala Phe Ala Val Ala Ser Thr Arg Glu
225                 230                 235                 240

Gln Tyr Ala Thr Ala Cys Ala Val Ala Ala Thr Trp Pro Pro Arg
                245                 250                 255

Leu Pro His Leu Phe Arg Thr Pro Asn Leu Trp Leu Pro Thr Thr Asp
            260                 265                 270

Val Gln Gly Ser Arg Thr Arg Arg Pro Ile Pro Ile Leu Gln Arg
        275                 280                 285

Pro Arg Pro Pro Ser Gln Thr Ser Trp Lys Pro Thr Gln Thr Gln His
    290                 295                 300

Ser Ile Asp Ala Arg Pro Arg Cys Cys Ala Thr Ser Ser Ser Pro Ala
305                 310                 315                 320

Thr Pro Asn Ala Ala Leu Pro Thr Glu Pro His Pro Arg Gly Leu Pro
                325                 330                 335

<210> SEQ ID NO 23
<211> LENGTH: 11950
<212> TYPE: DNA
<213> ORGANISM: Human cytomegalovirus

<400> SEQUENCE: 23
cctcgccatg aggatcgcga caggcgcgtc gaggggggcag gaacacccctt gcggattgac    60
attcttggtg gtgtttcgtt gttgtcggta gttgttgttg acgatgagga taaataaaaa   120
tgaccttgtt tttgttctgt tttctcttgt tgggaatcgt cgactttgaa ttcttcgagt   180
tatcggaaag ctgaggtacc caaatgtctg tagcttttttt cttttacccc tcttgtttat   240
catctgcgat tcgtggtagg taggagaggg aaatgataat ccgagattaa ggaaaggaga   300
agataaaaaa taaaaaaaaa taataaaaca gaagccgacc ggccgccgac ccgttcccca   360
ggaccagcct acgaggaacg gataacgcgc tggcgacggc agcggtggtg gcgctggggg   420
tggcggcagt ggtactgctg atggtagtcg ggacggagga gaggcgatgc atacatacac   480
gcgtgcatgc tgcatgggtg gatggtacgg ccgggagacg cggaagagaa actcacataa   540
aaaggtgaca aaagagcgg ttgaaaaaag aaaacaagat tcgaccagac agaagagaag   600
gaccgggggct tggcgaccct tccacgactg ctgttgtcat ctcggctcct ccgtcttctc   660
ccggccacgg gcggctaagt caccgccgtt ctccccatcc gtccgagcgc cgaccgacca   720
gccggccgat tcgcccgccg gggcttctgg agaacgccgg ggcagcagcg atctggggaa   780
gctgctaaac ccctgcgttt ttatatggta gctctgccga gcgcgggctg acgcgttggg   840
taagcggaaa gacgtgtgtg acgaaaaggg gtcccatggt atttcacgtg acgatgagga   900
gatacggttt ggagcacata cggtttagaa aaagggagtt gtcgtgacaa gggctgaggg   960
```

```
acctctgtct ccatgtgtgt ataaaaagca aggcacgttc ataatgtaaa aaagaacacg    1020
ttgtaaacaa gctattgctg tatcattcgg ctgactatgc ttcattcgga ctgattttct    1080
tttcctaacg gcgtaactta aagtgattaa cgtatgatat ttgttcccca gagttatact    1140
atagtcatca tcctaaaatt cagatataaa tgaacacatg tcgtatggga ttattaagaa    1200
accgaaactc tccacagttc accatcttct tcgtcattca accgatgacc cactccgtac    1260
aacgaatcag tctgctgcgt catattgcaa agcacaagcg acgtatgcga acaacttgaa    1320
acacaggctg ttgtattgac gaccgttgta ccattattag tcaccaccgt tatcccatgt    1380
ttcccacccg atggaaaacc gtcttctatc atcaactgtg gtaagatttc gaccctgcga    1440
ggtattcagt ttcctcatat ccataacctg gattttatca ttaaacccca atattaaaca    1500
cttttttagt acccccccacc caccaaaaaa tgtgactgga ccggttccta gcagctctgg    1560
gagccatgtt caggttgaac cacagctaca gcgaaaccga gtccagtgac cggtaaccac    1620
gtccagcccc tgcgtatgta ccagtccaag cacgtccggt cattgttcta cacaggaaat    1680
ctaactaggt caacgcaatt ttattccacc gttacgcaga atactaacaa aaaaacacac    1740
aaatttaacg aattacacgt agtttattac atgaaaactg taagaacacc aattcactaa    1800
gcgatacaac atttagctga cttccaagtg ccacacatca ccactgtatt catccatgtt    1860 ttaccgaac caacgagaca gatcgaagaa gccagaatct cccgacttta aattacataa    1920
atccaacgta ttatgaccac agctcgacac acaaatagtt gcgttactat tcacagtagc    1980
attacctata cccgtaacgt tgcacaacca ctgatcacca ttgttaccaa aaacggtttt    2040
ccacttagtt gtcaacggat cttttcctatg cgtaatggta aaattactac cagtcgtcgc    2100
ttttagctca ttacgagtat tatccgcatc cacatatatc aacgtcatag ctaggcacgc    2160
tataagtacc cccccccac aatggaatgt tgccaaaccg gttctttccc gttatagcca    2220
tagcgttccc aggcaaaagc aaacgccaaa cctaatgcag tgaaaagcgc ttgcagccag    2280
aaccagctta tgtaccagcc acaatcacat ccggttattg tttccacagg aaatcctacc    2340
aggcaaagcc ccgcttgttt tgttcctatc ttgtttagca attcgtaaac tgtcagccta    2400
gcgacgtccg tttagatcaa aagtcacgta tatagcgacg ctgtttccat ccgtttcccc    2460
gtcccgccgt ttccgaacaa cccacccggg ttcagacaac cgaccaccaa cagaaatata    2520
cacacagacc actgggagtt cagttaaaga tttcatcagg tttattttgg ctgctgctag    2580
tcttttgctt cttagaaaaa aaatacccat atagagaaat aatgatagtt tgacaacaca    2640
tatggcaggg atttcttctt catcaataag atatgcaatt cccccaggga gagactttca    2700
acaattgaat ttacaaaaac aaaattacat caggagaaag agaggataca ttaataaata    2760
tattatatct ggtgtatata ctgaatgctg ctggttcata aggtaacgat gctacttttt    2820
ttaattccaa gatggttttt ctttgttagt cttttgttga cttgctggtt cctaaaagtt    2880
cgcaaaaacg attgtgtgaa gattttatga cgttggttga ctagttcatg agattctgct    2940
gtacgtgtga tggttattcg ctggttcgtt ctaagatgag tatcgtactg tgtctgcgat    3000
ggtcgtctct tactggcatt ctctcggctg cctcttgctt tcatgattga aaaggaaaaa    3060
aggactccga gggcgcggtc atctttact tttcggtttt ctcgttggcg ggtcagaggt    3120
agtcagatca tgagactgtc gtggtcgatg aaactgtgtc tgctcaagtg acgtccattt    3180
cttgtacgga gaaaaagtc atcgggataa ataaggctat acaaggcgtt gtcaagcgtg    3240
cggctctaaa caaattaagc gatacaaaat tacagtaata cgaataataa attaccccccc    3300 tccccctgtg gtcccccgag acgagagcca cccatcgtgt actctcgcac cacccacgac    3360
```

```
cacagaggga gacgggacga agagacgacg cacagcgcca tctcctcctg gaggccggcg    3420
acgttaactg ctacagctgc ggcggcgaag acagctgcga tttgtcggcc gacatgccga    3480
tggtatgggc ggcggcggca atggccgcgg cagcggggag gagaggagag agaagaggag    3540
cggggcgtcc gaaggcgagg atggcatggt ctcgccggag cgcccggctt ttatggaaca    3600
ctcgcgtccg gttgggtatc acccacagga agatgagtca caacttccaa accatcttga    3660
gacccgagta acggtttaca ggtcgcacgc cagtcagcta aaaacagcgg acagtcccac    3720
gctgtttctt ttgtggctct ctccagtttc ctcatcaccg tcccggtctc cgtcgtcatc    3780
ggaagaatac cacccgctct catgcggcag tcgatcggcc tcgacgaacg agacgcggcg    3840
acgcctctcc acggccgact ggttgtggtg gtgaaagaag agcaccagca atcccaggag    3900
gagcaacaag ccctcacatg tccaggaggt cggggagagg gcctgtcgga gatggccgtg    3960
aggcatcacg tacggcagct gaggagaaac ggagaagaaa ggaaaattac cgtcaggggc    4020
cggggttctt attagagaaa cagcacgtag gtcaggatcc agatgctaat ggcaatcatg    4080
atgacgatga tcatgcaggc caagacgcgg cgcaccaatg ccgaatccaa tagccgccgt    4140
gcctccggtt ggtggccggc ggcatctaga gacatgattt gggggggacc ggcggcgcaa    4200
aaagacaggg agatggacag tgtcacggtg ttttgttata attaggacat ggggaccgga    4260
agccgagaca gagtactaca gggtgttgaa gggtaacgtg agggagatca tgtcatgggc    4320
gggctgaaga ccgtgcgggg aggattgacg tgtgcggtgc ttgtggaaca cggtgtttta    4380
atatgtatcc gcgtgtaatg cacgcggtgt gctttctggc actcagcttg gtaagctatg    4440
tggccgtctg cgccgaaacc aaagtcgcca ccaactgtct cgtgaaatca aagataccc    4500 atttgacgtg caagtgcagt ccgaataaca catcatctaa taccggcaat ggcagcaagt    4560
gccacgcgat gtgcaaatgc cggatcacag aacccattac catgctaggc gcatactcgg    4620
cctggggcgc gggctcgttc gtggctacgc tgatagtcct gctggtggtc ttctttgtaa    4680
tttacgcgcg cgaggaggag aaaaacaaca cgggcaccga ggtagatcaa tgtctggcct    4740
atcggagcct gacacgcaaa aagctggaac aacacgcggc taaaaagcag aacatctacg    4800
aacggattcc ataccgaccc tccagacaga aagataactc cccgttgatc gaaccgacgg    4860
gcacagacga cgaagaggac gaggacgaca acgtctgata aggaaggcga gaacgtgttt    4920
tgcaccatgc agacctacag caccccctc acgcttgtca tagtcacgtc gctgtttttg    4980
ttcacaactc agggaagttc atcgaacgcc gtcgaaccaa ccaaaaaacc cctaaagctc    5040
gccaactacc gtgccacctg cgaggaccgt acacgcacgc tggttaccag gcttaacact    5100
agccatcaca gcgtagtctg gcagcgttat gatatctaca gcagatacat gcgtcgtatg    5160
ccgccacttt gtatcattac agacgcctat aaagaaacca cgcgtcaggg cggtgcggcg    5220
ttcgcgtgca cgcgccaaaa tctgacgctg tacaatctca cggttaaaga tacgggagtc    5280
tacctcctgc aggatcagta taccggcgat gtcgaggctt tctacctcat catccaccca    5340
cgtagcttct gccgagcctt ggaaacgcgt cgatgctttt atccgggacc agggagagtt    5400
gtggttacgg attcccaaga ggcagaccgg gcaattatct cggatttaaa acgccagtgg    5460
tccggcctct cactccattg cgcctgggtt tcgggaatga tgatctttgt tggcgcgctg    5520
gtcatctgct tcctgcgatc gcaacgaatc ggggaacagg acgctgaaca tctgcggacg    5580
gacctagata cggaaccttt gttgttgacg gtggacgggg atttacagta aaagatgcgt    5640
gtcgcctgcc gaagacctca ccatctcacg tacaggcata cggcgtatac aatcataata    5700
```

```
ttctatattc tgcatagagt tacatgcaac agtactacta ccaatactgc atccatcaca   5760
tcacccaaca ctgcttctac caccttttgtg accagcgtat tttctactcc gaataacaac   5820
acatcaacga cgccacacac atctgtcacc tcacaagcgt caaccattgg caacatcacc   5880
aacgttacct ccgacttgag tactttcaca accgtatatt ctacattcaa tacatcatat   5940
gctaatatat ccaatacggc tgccactaca gaattgattt caacaaatac caacactata   6000
ttatctttta ccaacgtaac agcaaacgct acatcatctt ataacacaac aatcaccgta   6060
actatcacgt cagatgaaac ttcgcacaac gtatccacta tactgcact tataagcacg    6120 ccatggctta caaattgcag cgccacaacg tacaccacgt acaaccgtac taactcttcc   6180
aacgcttgtc acacagagac aacaatcata cgtttcaaag aaactaatac aacaggaata   6240
gaagggagta atgtcaccat aaaaggtaat tctacgtggg attgtctttc agtcgcctgg   6300
atacgacatt acaatcgatc cacacacgga catcatctag gtcatcgtaa gaacgcacat   6360
acccaatctt ggtattggtt acgcatcctt acctctcata ctgtatgtca ttctcaacat   6420
gaaagacctt cactgtacca tgacttatgt cgttcgtgca acaacacaga actacatctg   6480
tacgatctaa atatcaccaa ttccggcagg tacagcagag gttgttttaa agaaaattac   6540
ttcacaggac atcacgaaga tgaaaatttc tacctattag taacaccaaa aaatcatact   6600
gaagctatta atgctacttt cgtttgccct agatacaaca ccgatatcga aaatgaagat   6660
agagagaaag gaagtcaaca tactaacaat acacatcacc acaaacgtaa tctctatcat   6720
agctcgcaaa aagccgcac cgtatggacc atcgtgttgg tttgtatggc ctgcatagtt   6780
ctgttttttg cacgacgagc ctttaacaaa aagtaccata tgttgcaaga caccgtcagt   6840
gaatcagaat tcattgttcg atatcacaca gaacatgaag attgagctac gtttccgggc   6900
agacatctta tgaagctgaa caataaacta aaacattctg taaggctcag cgttcaaagg   6960
aatattaatg cccattgagc gagaactaat attgcaatgg actggcgatt tacggttatg   7020
tggacgatac taatatccgc gttatcagaa agctgcaatc aaacctgttc ctgtcaatgt   7080
ccctgtagta ctaccgttaa ctattccact agtactgaga cagccacatc aacatacagt   7140
acaacagtta tcagcaataa aagcacttca gaatctataa attgctctac tgcaactgca   7200
ccagcaacca ccgtttctac aaaaccgtcg aaaacaacca cacagatatc cacaacgaca   7260
aatacaaacg ttgagactac cacatgtacc aacaccacca cgaccgttac ttgtgatggt   7320
ttcaattata cagtccataa aagatgcgac cgcagttacg aggtaatcaa cgtaacagga   7380
tacgttggtg gcaacataac tctaaaaaat gcaatcagac tgagaaatgg cacaatgtag   7440
actggattca ttatgagtac cccacgcata aaatgtgcga attaggcaac tatcaccaaa   7500
caacaccacg gcacgacata tgttttgact gcaacgcac ctccctaact atctacaact   7560
taaccacaag aaacgctgga aaatatacca ggcatcaccg tgataacggt caagaagaaa   7620
attactacgt aacggtgtta attggagaca caacgttatc cactcttggc acatgccctg   7680
taagatataa agaatctagg aacactgaaa acaccattgg aagtaacatc ataaaaacca   7740
ttgagaaagc taacattccc ctgggaattc atgctgtatg ggcaggcgta gtggtatcag   7800
tggcgcttat agcgttgtac atgggtagcc atcgcattcc caaaaaaccg cattacacca   7860
aacttcccaa atatgatcca gatgaatttt ggactaaggc ttaacatgca catcaataaa   7920 cttttttttaa ccaataacat gtctctgttt ttttttgtta acaacctatg atataaagcg   7980
gtatattcaa tcattactaa acaaaaaaac atgggcatgc aatgcaacac taaattgtta   8040
ttgccagtcg cactaatacc ggttgtaatc atcctaattg gtactctagt gcccatactt   8100
```

```
ttacatgaac aaaaaaaggc gttttactgg cgacttttc tgcaaagtca acatgtagaa    8160
gcacccatta cagtaacgca gggagacaca gtctacctag atgctagcaa taatccctgt    8220
aattattcca gcttttggta ccacggtaat tgcgaacttt gtggatggaa cggatatcta    8280
cgcaatgtta cacattacta cacaaacaca tcgtgttccc cgcaattcat gtgcataaac    8340
gaaactaaag gtctgcagtt atataatgta acattaaacg attcaggtgc ttatactgaa    8400
cacgtttacg aatgtgatct ttcatgtaac attactactt ataacgaata tgaaatactc    8460
aattacttcg ataactgtaa ctacaccata aatagcacca agcatattat caccgtggtg    8520
tcttcacgtc attctaaaca aacaaattcc cacgtatcca ctcacgctgg ttgggcagcc    8580
gccgtggtga cggtaattat gatctacgtt ttgatccact ttaacgttcc ggcaactctg    8640
agacacaaac tacgaactag aaacaacgta atcgcatag cgtgattaca agtatcgac    8700 actaatttat ccaagataaa atttgattac tccgtgcggt tctcaaaaac tgtaaggtcc    8760
cgcttttcta ctccatcatg aaggatcgca atagaatact gctatgtatc atctttattt    8820
gcatcatgtg cctcatttgt atttacttta aacgtcgttg tgttcttact ccgtctccag    8880
acaaagcgga tctgcgagtg gaatttccct cgttaccccc gtgtatcggc atacaatgtg    8940
ctgcatgaga acacgcgtga cacatagcgt acccctggac ggtacagttt atgataacgt    9000
cattcagggg aagtatacat tactatcgac gtgttatcac agaacacaca gattttctgc    9060
gtgttttata aaagagcgtc tcgaagcagc ttgagccaca ctacggtcca gatgacgagc    9120
gtaatcaaaa atatgccgcg cagtagtcga aagccgtact gagcgtgcga ggcgggtagg    9180
gtgccgaacg acggatatgc gtcgttgtca tcttcgacta taaggatcgc gaccgagtct    9240
tcggccatgg taaacgtcac cctgtgtggc tggtatcgtag cgtatccggt ttggaattgt    9300
tctgctccag ctcgggggat agtgaggaat tctcaaggga tacgggaccc aatgactgga    9360
taagagaagg gttttttcccc gtaagatgat cctcgtatca catgaggtct ggatatgtat    9420
aaatgaagag tgaaataggc acagggaatc agatgccagc ctcgtgatgc agccgctggt    9480
tctctcggcg aagaaattgt cgtctctgtt ggcttgcaaa tacatcccac cttaagcgat    9540
gagtccataa agcaccgttg tccgggtacg gtgaaagtga ctcggattgt agcacgtccc    9600
ttttttttgt tttgtatcg cttatcgcca ctgacagtgc aatattttga tcgtgaggct    9660
gagtatggtt atgatgctta gaacgtggag attattacca atggtactac ttgccgcgta    9720
ctgttattgt gtttttggga cttgttcaat cggcacgacg actgctcccg tggaatggaa    9780
gtctcccgac cgtcagattc ctaagaatat tacttgcgct aactactcag ggaccatcaa    9840
cggcaacgtt acatttcgag gtcttcagaa caaaacggaa gacttttttgc actggttgtt    9900 agggtggggt cataagtcca tctgttcgtt cttcccgaaa ctccagggca actataacga    9960
acaacattac agatatgaag tagcgaacct gacgtataac tgcacctata accgcttgac    10020
gttgctaaat ctgacgacgg aaaacagcgg aaagtactat tttaaaaggg aagatgcgaa    10080
tttcaccttt tattactctt gttacaacct gaccgtgtcc taaagaacgc acgtgaagtt    10140
ccacagagcc gcgtggctgt agctattgtg tttacgttgc ttttgaaatg ttaagcgtcc    10200
ctacggcgct aacatgtttc taggctactc tgactgtgta gatcccggcc ttgctgtgta    10260
tcgtgtatct agatcacgct taaagctcgt gttgtctttt gtgtggttgg tcggtttgcg    10320
tctccatgat tgtgccgcgt tcgagtcctg ctgttacgac atcaccgagg cggagagtaa    10380
caaggctata tcaagggaca aagcagcatt cacctccagc gtgagcaccc gtacaccgtc    10440
```

```
cctggcgatc gcgcctcctc ctgatcgatc gatgctgttg tcgcgggagg aagaactcgt   10500
tccgtggagt cgtctcatca tcactaagca gttctacgga ggcctgattt tccacaccac   10560
ctgggtcacc ggcttcgtct tactaggact ttttgacgctt ttcgccagcc tgtttcgcgt   10620
accgcaatcc atctgtcgtt tctgcataga ccgtctccgg gacatcgccc gtcctctgaa   10680
ataccgctat caacgtctcg tcgctaccgt gtagctagtt agccagctgt gtatagtttg   10740
ttgtgttttg cttttgcata tttgttttca gtcagagagt ctgaaacggg gtgggaggga   10800
cttttacggg taatgcatgc taagatgaac gggtgggctg gggtgcgctt ggtaactcac   10860
tgtttgaata cgcgctcacg cacatatgta gcactcaaca tgttagcttt tgcccgcacg   10920
ccccggggcg tgccgagctg ccttttttaat aaagtctggg tttccagata cgcgctggtt   10980
ctgattttga tggtttgtgc ctctgaaagc tctacgagct gggccgtgac atccaatcga   11040
ctgcctaact gtagcacgat aactacaaca gcgggtcaag acgctgaatt gcacggtccg   11100
gcaccgttaa gctgtaatgt gacccagtgg ggacgttacg agaatggaag cacaccgta   11160 ttatggtgca ctttatgggg atcacgcacg cgagtctcat taggacaccg tgtagcgttt   11220
ggctgttctt ggaaaacatt tttttatttat aacgtttctg aaagtagtgg tggcacttat   11280
tatcaaaaag gttacaactg caccgacaaa catataacac tatcttgttt caacctaacg   11340
gtggttcctc gagcggttca aagcacaacc accgtaatga cacccacggt ggttacaaac   11400
tccacattca gtgtgtcact tgttgcgtcg agactgacga caaattccag cgcgtttaga   11460
cacgctagtt atcaacggca acagcgtgtc ggaaacggga cgttatccaa gaacataact   11520
aacttggcat tcacctacgg cagctggggc gtcgcgatgc tgctgttcgc cgccgtgatg   11580
gtgctcgttg atttgggttt gcctcaatcg gcttggcgac gctggcgaag ccacgtggac   11640
gatgaagaac gtggtttgtt aatgtaggaa ataaaaggca ctgtttgagc atgactgttt   11700
ccaaaccgta acgtggtaaa taaatcatgg cttccgacgt gagctcccat cttctaacgg   11760
ttacacaatc ccgttggaca atacatcata tgtacaataa actgttgatt ttggcgttgt   11820 ttaccccccgt gattctggaa tccatcatct acgtgtctgg gccacaggga gggaacgtta   11880
ccctggtatc caacttcact tcaaacatca gcgcacggtg gtttcgctgg gacggcaacg   11940
atagtcatct                                                           11950

<210> SEQ ID NO 24
<211> LENGTH: 14078
<212> TYPE: DNA
<213> ORGANISM: Human cytomegalovirus

<400> SEQUENCE: 24
cggtctggca gcgactggaa cccggacgcg tagccggcgg cgccgcgcgt catcaaaaag     60
tgcaggaact gttgcagcgc ttgggtcaga cgctaggcga cctagaactg caggaaacgt    120
tggcgacgga atactttgcg ctgttacacg gaatccagac cttcagctac gggctggact    180
ttcggtcgca gttggaaaag atccgcgatc tgcggactcg ttttgcggaa ctggccaagc    240
gacgcggcac gcgtctctcc aacgagggag tcctgcccaa cccccggaaa ccgcaggcga    300
cgacttcact gggcgccttt acacgcgggt tgaacgcgct ggaacgacac gtccagctgg    360
gtcaccagta tctgctcaac aagctcaacg gctcatcgct agtctatagg ctggaagaca    420
ttcctagcgt gcttccggca acacacgaga ccgaccccgc gctgataatg cgcgaccgcc    480
tgcgtcgcct atgcttcgcg cgtcaccacg acacttcct tgaagtggta gacgtcttcg    540
gcatgcggca aatcgtcacg caggccggcg aacccattca cctggtcacc gattatggca    600
```

```
acgtagcctt taagtacttg gcgctgcgag acgatggtcg gcccctggca tggcggcgcc      660
gctgtagcgg cggaggactc aagaacgtcg tcaccacacg ttataaagcc atcacggtag      720
ccgtggccgt ctgtcagaca ttgcgcactt tctggccaca gatctcgcag tacgacctac      780
gaccctacct cacgcagcat cagagccaca cgcaccccgc ggagactcac acgttgcata      840
accttaagct cttttgttat ctggtgagca ccgcctggca ccagcgcatc gacacgcagc      900
aggagctgac ggccgccgat cgcgtaggca gcggcgaggg tggtgacgta ggggaacaga      960
gaccgggccg cggtaccgtg ctgcgcctga gtctgcaaga gttttgtgta ctcatagcgg     1020
ctctgtaccc cgagtacatc tacaccgtcc tcaaataccc ggtgcagatg tcactaccct     1080
ccctcacagc tcacctacat caggatgtga tacacgcggt agtcaataac acacacaaaa     1140
tgcccccga ccacctcccc gaacaggtca aggccttctg tatcaccccc acccaatggc      1200
ccgccatgca gctcaataaa ctgttttggg aaaataaact ggtacagcaa ctgtgccagg     1260
taggcccgca aaaagcaca ccgcccttag gcaagctatg gctctacgcc atggccacgc      1320
tggtctttcc acaagacatg ctgcagtgtc tgtggctaga actgaaaccc cagtacgccg     1380
agacatacgc ctcggtgtcc gaattggtac agacgttgtt tcagattttc acgcaacaat     1440
gcgaaatggt gaccgagggg tacacgcaac cgcagctccc caccggagag ccggtgcttc     1500
agatgatccg cgtgccacgt caggacacaa ccaccacaga cacaaacacg accacggagc     1560
cgggactttt agatgttttt attcaaacag aaaccgccct agactacgcg ctgggctcct     1620
ggcttttcgg catacccgtg tgtctcggcg tgcatgtagc cgacctgctg aaaggccaac     1680
gtatactagt agcgcgccac ctcgaataca cgtcgcgaga ccgcgacttc ctccgcatcc     1740
aacgctcccg ggatctcaat ctcagtcaac tgctccagga cacgtggacc gaaacgccgc     1800
tggagcactg ctggctacaa gcccaaatca gacggctacg cgattacctg cgtttcccca     1860
cccgcttaga gtttattccc ctagtcattt acaacgcaca ggaccacacc gtcgtacgcg     1920
tgctgcgacc gccctccacg ttcgaacagg accacagtcg gctggtgttg gacgaggcct     1980
tccccacctt cccgctgtat gaccaagatg ataactcatc cgcggacaac atcgctgcgt     2040
ctggcgccgc tccaacaccg ccggtacctt tcaaccgcgt gccagtcaat attcagtttc     2100
tgcgtgaaaa cccgccaccc atcgcgcgag ttcagcagcc gccgcgccga catcgtcatc     2160
gagcggccgc ggccgcagac gacgacggac agatagatca cgtacaagac gatacatcaa     2220
ggacagccga ctctgcatta gtctctaccg cctttggcgg gtccgtcttt caagaaaacc     2280
gattgggaga acaccacta tgccgagatg aacttgtggc cgtggcgccc ggcgccgcca     2340
gcaccagttt cgcctcgccg cctatcacgg tgcttacgca gaacgtcctc agtgctctag     2400
aaatactgcg gctagtgcga ttggacctgc gacaactggc gcaatccgta caggacacta     2460
ttcaacacat gcggtttctc tatcttttgt aaccgacact gacagtagcg ggtaataaaa     2520
acaataggat tttatcgtt tttttatgtt acaaacaac gtatcacttt cacggtgatt       2580
tattcttgct attcctttc cccttgggct gtcagcgccg ggtgcgcgac acggctacca      2640
tgcgcaacag gtccagctta aggcgcact tgtcattaaa caggctggac atgcgcgtgt      2700
acttgctcag catggtggcc aacaccgggt gggtggcctc tgatatctcg gtcggcagct     2760
ccaaaacgac gttaacgacg tgacggtgtt tttcgtcccg cttgttggcc accgtgggtc     2820
ccggcgcggt gttagacatg gggcaggccg tgggggagg acgaagagga agccgctgct      2880
aaaccgccgc gcgcctgctg cacaatgtgg ccgccgacgt ggcaggcggt ctgtttaacc     2940
```

```
agcgcgcagc cccgacacag cggggcgccg tcctcgcttt ccaaacagct gtcgcggtac    3000
tcgcccgtct gacagcgcgc gcacagcagg ccgtgcccgt gcgaagtgag gcgcaggaga    3060
cgcgggaccg tcacgtcgcg taccaccaca gtggagtcgc aggtgcgtgc cgcgcagggc    3120
agaatgacgt cgaaagccag ccggtgatcg tacacggcac aagccgcgtt gaggcccagc    3180
acggctttcc agcccacgcg tacgcagcgc tgtccaaaga gcgtctcgga gacgagctcg    3240
tagacgcgct gccgcaccac ccgctgactg ccgcagagcg agcagtgcac gagctcggcg    3300
tgcgtgttga agatgacgct ctttcttga cggtcccgat aatagaacat cgagttgagc    3360
ggaaagtttt gctggcagtg tagcttttcc ttacccaggt tgaggcagtg tccgcactgc    3420
cgacagacca cggccaccag cgagcgcgcg tccagatggc gctcgcactt gagtcgacac    3480
agacaccaga gcggcaggtc gatgacgctg ccgatgaggc cgccgcgcag cgcggcgctg    3540
agtgcaaaga ggacgatctt ggtgggctct acgtgacgcg cctgctgtcc ggcgcccgcg    3600
tgtcctaccg ccgcagctgc cgccgtcgag cctcctccgc gcgtctcgtc gtgcagaccc    3660
agtgcccgca acggcaccag gtatcgcgga cacgtgtcgc aaaacgtctg caccgcttgt    3720
cgggccagta cgtagagcgg gttccgcag ggtaccttcc cggcgtaccg gcgcaaggct    3780
gcgatgaggc cccgcaactg cggcgaccgc ggctgccgtt ggtgacacca ctggttacgg    3840
tggtatacgg ccaaatcagc gcgggcgtcg aagcgcttgg cgcgtagtaa tgctaggcac    3900
ggcgagctgg tggggtgaag cacgggcagc cgaaggtcca ccccgaaaag gaaacggtga    3960
aggtcaccta gcagcgaggc ggtgacaccg tccaacaacg cgtgcagccg ctcgggcggg    4020
tagagccgca gacggcgcag caggtagtcg gtgtcgtagc gttcgaaacg cagaaaggcc    4080
atcgtgcgga cggccacggt gtgcagacag tccatgctgt agacgtaagc gagaaacaca    4140
aagtagggct tggtcataac catacgctga aagagcgccg tcaccgcctc ccgctcggct    4200
tgccgacaca ccagccattc gcgcaggaag cgttggtaga gacggtcgcc cagctcgcga    4260
ttcagaaagc gcttatccgt cacgaagaga tgaaggacgc aagaacgtgg cacgtgatgc    4320
accagctgct gctggaggac cgccgacgtc tgcgccgcaa actgcgccgg tggctgcgac    4380
gtttctaccg ccgcttcctc cggctgcagc gcaccgcggc cgatcaccag ctgcacatgg    4440
aaatggtcct cgtgaacgca gagggggcgcg aagagacggc gcagagcctg gtggaactca    4500
tcagtcgcgg tgtgcggagc gtgtcggaga cgacgactgg ccatgaccgc ccacagcag    4560 agccagcacc agcagaagag ccagcaccag cgggcccaga gtcgcaaagc gcgcgggcag    4620
ccacggccca gactgcggtc gcgatggccc ggagcgcgct cgccaccacg atgacggtgc    4680
ccaacgataa ccagtccgct ccaaggacgg cgcgcacggc ggagacggcg gatgacggtg    4740
atgggtcgac accctcgcc gacgactcac gtgctcctcc agaggccgac gcgcggaccc    4800
tccgacgtcc tggcccgccg ctgccgctgc cgccttccct tctcccgcca gagccagcaa    4860
ctcctcctcc tcttcatcag cgtctccctc gcttgcgcat ccgcatcgtc ccatacaggc    4920
ctcacaacga cacagccgcc acgaccccgc cgccatgggt ggcggcggcg gccgaggccc    4980
ggcagcggcg ccgccagcgg cgaccatggt gggagagcaa ctcggatgac gaggaggagg    5040 aggggagat gcggtccgag aggaccgctt tcccgccgtt cgcgtaagcg cggccgacat    5100
gcgggcgcgc cacagggacg gaccgctgcc gctgtgactg cttacggtga cgtggttccg    5160
gaccgccaac gacgtcgacg cggctttctt ggcgtacagc tcgcgcagca gattctcgta    5220
ctcgccctcg ttttcgggtc cgaaggcgat gagctcgatg ttgaagaccg acgccgaatt    5280
ggatttgcgc accacgcact tcgtcagcac tccgtaggcc gagggcttga tctcctcgat    5340
```

```
gtccttgagc gtgacgatga gcgactcgtt caccttaagc acattgaact cacctacgtg   5400
gcgcgccggc gaaacgagct tgacgggcgc tcgtacaaaa cagcagaggg agacggcgca   5460
gccagtgttt ttaaagataa acaaggcac gtggtctgtg cggctctccc agtagctgag    5520
tagatactcg acacaataga ccgtgtctgt cttgagcatg gcgtcgcaca ccgagtaatt   5580
ggggttttta cagatgaggc cggcatcggt gacgcgcagc tcgctgggac ccaacttgag   5640
gatacgccgc gtggcctgca ccagatcctg atggagaacc ttgttcatct ccatcgcacc   5700
gacgccaccg ccgatttatt tacccggcgc cgactcgtct tttccctcca ggattccgtt   5760
aatgtccatg agcttgctga cgatcgccgt taatagttgc gtcttctcac ggaggatctc   5820
tccgtgactg caggtcgcgc agtcgccgtg cacgtacttg aggaaggcgg cgtacttctg   5880
acccgcgttc acgaaattta agcgcgcgtc cagagagggc agcaacagat cgtagacgcg   5940
cggcagcatc ggctcgaact gtaatagcag atcgtcgtca agatcgggta gcgcgtgtcc   6000
gtcttcaccg tcctcgtcgt caccacctcc ccctcgagc ccaccgctcg taccagccgc    6060
gggctccgcg tcctcgtcga tcaccagcgg tcgcgtcggc accggagaat ccacgtcatc   6120
ctgcacgtcg ttttcctcct ctccgtcgtc atcgtccaga acggcaccc gctgcttagc    6180 ccaggacatt ctttttttccg cgtcctcaat cagcggcgcc gatcgccatg aatccgagta   6240
cccacgtgag cagtaacggc ccaacgactc cccctcacgg gccccacacc acgtttcttc   6300
ccccgaccag cccggccccg tccaccagct ccgtcgccgc cgctaccttg tgcagtccgc   6360
aacgacaggc cgtttcgcgt tacagcggct ggagcaccga gtacacccag tggcactcgg   6420
acttgacaac tgagctgcta tggcacgcgc accgcgtca agtacctatg gacgaagcgc    6480
tggccgccgc ggcggccgcc tcataccagg taaatcctca acaccccgcc aaccgttacc   6540
gtcattacga attccagacg ctcagcctcg gcacctcgga ggtagacgaa ctgctcaact   6600
gttgtgcgga agaaaccacg tgcggcggca cgcaatccac cgtactcacc aatgcgacca   6660
acaccactag ctgcggcgga gccgtcgccg gcagtagcaa cgtaggaccc gccggcgctt   6720
cggccgcctg cgacctagat gcagaactgg ccggcctcga aacctcggcg gccgactttg   6780
aacaactgcg gcgactgtgc gcgccgctgg ccatcgacac gcgctgtaac ctatgcgcca   6840
tcatcagcat ctgcctcaaa caggactgcg accagagctg gctcctcgag tacagcttgc   6900
tgtgcttcaa atgcagttac gcgccccgtg cggcgctcag cacgctcatc atcatgtccg   6960
agtttacgca tctgctgcag cagcactttt ccgatctgcg catcgacgac ctgttccgac   7020
accacgttct cacggtcttc gatttccacc tgcactttt catcaatcgt tgctttgaaa    7080
aacaagtggg cgacgcggtt gataacgaga atgtcaccct gaaccatctg gccgtggtgc   7140
gggccatggt catgggtgaa gacacggtgc cttacaacaa gcctcggcgc cacccgcaac   7200
agaagcaaaa aaacaaccct tatcacgtcg aagtgccgca agaactgatc gacaactttc   7260
tagaacacag ctcacctagc cgcgaccgct tcgtgcagct gcttttctat atgtgggccg   7320
gcaccggcgt catgagcacc acgccactca cggaactcac gcacactaag ttcgcgcgac   7380
tagacgcgtt atccacggcc tcggaaagag aagacgcaag gatgatgata gaagaagagg   7440
aggatgaaga aggaggagaa aaaggaggag acgatccggg ccgtcacaac ggcggtggca   7500
ccagcggggg gttcagcgag agcacgctaa aaaaaaacgt gggtcccatt tacctatgtc   7560
ccgtacccgc ttttttttacc aagaaccaaa ccagtaccgt gtgtctgctg tgcgaactca   7620
tggcctgctc ctattacgat aacgtcgtcc tgcgcgagct gtaccgccgc gtcgtctcgt   7680
```

```
attgtcagaa caatgtgaag atggtggacc gcattcagct ggtattggcc gatctgttgc   7740
gcgaatgcac gtcgccgctc ggcgcggcac acgaggacgc ggcgcgctgt ggactcgaag   7800
cacccacctc gcccggaggc gactcggact accacggcct gagcggcgtc gacggcgcac   7860
tggcgcgacc cgacccggta ttttgccacg tcctgcgtca ggcaggcgtc acgggcatct   7920
acaagcactt tttctgcgac ccgcagtgcg ccggcaacat ccgcgtcacc aacgaggccg   7980
tgctcttcgg acgcctgcac ccccaccacg tccaggaggt gaaactggcc atctgtcacg   8040
acaattacta tataagtcga cttccgcgac gtgtgtggct ctgcatcaca ctcttcaagg   8100
cctttcagat tacaaaacgc acctacaaag gcaaagtgca cctggcggac tttatgcgcg   8160
atttcacgca gctgttggag agttgcgaca tcaagctggt ggaccccacg tacgtgatag   8220
acaagtatgt ctagcgtgag cggcgtgcgc acgccgcgcg aacgacgctc ggccttgcgc   8280
tccctgctcc gcaagcgccg ccaacgcgag ctggccagca aagtggcgtc gacggtgaac   8340
ggcgctacgt cggccaacaa ccacggcgaa ccgccgtcgc cggccgacgc gcgcccgcgc   8400
ctcacgctgc acgacctgca cgacatcttc cgcgagcacc ccgaactgga gctcaagtac   8460
cttaacatga tgaagatggc catcacgggc aaagagtcca tctgcttacc cttcaatttc   8520
cactcgcacc ggcagcacac ctgcctcgac atctcgccgt acggcaacga gcaggtctcg   8580
cgcatcgcct gcacctcgtg cgaggacaac cgcatcctgc ccaccgcctc cgacgccatg   8640
gtggccttca tcaatcagac gtccaacatc atgaaaaata gaaacttttta ttacgggttc   8700
tgtaagagca gcgagctact caagctctcc accaaccagc cgcccatctt ccaaatttat   8760
tacctgctgc acgccgccaa ccacgacatc gtgcccttta tgcacgccga ggacggccgg   8820
ttgcacatgc acgtcatctt cgaaaacccc gacgtgcaca tccctgcga ctgcatcacg   8880
cagatgctca cggcggcgcg cgaagactac agcgtcacgc tcaacatcgt gcgcgaccac   8940
gtcgttatca gcgtgctgtg tcacgccgtc tcggccagca gcgtcaagat cgacgtgact   9000
attttgcaac gcaagattga cgagatggac attcccaacg acgtgagcga gtcctttgag   9060
cgctacaaag agctcattca ggagctgtgt cagtccagcg gcaacaacct atacgaggag   9120
gccacgtcgt cctacgcgat acggtctccc ttaaccgcgt cgccgttgca cgtagtttcc   9180
accaacggct gcggcccctc ctcctcgtcc cagtccacgc cgcctcatct ccacccgccg   9240
tcgcaggcga cgcagcccca ccactactct caccaccagt ctcagtctca gcagcatcat   9300
caccgtcccc agtcaccacc gccgccgctg tttctcaaca gcattcgtgc gccttgacac   9360
tgtacggcag aaaagccggc tccaagtgca agcgccgcgg cagcaccatg tgcaaaaact   9420
tgtccttgcg cgcggtttcg ccgccgggaa agacgggcga cagcacgtta gttacagcct   9480
tgagaacctg ctcaaagtac ttgtcggcgt gaatgggcac gccgtgctcg cgcacgtagc   9540
tcggatcttc ggctacctcg tagttgcaca cggccgacgg tggtttccgc gccctcttct   9600
ttgccggctc tcctcctctc ctgttgctct cctctacccc gccgccgtca gcgtcgtcgt   9660
ccgtgccatc aatcgcgtcc gaccgggaaa ccacgccggc ggttacagaa tcaccgttgt   9720
cggaggaacc ctgcggcgcc gtccggacac cgggcgccgt cagaacgtaa aagacccgat   9780
ccccgaccga gggtagctcc tcagaacggg ccgccaatcg cttaatgacg gcaatgtgcg   9840
gcaggttaga ttgacggtac agcgagatgt ccttagagag caccgacgaa agcaccaggt   9900
cctcgacacg cacacggtgc aggtacagat cgtcgcgggc ctgcaccaag cggcgtaaga   9960
tacgccagaa accgcgtggc acgccgtact tcttgacttc atcgagtgag aggcgcgaca  10020
ggcgcacggc tgcttccgag acctcgcgat cctcaaagag cagcgagagg acgtcacgcg  10080
```

```
tgacgccctt gacgaactcg caggccgtct tgcgcaccag atccacgccc ttcatgctca   10140
gacccgaggc gccctccact ttgccgatgt aacgtttctt gcagatcatc ataagagaga   10200
cgaagacctt ttcaaactcc agcttgacgg gctccacaaa aagacaggcc gtcacgtagt   10260
gcgccaggct gggcccacgc gccaccagag cctgcggcgt caggccacga aagcggacaa   10320
acacgctgtc cgtgtccccg tagatgaccc gcgcctccac ccgccgttcg ttcgagcccc   10380
ctgacgatgt ttcgagcccc tccggtaacg cgctgctctc ctccgaatcc cctcccgcg    10440
ttcccactac atagtcttcc tgattaaaaa aattgtgcaa aaaacacggc tctgaaaagt   10500
tgtctttgat gaaccgcgcc gtgcgctcta gcatgtcgcg accgatgcgc gtgatgctgg   10560
cggcgatggg cagacacggc atcataccgt tgaccacgcc ggtaaaaccg tagaaagcgt   10620
tgcacgttac tttgagcgcc atctgttcct tgtcgagcag catacggcgc acagggtctt   10680
gacactcgcg catgcattcg cgcacggcac gccgctgcga aacccacttg ttgagcagtt   10740
ccgagagcac cgagacgcgc accgaagcac gcacaaagcg gtgggtcacg ccgttctcta   10800
gcgtgacgct gtatacgtcg gcggggtcca caggtactc gccacccggc accagcaggg    10860
tggagtagca gaggttgtgg gccatgatga tggaagggta gaggctggca aagtcgaaca   10920
cggccacggg gtcgttgtag taacccacct cgggctcaaa caccgtggcg ccctggtacg   10980
aaaccgccgc agtaccgccg gcgccgtgat tgtcgttgga aacgccgacg ccgccactac   11040
tgccggagcc gacgctgaaa acgccgacgc tgctactact gttactgccg gagccgggtg   11100
aaacgccgtc ctgactggac ggcgcagatt gcaagggcgg cgacatctga acatagccg    11160
ccacagaacc cgcgtcgccg ggcacagcgg cggtagagat gatagcagcg ttaggtgaca   11220
cagcaacgct attcgtttcg ggcaccgtcg tacctttgct gtagtggttg ggcaggataa   11280
aatcgcggca ggcgcactcg tccagcagcg aggtgtagat acggatctgc tgtccgtcaa   11340
agatgacacg ccgcaacgga attttagcca gccgcgcgcg ggccccggcc tcgtagtgaa   11400
aattaatggt gttgaacaga tcgcgcacca atacggcgtc ctgcagacag taacggccta   11460
cctgggcgcg gccctcggca ttagccacga acaacgcgg gatgtccttg taagacaggt    11520
catccttgcg ttgccgcagg taaagctcgg ccatagtgtt gagcttatag ttgggcgagt   11580
tagtcttggc catgcataca gggtacatgt cgataaccac cgaacccgca atatacacct   11640
tggtggcggc cgtgctggcc ggattgttgt gagaagccga gggaaaagcg gcggcgtact   11700
gccgcttaaa acccacggcg gggctgtgta aaagaaacg gccgccctgc gccgtaggca    11760
acttgcagaa gcgctgcgag tccaccttat acaggtactc gagacgcgtg aggatgtact   11820
tcaagtcaaa agagttgatg ttgtaaccgg tcacaaaggc cggcgcgtac cgttgaaaga   11880
aaagcataaa gcccagcagc agctcgtatt cggaagggaa ctcgtagacg tccacgtctg   11940
ggcccacctg cccgcaggtg ccgatcgtaa agagatgaag acccgagtgc ccaaagatca   12000
caccctccga agtgcagccc cgaccatcgt tcccgtttgg gatccctga tccacggcgg    12060
tgtttccccc cgtctcgtag cacacgcacg agatctgaat gacaatgtca tcggacttct   12120
cggcgcaggg aaaaccaccc tcgccgctca tgcactcgat atcgaaggac aggcatcgat   12180
agcgcggcca cgagctgtcg tcgggcacag ccaccaggtc agagacatcg cagtctacct   12240
cgatatcaca agtcgacgcg cgaccctgct gccgccagtc gtaacgattc acggagcacc   12300
agccgaacgt ggtgatccgc cgatcgatga ccaaacgcgt cagcggatcc acacggacct   12360
cgtacacggg aaaaccctgc tccagcagat actcgccgat ttttctggcc atggtccagt   12420
```

```
tgctgataga cacacactgc aaatcgggca cgggtcgcgt cccgtaccca tagatggagg    12480
tcttggtggc cggcgtgaca gacacggcgt atggcgtccg cggttcgggc actagttcgc    12540
ccacgctggc aatgacctca cgcagcctat cggtgtcgct gtactcacag taaaagtagc    12600
tgcgctgccc gaaaacgttg acgcagatac tgtagccgtg ttctgtggcc ccgaagaaac    12660
gcaacacgtt ccccgaaggc accagatgct gacgatagcg cggcgacacg ttttcgggcg    12720
agtcgaagaa gagcacggcg tccgtctgat cgtaggtgtg aaaacgaata ggtcccacca    12780
cgcgacccac cagggtctcg cgccaaggac acggccaaac catgtcatga ctcaacaaat    12840
gtttaatctc tcgatagaac atgagaggca gccgtcccgt cttatgcttg atcaaccccg    12900
tctgaccgtc gaacatgaca cctcgcggca cgatctgcaa aaactgtttc tgtggcggcc    12960
gcttgcccga gccctgcgcg gagccgggct gcgaacgctg acgccggcca cccgcgaccg    13020
caccgccggt cacgccgccg ctcagatacg ggttgaaaaa catagcggac cgtgagaggc    13080
tgacagctta cgaagcaaaa tcacaaagaa aatacacatg cagcacctag atatccagtt    13140
taaccccgta tatcacaagt ctctgtgtca atattttttg tctagttttt ttttcctcct    13200
ggttcagacg ttctcttctt cgtcggagtc tttcaagtgt ctgtagccgt ttttgcgatg    13260
tcgcagccgg tctagcaggt taggcttctg tcccttgtcc tgcgtgccag tctgtccgtc    13320
caaagaatct gtaccgttct gctgcgctcg ctgctctgcg tccagacggg ccagggccag    13380
aagcatctgg taagcctgct cgttggtgta aggcggagcc gccgtggatg catcagacga    13440
cggtggtccc ggtcctttgc gaccagaatt ataaacactt tcctcgtagg aaggcggagc    13500
ctgtaacgac gtgtctttgg tgctgcccga cgtcacggtg gtcccgtcgg cggacaccag    13560
atagggaaag aggttctgca gcggctgcgt gcacagacgc cgctgtcgag tatagatcaa    13620
ataagtgata atgactacgg ctatggccac gaggatgatg gtgaaggctc cgaaggggtt    13680
tttgaggaag gtggcaacgc cttcgaccac ggaggccacc gcgccaccca cggccccaat    13740
ggctacgcca acgcctttc ccgcggcgcc caggccgctc atgaggtcgt ccagacccctt   13800 gaggtagggc ggtagcgggt cgactacctt gtcctccacg tactttaccc gctgcttgta    13860
cgagttgaat tcgcgcatga tctcttcgag gtcaaaaacg ttgctggaac gcagctcttt    13920
ctgcgagtaa agttccagta ccctgaagtc ggtattttcc agcgggtcga tatccagggc    13980
gatcatgctg tcgacggtgg agatactgct gaggtcaatc atgcgtttga agaggtagtc    14040
cacgtactcg taggccgagt tcccggcgat gaagatct                           14078
```

<210> SEQ ID NO 25
<211> LENGTH: 4569
<212> TYPE: DNA
<213> ORGANISM: Human cytomegalovirus

<400> SEQUENCE: 25

```
agatcacgat acagccggcg gtatcgataa tcttgttgcg gtactggatg gtaaagtcgg     60
gctcgggctt gatgtcttcc tgtttgatga ggggcagcat gataggcgcg ggaggcacgg    120
gcggtttaat aatcaccttg aaaggacgcg tggttttgcg cggtttctta cgcgggctga    180
gctcgggagt agcggatgcc ccggggagag gagtgttagt aaccgcgacg ctggtggggg    240
tcggcttgtt aagaggggcg ctgctaacgc tgcaagagtg ggttgtcagc gtggggccga    300
tgctactgga atcgataccg gcatgattga cagcctgggc gaggatgtca cctgatggtg    360
ataagaagac acgggagact tagtacggtt tcacaggcgt gacacgttta ttgagtagga    420
ttacagagta taacatagag tataatatag agtatacaat agtgacgtgg gatccataac    480
```

-continued

```
agtaactgat atatatatac aatagtttac tggtcagcct tgcttctagt caccataggg      540
tgggtgctct tgcctccaga ggcggtgggt tcctcagcac catcctcctc ttcctctggg      600
gcaacttcct ctatctcaga cactggctca gacttgacag acacagtgtc ctcccgctcc      660
tcctgagcac cctcctcctc ttcctcatca ctctgctcac tttcttcctg atcactgttc      720
tcagccacaa ttactgagga cagagggata gtcgcgggta caggggactc tgggggtgac      780
accagagaat cagaggagct gacaccagcg gtggccaaag tgtaggctac aatagcctct      840
tcctcatctg actcctcggc gatggcccgt aggtcatcca cactaggaga gcagactctc      900
agaggatcgg cccccagaat gtactgggca aagaccttca tgcagatctc ctcaatgcgg      960
cgcttcatta cactgataac ctcaggcttg gttatcagag gccgcttggc cagcatcaca     1020
ctagtctcct ctaagacata gcagcacagc acccgacaga actcacttaa gagagagatg     1080
cccccgtaca tggtcatcat acaagcgtca ctagtgacct tgtactcatt acacattgtt     1140
tccacacatg tagtgaggat atccataaat atgtgatcaa tgtgcgtgag caccttgtct     1200
ctctcctcat ccaaaatctt aaatattttc tgggcataag ccataatctc atcaggggag     1260
cactgaggca agttctgcag tgccgccatg gcctgactgc agccattggt ggtcttaggg     1320
aaggctgagt tcttggtaaa gaactctata ttcctgtagc acatatacat catctttctc     1380
ctaagttcat cctttttagc acgggcctta gcctgcagtg caccccccaa cttgttagcg     1440
gcgcccttgc tcacatcatg cagctcctta atacaagcca tccacatctc ccgcttatcc     1500
tcaggtacaa tgtagttctc atacatgctc tgcatagtta gcccaataca cttcatctcc     1560
tcgaaaggct catgaacctt atctaagata tctaaggcat tctgcaaaca tcctcccatc     1620
atattaaagg cgccagtgaa tttctcttcc gtctgggtat attttttcag catgtgctcc     1680
ttgattctat gccgcaccat gtccactcga accttaatct gtttgactgt agaggaggat     1740
aacaacacat ataagtatcc gtcctcctga ctcatttatc gctatctcga tgccccgctc     1800
acatgcaaga gttaatcttt actctatctg acatacacaa gtaaatccac gtcccatgca     1860
ggttagtata catcacatac atgtcaacag acttaccgag ttctgccagg acatctttct     1920
cggggttctc gttgcaatcc tcggtcactt gttcaaaagt tttgagggat tcttcggcca     1980
actctggaaa cagcgggtct cccagactca gctgactgtt aacctccttc ctcaacatag     2040
tctgcaggaa cgtcgtggcc ttggtcacgg gtgtctcggg cctaaacaca tgagaaatag     2100
agtcataagc acatgggtca catacaggag atatgtatat aacattaata caattttatt     2160
aaaaaaaaag gggggcaca aaccccgaca cgtaccgtgg caccttggag aagggccct      2220 cgtcaggatt atcagggtcc atctttctct tggcagagga ctccatcgtg tcaaggacgg     2280
tgactgcaga aaagacccat ggaaaggaac agtctgttag tctgtcagct attatgtctg     2340
gtggcgcgcg cggcagcaac gagtactgct cagactacac tgccctccac cgttaacagc     2400
accgcaacgg gagttacctc tgactcttat cagaacacaa caactcagct gcctgcatct     2460
tcttctgccg ctgccttaag tcttccaaat gcgtcagcgg tgcaagcccg ctccccgagc     2520
tcattttcag acacataccc taccgccacg gccttgtgcg gcacactggt ggtggtgggc     2580
atcgtgctgt gcctaagtct ggcctccact gttaggagca aggagctgcc gagcgaccat     2640
gagtcgctgg aggcatggga gcagggctcg gatgtagaag ctccgccgct accggagaag     2700
agcccatgtc cggaacacgt acccgagatt cgcgtggaga tcccacgtta tgtttaataa     2760
aaactgcggg cactggggac ggtggtgttg tatatgtgaa tttgtaaata ataaatgaga     2820
```

-continued

```
ccccatcctg taaaaataca gagtccgtgt cagtctctga aggacagtgt attggcatat    2880
agccaataaa gagagttgtg gcaaagagcc atgttatgga ttagtaatgg aaagtatcgt    2940
caccaatagg ggagtggtca ataatggtca ataacccaca cctataggct aagctatacc    3000
atcacctata acatgaggaa gcggggtgt atagacccca agccaaaaac agtatagcat     3060
gcataagaag ccaaggggt gggcctatag actctatagg cggtacttac gtcactcttg     3120
gcacggggaa tccgcgttcc aatgcaccgt tcccggccgc ggaggctgga tcggtcccgg    3180
tgtcttctat ggaggtcaaa acagcgtgga tggcgtctcc aggcgatctg acggttcact    3240
aaacgagctc tgcttatata gacctcccac cgtacacgcc taccgcccat ttgcgtcaat    3300
ggggcggagt tgttacgaca ttttggaaag tcccgttgat tttggtgcca aaacaaactc    3360
ccattgacgt caatggggtg gagacttgga atccccgtg agtcaaaccg ctatccacgc     3420
ccattgatgt actgccaaaa ccgcatcacc atggtaatag cgatgactaa tacgtagatg    3480
tactgccaag taggaaagtc ccataaggtc atgtactggg cataatgcca ggcgggccat    3540
ttaccgtcat tgacgtcaat gggggcgta cttggcatat gatacacttg atgtactgcc    3600
aagtgggcag tttaccgtaa atactccacc cattgacgtc aatggaaagt ccctattggc    3660
gttactatgg gaacatacgt cattattgac gtcaatgggc ggggtcgtt gggcggtcag    3720 ccaggcgggc catttaccgt aagttatgta acgcggaact ccatatatgg gctatgaact    3780 aatgacccg taattgatta ctattaataa ctagtcaata atcaatgtca acatggcggt     3840
aatgttggac atgagccaat ataaatgtac atattatgat atggatacaa cgtatgcaat    3900
ggccaatagc caatattgat ttatgctata taaccaatga ataatatggc taatggccaa    3960
tattgattca atgtatagat cgatatgcat tggccatgtg ccagcttgat gtcgcctcta    4020
tcggcgatat agcctcatat cgtctgtcac ctatatcgaa actgcgatat tgcgacaca    4080 cagaatcgcc caagtcacca aagtcgtcta tcgccatccc ccgtaaacga taagcgct     4140 atcgccagat atcgcgtatg cccaaaaatc acttttggaa aaatggcgat atcagttaca    4200
cagaaactca catcggcgac attttcaata tgccatattt tcaaatatcg attttttccaa    4260 tatcgccatc tctatcggcg ataaacacca ctatcgcgcg acatgaattt agtcggcgac    4320
agaaatctca aaacgcgtat ttcggacaaa cacacatttt attattcact gcagcatata    4380
gcccatttta gcgcggcaca catccagccg tttgtgtttt ttaacgctct ccaggtactg    4440
atccaggccc acgatccggg ttatcttgtc gtattccagg ttgatccatc gatagggaac    4500
gctgccagcg gcgcccagca ggtactgcgc cttgtcgttc actttgccgc agcgtattcg    4560
cccgtcagc                                                           4569
```

<210> SEQ ID NO 26
<211> LENGTH: 2666
<212> TYPE: DNA
<213> ORGANISM: Human cytomegalovirus

<400> SEQUENCE: 26

```
agatcgtgct tccctcttcc aaggatcgga aagtagcgtc cgtcgtttcc gcggacgcgg      60
cttccctggt acgctccgtt tccgacgacg cggtttcccg ctgcgtggaa actgtctcca     120
tgtcgggacc gcagcgcccg gcggcgtatc cgcaaggtct cgaagctaca gcttgtcaga     180
ggaaaagtag gtttgcaaaa aggtgcgcag ggtcatgatt ctcagcacca tcagcagagt     240
gaaaaccaga ctgagaaaca ccttgacggc cgccaaaagc gcgcgttcca gcggcgtctc     300
gtagcgtaca gccagggccg cttcgtggaa atgcgagacg gctagacagg taatgagcac    360
```

-continued

```
gctgaaggac aagacgatct taaagcacca ggaccaacca cgcctcaaga tgaccaccac      420
gattgccgtg aaggtcaacg tgatcaaagc atggacgacc acgatctgac ggcggacggt      480
acgttcggga gccaacaacg ctacgccggt gcagctgaga aaggccagta aggtgaacaa      540
cgcggccgag atgaccaacg taccgtccag gcagagacat atcacgatca acggcggcac      600
gtgaagcagc gtgtaaaaga gcagaacgcc gatattgctg ggatgcgatg tttcgtaaca      660
gtgaatgaag atcactgacg tgacgggtat gacaaagacg aggctgggcg aggactccgt      720
gagacacaga cgagaatggt gaaaccacgt cgcgggcgcc gcgtagcaga aggcgctcaa      780
caacgcggtc aagccggcca gctgccaacc cacggcgcca taggtgtgca gcgccacgcg      840
gcaacagtcg acccaagcca gactgcgggt cgccagccgg gtctcttgga tcccgggggg      900
cacgtagatg accgtgccat cggtgggtac ttgaaaccct ttttctcttc tcatggtgcg      960
ctgcgttctc tggaaacggc tgctctgtcc gaaaaccagt tccgaacgaa aatctagggc     1020
gagagggtgg acaacggcgt cgacgacgaa gcatgggaca ggtcgttcgg cgttaacgtc     1080
atcgcgtcgg acgacggtag ttctaagaga cgtagatcgc tcagcaggtc ctgacagttg     1140
cggattcgca agatcagaaa aaaaagggaa atgaacgtaa taaagagctg tagcgacgta     1200
tgcgccacat cgcgtggcat aagaacgtga cggacgaaaa ggacctgctg cgaaaagtga     1260
ccggcgaaga taaggcccac cgtgctgtag aagcccaaaa gcagccgcag gggccaagtc     1320
cagggccgcg tgaagacgat gagaacgttg accagaaaga ccacgaccca gacgccgttg     1380
atgagggtaa attgatcgga cagggtgcag ttgtcgcgac agatgaagac tacttccgcg     1440
cagagcaagg tgatgaccaa cgtgagcaca acgacgtca acacctcgcg gggctcctgg     1500
caggcacacg tgacacctag cgccgggatg tgcgccagga ggccggcgag taatagcacc     1560
agctgtcgga acggacgacg gcagcgcggg tgccggtttc gctgagcgag aaccggtcgc     1620
tcatagcgga aatacacgaa gagcgcggag gccacaggca ccaggaggag cacctcgggc     1680
gcccagacaa cgtgacaagg aaagcccgga cgcgacttga gagtcgctgt agggaagacc     1740
agagagaagc tacccaagac ggccaccgcc gcggagattt ggaagaggag caagccggcg     1800
attcggacga caacctcgaa gcgatgcacc cagcccagca cggccaccac ggccgcttca     1860
tcatagtcgt cgttgttgcc gctgtcgaac agccgccgaa cacgatctg tcgctgggtc      1920 gcggtgggaa agcgcagacc catgacagcc ggaggctata tgaccgcgcg tctaagacgc     1980
gagatccgtg gggggacttt tagatgtttg gcggcccgc ggttctaaca ggcttgattg      2040
gtggagacgg ccggcgcggc gggtggggga aacgacgagt ttttccgtta cgccatggtt     2100
cgcgtgaggt ttctctgtac ctcccgcaaa aggtcacagc ccgaaatgga ggccgcgttg     2160
gtggccccgg tggcgcgtga cgataaccag gtcatccaag cgatgagttt gtctaatgag     2220
tcctcggtgg tgaagaggat gagaatgagc aggtacaggt acaccaggtt ctcatagaga     2280
cacaaggtga gcaggtcagc ctcggaccac gcgatctcaa acaggcgcgt ggtgtcaaag     2340
accgtgacga ccagcatgaa gctgagcgcc atggcgtaat agcccaaaaa aagtttgtgc     2400
cccaacggta cgggctgcag gtaaagtgcg atcaagaacg cgataacgcc gatcacaaac     2460
agcgtgacga tgacctgcca tcgacggtga ttatggccgg ctagaccgt gacgcagctg      2520 cagaggctaa aaagcacgca agccaagagg cccgagaagg tcactagcgt agaggaggag     2580
caggcgctgg ccacgatcac cgaaagcgtc gtgagcacgc tataaatggt gagcaggcca     2640
gggctcggtg gcgacgtgaa cgatcc                                          2666
```

<210> SEQ ID NO 27
<211> LENGTH: 5258
<212> TYPE: DNA
<213> ORGANISM: Human cytomegalovirus

<400> SEQUENCE: 27

| | | | | | | |
|---|---|---|---|---|---|---|
| gatctggccg | aaaacctacg | gcatctctga | aagcggtttt | tcctctttt | ctacgtgtct | 60 |
| gtctcaagat | gagacgtcga | tatcaataaa | aataccgtcg | acgtggtttt | tttaacagtg | 120 |
| tggttttctt | tattgactag | cgaagtacac | agtttacgag | tagaaaagac | agggaaaggt | 180 |
| tatataaaat | gctgtattat | atacaaaaac | atgcacataa | acaaacggga | ccatcgtgct | 240 |
| catcatcccc | tccttgatca | gttgttcatg | taaacgtgtg | gcggggtgag | gggcggcatg | 300 |
| ccgttggcgg | cgccgggaat | aatgtgccgt | cgaccgacgt | cgcacacctt | gaaacgccgt | 360 |
| cggcgcacgc | agcggtcgca | ggacgggata | tcccagagga | agcccatgta | ggtctcgggg | 420 |
| tcctcgtcgt | gaaagcggta | ggagagttca | aagtggtgca | acgagcccgt | ccgagctcgc | 480 |
| agcttctggc | gaacaccctc | cacgtcatcg | gtgcacagcg | acagtgctgg | gctgtcacac | 540 |
| agggcctgaa | gctcctgcgg | ccacaggtgc | gtggccaggg | gcgagtccgt | cgtcaccagt | 600 |
| ttgacgcagt | gcatcaggtt | ctcggtgatg | gcgtcgtaca | ggcgactctc | agcctcctcg | 660 |
| tgcgtcatca | cgtttcgagg | cagcgacagc | tcgtcgtcgt | catcctcgtc | aaacatgatc | 720 |
| atggggtcag | gggtttttt | gggatgttga | caggtgggtg | tcttttccag | acgcacgatg | 780 |
| gcctcacgcc | ggccgctgaa | acggtggttt | cggtgtccct | tctttcccat | gacgcaggtg | 840 |
| aacataacca | cgtcctcggc | caaacggtag | acggcgtcca | tggcggggtc | gtagccgtag | 900 |
| acgacgccga | aagtgtccac | caagacgtac | tggcgtacga | ggaactcttt | gcgttctggc | 960 |
| acctcgtggc | ccagcgcgcc | caacaactgg | tggtaacagg | tgatgcgcgg | cacggtacgg | 1020 |
| atcatgagct | ccatggtctg | gatgctgccg | cccgcgcgga | cgacgctgaa | ggatgtttcc | 1080 |
| ttgaacttca | taacctctgt | gttgtgggtc | cagaaggcga | aatgggtgtc | gggacactca | 1140 |
| tcgaagggt | cgtcgatggt | gtaggaagcg | tagcctcgct | tggtcacctc | ggccgacagg | 1200 |
| ctctccacgt | caccgcggta | gagcatgacg | gcgttccagt | agtcgtcgta | ctgcaccatg | 1260 |
| ggccgctggt | agtcgcgcat | agtgtggaag | tggtcgcggt | gacgaaagcc | gttccgcaga | 1320 |
| aagtccttca | tggtgggtgc | cagctcgtag | acgcagtcgc | gcaggtcatc | gtagcagtag | 1380 |
| atgccgccgc | gctgcccgat | gagcacgatg | agttggtagc | gcataaagcc | cggaccctcg | 1440 |
| acgaagccaa | aggggtgcag | gtactcctga | cagcagacgt | aagcacctgg | tagagaatag | 1500 |
| aaaaaatcca | cgcacgttga | aaacacctgg | aaagaacgtg | cccgagcgaa | cgtcctctt | 1560 |
| ccaggtgtct | tcaacgacgt | ggggcttacc | ttgcgaacag | acggtgccca | tcttgcccac | 1620 |
| gaagggcccc | agggcgctgc | gcgaacggag | ctggatgaag | cagcgttcgg | gccaggccac | 1680 |
| gtgcagccgg | gtgccgcatt | cctgctccag | aaagtcgttg | agaccgttaa | agtccccggc | 1740 |
| tcggatggcg | atgcagccgt | aggccatcag | cgtgtcccgt | aggtcgtcca | tgacggactc | 1800 |
| ctctaccttc | gctcgccgac | gctgcgcttc | tccagccacc | gctgcggtcg | acagactcct | 1860 |
| ccgtccgcct | tcggagaact | acggcgcggc | ggcacggcct | ttatagacac | tatcagcgtt | 1920 |
| gacgtcagac | gatccgatga | acgtcgtttt | tgtgctggaa | acttccctcg | tcccgacaaa | 1980 |
| tgtagcggaa | atcttcaagc | aaatcgcgac | gaagtccgat | gaggaggatg | caaagaggc | 2040 |
| tgagcaacgc | gatgctgccc | gccgccacag | tacatatgct | caacaacgcc | cagtgtccca | 2100 |
| aggcgcgact | tttggctcgg | aggagagccg | aacggcggtt | tctccacatg | acggacaacg | 2160 |

```
tggtccagta cgtccatcct ttgcattccg gtgtccagac gggaagcgtt gtcatgttat   2220
ttcccgtaac tgtcacgtta tgttttgttt tgtttctcgt gagcttaacg gtcctcttga   2280
gaaatcgcgg gcacatgtct tgtagaaaga tataatcact ttccgcgtat ttcgtcagtg   2340
ttgacatcac ggtggtagtg ttttctgaag aagtagcgtt gtcagtgacg tttgtttctt   2400
cccaacgtac gtatgattcg aacggactcg tgtgcgctat tgcccgcaac acgtagctgt   2460
ggccggtgaa gttgagcgtc agttgtccca cggtcacgtt cgtgtcattc ctaaaacatg   2520
ctacttctcc gtgaacttcc gtgacgttta tctcacgact ctcgttcaag acacgcaggg   2580
gaaaccagcc ttccaggtga tactgaaaac caaatttaag catgacgctg tgccatttcc   2640
gtcgtgattg attaaacgtt acattcaagg gcagtctggc ttcggtcccg agacaggggc   2700
cgttgtagat ttgcgtgtga ttgcgtgtgc agtttaggtg gcagttcatg ctcgtggtgt   2760
tggaagtgcg attaacgtcc gtaccgtggt acgtacatcg gaccgaaaca ccgtgtcccg   2820
tgctccaaag cagcgtcaac aacagccaca cagaaaccta cgtggagacg acacgggact   2880
ttttattgac ggagactcac gtttctaccc tcccctttcc cgtaggtaaa acccacgtt   2940 tatcacacac gttgttttta cctgaaaccc gcgcagcccg tggacgcgac aaaaaaccgc   3000
ggcactagaa agaaaatgaa acaagtatgt ttattaagca gcatgtgggg ctaatagggg   3060
ggataactga ggtatagcaa ctatgaaaaa atactacaaa aaaaaaagct gaacatggtc   3120
atctagcagc aaagttctcc ttctagacca cgaccaccat ctgtaccacg tcgccctccc   3180
cggccgtgta cacgacatcc ttcaccacga ccggcggcag cggcggcgac gaggacaact   3240
cgctctcgac ggaggccggg acgacagagg acgggggggt ggtggcggcg gaggacgaag   3300
gggtggcggc ggcagcggga tcttcttccg acacgggcaa cggcaggctc ggcggcgcgg   3360
acagcacccg ttgcgccggg gcgtgagaag gctgagcccc ggtggcctgg atgtgggcca   3420
acgaattggc tcgcagcgag tcgcgatcca cgaaggtcat aggaatttc ccttcgcgga   3480 tccgccgctc agattccagg atggcgcgca cgtagctgtt caccgacttg gcaaaagtgc   3540
gcggcccctc cgtattcttg tcgcgacgcg cttccagcac ctgcttttcg tagtccagct   3600
ggtggaagac catcaccagg tcgtccatag tgtgcgcgtg ctgacggacg tgggagcgca   3660
cctccaccgg gaacaaagcg ttccaatact ccagcacgat agcaccgtgc cagaactgcg   3720
ccatgctggg cgccaggaaa acaggatac cggagtcgta ggcgaacacg tcccacttgg   3780
gcgtcatgaa caacaccagc tgacgcgtgg gccgcaccga agcttcctcc caggcctcga   3840
tgaccccgaa catgatgagc tcctggtcca acgggggggca gtgtcgctcc agccaactga   3900
tcttgctcag gttcatctgc agaaactcgt acgaagggtc gcagatgcac acgtagagac   3960
ccgagtcgtg ccgcagcctg gctccgcgct tcatcagttt cctcaccgcg tagcgaagcg   4020
ccaccttgcc caacgccgac gcctggatca gtcccccac gtccatctgc gtctgtcgcc   4080
actcggcctc gtccagcagg ctcatgatag cggcagtgct atgcgtggtc gtagtcatcc   4140
tttctatcct tctctatgaa tagcagcaat agcggtaaag tcccttctta tactatcccg   4200
gagtctgtgg ttttttttgtt tacccctgct tactggtgag actgctgggg gccgttgtgc   4260
tgcagcatcc gagctcgttg ccgccgttgc cacaggaacc ggtgtctccg cagggccttt   4320
ttgagggctt cgcaggcttc tcgcgcaagt cctgagaggc cctcggcgtc gatgggttc   4380 acctcgggcg tccgagcctc gttttcttct tcttcatcct cccttccctc ctccgtgtcc   4440
tcccgctctg tgtcctccgt tacgctctcc tccccggcct cggccaagag cgcggccacc   4500
```

```
aagtccacgg accgctcggt ctccgagttc tcaccgtcaa ttacgccatg ttggcggcgt    4560
aaccggtgcc gagaacgccg ggtgagcgca catgcttttt tctttcttaa ccaaggcggg    4620
agaggatctt caaggcgttt tcgctggatc cagcggtagc taaagtacca aaaggccagc    4680
aggcccacgc tacctaacag attcacgtag actggagaca taattaaaga aagaagtgaa    4740
acccgcgtgt gggtctcacg tcgtcttgaa acaccgtctt atatacatga agatgccgga    4800
catgacgcgc ccaagacacg tggggttttc cccttaggcg acccggtttc ttaagatgtt    4860
tttcatcttc gcacgcgatg tactacatca aagggtcggc tgaccgaccg cattgacgca    4920
cagtttccga gtacgcgcgt ctcggagcac ctgacggtga gccacccaac tcacgcggat    4980
aggggacaac actgacgtga ggggcgattc acgtcactga cgggaataag acgggtgagg    5040
gatttccacc ttttttcttaa gtgtgactct ctttacggta aatcgcacct gtgacctctt    5100 aaccctcct ccctggtacc cgataaccgt gaaaaacaca caccacacgt cacgacaccg    5160
atcgattttc tttattctta gtgtgatgat aggtaagggc actcgtgagg atgtgcaatt    5220
atcattatca agccttttc aaggcgtagt gatgatcg                             5258

<210> SEQ ID NO 28
<211> LENGTH: 20834
<212> TYPE: DNA
<213> ORGANISM: Human cytomegalovirus

<400> SEQUENCE: 28
tgttgagtag taggtgaaat gcgtgagggt ccagcgcttc ggatgcggcg tccgcgccat      60
atcgttgcga aggtaggtga ctgaggaggt agacggtgaa gacagtgagg taggggggga     120
ggccgggccg catagcgcgg ctgcgccgct gggttcagcg gcgtgatcca ggtggtggtt     180
ggcgttacac ccgagagaag gagagaaagg atcccaggaa ggggcacccg ggtgtggcgc     240
tacgggttac aaaagtcgcg tctctgtcta tttaatacga tgtcattggc cgctgcgaag     300
gaagaagagg ggacacgcgg gtaagccatg ccgtccgggc gtggggacga cgctgattcg     360
acggggaacg ctctgcggag attgcctcac gtgcgtaagc ggatcggtaa gcgtaagcac     420
ctggacatct accgtcgcct gttgcgggtc tttccctcgt tgtggccct caaccgcctg      480 ttgggaggcc ttttcccacc cgagctgcaa aagtaccgtc gccgtctttt catcgaagta     540
cgattaagtc ggcggattcc cgactgcgtg ttggtgtttt taccgccgga ctctgggtcg     600
cgcggcatcg tgtattgcta cgtgattgag ttcaaaacta cgtactcaga cgccgacgat     660
cagtccgtgc ggtggcacgc cacccacagc ctgcagtacg ccgagggcct gcgccagctc     720
aagggcgcct tggtggactt tgattttctg cgtctgccgc gcggtggcgg tcaagtctgg     780
agcgtagtgc ccagtctggt tttttttcag caaaaggccg atcgcccatc tttttaccgg     840
gcttttcgtt cgggccgttt cgacttgtgt accgattctg tcctggacta tctgggacgg     900
cgtcaggatg agtctgttgc acacctttg gcggctaccc gtcgccgtct tcttcgaacc      960
gcacgaggaa aacgtgctgc gctgccccga gcgcgtgctt cggcggttgc tggaggacgc    1020
ggcggtgaca atgcgcggcg ggggctggcg cgaggacgtg ctcatggacc gggtgcgcaa    1080
acggtatctg cgtcaggagc tcagggatct gggtcacagg gtgcagactt actgcgagga    1140
tctcgaaggg cgcgtgtccg aggcggaggc gctgttgaac cagcagtgcg agctcgacga    1200
aggaccgtcg ccgcggacgc tgctacaacc accgtgtcgt ccgcgttctt cgtccccagg    1260
gaccggcgtg gcaggagctt ctgccgtccc acacggtctt tatagtcggc acgatgccat    1320
cacgggaccc gccgccgccc cgtctgacgt ggtcgccccg tctgacgcgg tcgccgcgtc    1380
```

```
agcggccgcc ggtgcttctt ctacctggct ggcgcagtgc gccgagcggc cgttgcccgg    1440
gaacgtacct agctactttg gaatcacgca gaacgatccc tttatccgct tcacaccga     1500 ttttcgcggc gaggtggtca acaccatgtt cgagaatgcc tctacttgga ctttctcctt    1560
tggtatctgg tactatcggc tcaagcgggg gttgtacacg caaccacggt ggaaacgagt    1620
gtaccatctg cgcagatgg acaacttttc catttcgcag gagctgctgc tcggcgtggt    1680
caacgctttg gaaaacgtga cggtgtatcc gacgtacgac tgtgtactct ccgatttgga    1740
agccgccgcc tgtctgctgg ccgcctacga acatgcgctt tgggagggcc gcgatccgcc    1800
ggactccgtg gcgacggtgt tgggtgagct ccctcagctg ttgccgcgtc tggccgacga    1860
cgtgagtcgt gagattgccg cttgggaagg ccccgtcgcc gcgggtaaca actattacgc    1920
gtatcgcgac tcgcccgatc tacgctacta catgccccta agcggtggtc gtcactatca    1980
cccgggcact tttgatcgtc acgtgctggt gcggcttttc cacaaacgcg gcgttattca    2040
gcatttgccg ggctacggga cgataacgga ggagctggtg caagagcgtc tgtcgggcca    2100
ggtgcgcgac gacgtgcttt ctctctggag tcgacgtctg ctggtcggca agctgggtcg    2160
cgacgtgccc gtctttgtgc acgaacagca atatctgcgt tcgggcctga cctgcctggc    2220
tggcctgctg ttgttgtgga aggtgaccaa cgcggatagc gtcttcgctc cgcgcacggg    2280
caaatttacg ttggccgacc tgctgggttc ggatgccgta ccggcggcg ggttgcccgg     2340 ggggcgcgcg ggcggcgaag aggagggcta cggggacgg cacgggcggg tacgtaactt     2400
tgagtttctg gtacggtact acatcgggcc gtggtacgcg cgcgacccg cggtcacgct     2460 gtcgcagctc tttcccggcc tggctctgtt ggccgtgacc gagagcgtgc gcagcggctg    2520
ggatccctca cgtcgcgagg acagcgccgg aggtggcgac ggcggcggcg ccgtgctcat    2580
gcagctcagc aagagcaacc ccgtggccga ctacatgttc gcgcagagct ccaaacagta    2640
cggcgattta cgtcgcttag aggtacacga tgccctgctc tttcactacg aacacgggct    2700
agggcggctg ttgtcagtga ccctgccgcg tcaccgtgtg tccactctgg gctcgtccct    2760
ctttaacgtc aacgatattt acgaactgtt gtacttttta gtgttggggt ttcttccgag    2820
cgtggcggtg ttgtaatttc caccacgtgt cgctcgctgc ataaagggcg aacgtcctcg    2880
gagagggtat attcgttcgg cgagagcggg cggcggtggt gggtatgtcc ccttctgtgg    2940
aggagactac ctcagtcacc gagtccatca tgttcgctat tgtgagtttc aaacacatgg    3000
gcccgttcga aggctactct atgtcggccg atcgcgccgc ctcggatcta ctcatcggca    3060
tgttcggctc cgttagcctg gtcaacctgc tgactatcat cggttgcctc tgggtgttgc    3120
gtgttacgcg gccgcccgtg tccgtgatga ttttttacttg gaatctggta cttagtcagt    3180
ttttttccat cctggccacc atgttgtcca agggtatcat gctgcgtggc gctctaaatc    3240
tcagcctctg tcgcttagtg ctctttgtcg acgacgtggg cctatattcg acggcgttgt    3300
ttttcctctt tctgatactg gatcgtctgt cggccatatc ttacggccgt gatctctggc    3360
atcatgagac gcgcgaaaac gccggcgtgg cgctctacgc ggtcgccttt gcctgggttc    3420
tttccatcgt agccgctgtg cccaccgccg ctacggggttc actggactac cgttggctag    3480
gctgtcagat cccctataccag tatgccgcgg tggacctcac catcaagatg ggttttttgc    3540 tggggcgcc catgatcgcc gtactggcta acgtggtaga gttggcctac agcgatcggc    3600
gcgaccacgt ctggtcctac gtgggtcgtg tctgcacctt ctacgtgacg tgtctcatgc    3660
tgtttgtgcc ctactactgc ttcagagtcc tacgcggtgt actgcagccc gctagcgcgg    3720
```

```
ccggcaccgg tttcggcatt atggattacg tggaattggc tacgcgtacc cttctcacca    3780
tgcgtcttgg cattctgccg ctctttatca ttgcgttctt ctcccgcgag cccaccaagg    3840
atctggatga ctcctttgat tatctggtcg agagatgtca gcaaagctgc cacggtcatt    3900
tcgtacgtcg gttggtgcag gcgttgaagc gggctatgta tagcgtggag ctggccgtgt    3960
gttactttc tacgtccgtc cgagacgtcg ccgaggcggt gaaaaagtcc tccagccgtt     4020
gttacgccga cgcgacgtcg gcggccgttg tggtaacgac aaccacgtcg gagaaagcca    4080
cgttggtgga gcacgcggaa ggcatggctt ccgaaatgtg tcctgggact acgatcgatg    4140
tttcggccga aagttcctcc gtcctctgca ccgacggcga aaacaccgtc gcgtcggacg    4200
cgacggtgac ggcattatga gcggcggcgc tgtacggcag cggggagaaa agtggcagat    4260
aaatcacgtc aggttcacac gtcgttagcc agcgtcggca tatgaagggc gcgggcggcc    4320
agtacggcct ctgggctgag acaggacgag gcagggtgag aaagaggagg atgggggga    4380
ccggggtggt ggtgctgctg ctgttgtggg tgcggacggt gcgggtgccg ggacagcgtg    4440
ccggcgaacg ttctgtaatc ttccataata aaagtaaaaa tgcccgtctc gtgtcgactc    4500
cgctggatct cgaaggcgtc gggggtaatg cgcatcttgc cggtgccgat gagataaaag    4560
taccacattt tttgacagat gatgcgaatc aagggttcgt acgcttcggc accccagtgg    4620
cgcgtgaaga aggccgccag acgaaacaag cggtgtccgt agagcgtgcc tagggagaag    4680
aggatgttgc cgttgcgcgc caggtcttcg gggaaaacga ccggcaggcc ggtgtggcgc    4740
tgcacaaagc gcgtcagcag tccgccgctc aagcgcgggt gacacaggcg ctggctgaga    4800
cgggcggcgc gcgtttcatc gaacacggcc gcctcaaagt ccagccccgg aaggcctgg    4860
cgcagttcgc ggtacagatg aggccagtag ggttgcggcg tcttgcgact aagcacggcg    4920
tggtccgaga cacccaggtt gttcatggtt tcgcgcagta gcagcgtttc gagaccgcgg    4980
tgaaagagga ggacgcagat gaggcgtacg atcttgagtt cttccaaacg cagcgagctc    5040
agcggctgtc cgcgcgacat cttctcgcta atctgtaata ttagatgatt ggcgcaagta    5100
aaggagaatt tgcccgtgcg gacccgcggg acggcggggt tctcttcgtc gcgggccatc    5160
atcgttcgct cggtgagcgg gtagcgacgg tgacgacaat gacgatggac gagcagcagt    5220
cgcaggctgt ggcgccggtc tacgtgggcg gctttctcgc ccgctacgac cagtctccgg    5280
acgaggccga attgctgttg ccgcgggacg tagtggagca ctggttgcac gcgcagggcc    5340
agggacagcc ttcgttgtcg gtcgcgctcc cgctcaacat caaccacgac gacacgccg    5400
ttgtaggaca cgttgcggcg atgcagagcg tccgcgacgg tcttttttgc ctgggctgcg    5460
tcacttcgcc caggtttctg gagattgtac gccgcgcttc ggaaaagtcc gagctggttt    5520
cgcgcgggcc cgtcagtccg ctgcagccag acaaggtggg ggagtttctc agcggcagct    5580
acgccggcct ctcgctctcc agccggcgct gcgacgacgt ggaggccgcg acgtcgcttt    5640
cgggctcgga accacgccg ttcaaacacg tggctttgtg cagcgtgggt cggcgtcgcg     5700
gtacgttggc cgtgtacggg cgcgatcccg agtgggtcac acagcggttt ccagacctca    5760
cggcggccga ccgtgacggg ctacgtgcac agtggcagcg ctgcggcagc actgctgtcg    5820
acgcgtcggg cgatcccttt cgctcagaca gctacggcct gttgggcaac agcgtggacg    5880
cgctctacat ccgtgagcga ctgcccaagc tgcgctacga caagcaacta gtcgcgtga    5940
cggagcgcga gtcatacgtc aaggcgagcg tttcgcctga gcggcgtgc gatattaaag     6000
cggcgtccgc cgagcgttcg ggcgacagcc gcagtcaggc cgccacgccg gcggctgggg    6060
cgcgcgttcc ctcttcgtcc ccgtcgcctc cagtcgaacc gccatctcct gtacagccgc    6120
```

-continued

```
ctgcgcttcc agcgtcgccg tccgttcttc ccgcggaatc accgccgtcg ctttctccct    6180
cggagccggc agaggcggcg tccatgtcgc accctctgag tgctgcggtt cccgccgcta    6240
cggctcctcc aggtgctacc gtggcaggtg cgtcgccggc tgtgtcgtct ctagcgtggc    6300
ctcacgacgg agtttattta cccaaagacg ctttttctc gctacttggg gccagtcgct     6360
cggcagtgcc cgtcatgtat cccgcgccg tagcggcccc tccttctgct cgccagcac      6420 cgctgccttt gccgtcttat cccgcgtcct acggcgcccc cgtcgtgggt tacgaccagt    6480
tggcggcacg tcactttgcg gactacgtgg atccccatta tccggggtgg ggtcggcgtt    6540
acgagcccgc gccgtctttg catccgtctt atcccgtgcc gccgccacca tcaccggcct    6600
attaccgtcg gcgcgactct ccgggcggta tggatgaacc accgtccgga tgggagcgtt    6660
acgacggtgg tcaccgtggt cagtcgcaga agcagcaccg tcacggggc agcggcggac     6720 acaacaaacg ccgtaaggaa accgcggcgg cgtcgtcgtc gtcctcggac gaagacttga    6780
gtttcccagg cgaggccgag cacggccggg cacgaaagcg tctaaaaagt cacgtcaata    6840
gcgacggtgg aagtggcggg cacgcggtt ccaatcagca gcagcaacaa cgttacgatg     6900
aactgcggga tgccattcac gagctgaaac gcgatctgtt tgctgcgcgg cagagttcta    6960
cgttactttc ggcggctctt ccctctgcgg cctcttcctc cccaactact actaccgtgt    7020
gtactcccac cggcgagctg acgagtggcg gaggagaaac acccacggca cttctatccg    7080
gaggtgccaa ggtagctgag cgcgctcagg ccggcgtggt gaacgccagt tgccgcctcg    7140
ctaccgcgtc gggttctgag gcggcaacgg ccgggccctc gacggcaggt tcttcttcct    7200
gcccggctag tgtcgtgtta gccgccgctg ctgcccaagc cgccgcagct tcccagagcc    7260
cgcccaaaga catggtagat ctgaatcggc ggattttgt ggctgcgctc aataagctcg      7320
agtaagagag acgctatatt tagggcttcc ctctcttttt tttctacacc gtgataccct    7380
aataaagcac accgcggtta ttatcaacgt ctctgtgttt ttattattta gaataaata     7440 cagggaatgg gaaaacacg cggggggaaaa acaagaagt ctctctctag atgcggggtc      7500
gactgcgtgg ggtgctggaa gtggaagcgg tgctgatggg tgagggtcgt ggcgcgggca    7560
cggaccgcaa cgtgctgctg atgtctgccg cggtacgcac gtcgccgtcc atgtcgctgc    7620
gcagataaga ggtaggtcgt agtgcggcgt gctgcacgct caccgttaat ggtaccaagt    7680
cgtcaaggct cgcaaagacg tgccacgagg ggatgacgag cgtgagagcc ccgttgttac    7740
cgcttcgacg tctttgtccg gtcaggatca gtgccgggga cagtccggct tgggtgtccg    7800
agtcctcgtc gccgctggct tcctcgaagc cggcaaacat ggcttcggac agggggtcg     7860 gcgtcggtgt ggaggagagg tcatcttcgt cgtcctcttc ctcttcttcc tcctcttcct    7920
cggtgggtgg taatccgggg gactgcggga gaaactcgga gacggcgccg cgcatgacgt    7980
tgctccgtga aaagagaccg gcgcgcagct gcacctgggg acgcttgatt ttgtccggtt    8040
taccgggtgt gagagtccaa aacccacggc ggaaaaagtg gatgcggcct agcggctgtc    8100
ggtgttccaa atgaacggcc tgatcgccgg tcagcgtgac gcggagggtg attcgcacac    8160
gatcgggtag cgggccggct tctatggaga cgcccgggat gttttccggg aaaaagatgg    8220
tgtcgtgagt ctgattggtc tcgaaagcat tctggatctg cacgatgtac tcgggatgta    8280
tgcgcgtcag cgtaaaactt ttgggaatca acagctggaa gccgttgtcc ggcaagcgtc    8340
gtaggtgcgg gtacggattg tgtcgcgcca ccacctcggc gcgatgcgtg taaaccgaaa    8400
agtgcagaaa cacgctggtc ggcgggtgcg gtgagtcgtg atgcagaaac agcatgatcc    8460
```

```
attggcctcg ttcgtccgtc tccgttttgt ggatgtacgt gttagggtcc gaacaggcca    8520
gctgctccag ggcgtctacc agcgtcagcg ggatggcgcc ggcgcgaaag gcgaactggc    8580
tgacaaagat ctgccctgcc tccaaactgc tgtcggttct gcggcgccag ttcggcgtta    8640
cggtcagtcg cacggcccag tggtgagccg tgcggcggat gatggcgcgc gcttccattc    8700
gcggccgatt ttcttcgccg ccgcgccgct ggctctgaaa gaggtgcagt ccgctaacgg    8760
gcacgcggtc cagcggcagc gcaaaggcca gtaccgagac cgtgttgttt tctgagcctg    8820
gcgtcaggcg tcgtgggcca aagttgttga ggtccaccag cagtcggtcc tgttcgccca    8880
ccacgcagcg gcccttgatg tttaagtcgg tcaggtctac ggtgtcgtgc ggagatttgt    8940
tctcctgaaa acagcagaga accgagggcc ggctcacctc tatgttggta cgcaggtcca    9000
ggagtcgcag acgaccggct tccagcgagc cgccttccac gttggtgatg agccgaagca    9060
cctggcagtg caggcgacca aagcttccgc tggcggcttc ggcctcgctg atcgcggccg    9120
cttccgacga gggtccctca ccgggcgagg acgatgcctg agacattgcg aaggcgggat    9180
gggggggaggg tcagggatg cgcaaaggtg aacgggtctt cgtgggaggt cgggaagggt    9240
tccggcaact gtcgcaaata tagcagcggt gacaggtgtg cggccaaaa gttgcgtgtc    9300
tgagtggacg tgggtttta tagagtcgtc ctaagcgcgt gcggcgggtg gctcaacctc    9360
ggtgcttttt gggcgtcgag gcgatgcatg gcccgggcaa ggcgtcttgc cggtggcggc    9420
gacgtttggg ttgcgcagcg ggctgccata cgccttccaa ttcggcgaag atgcggtaga    9480
tgtcgttggc gtcccagaag aattcctggt acttcagatt ctgaccctga accgtagcca    9540
ccatgggcac caggttgcgg gccaggatgc cggcctgcca gggcggccag gtgaacacgg    9600
ccggattgtg gatttcgttg tcggaatcct cgtcggtgtc ctcttcgggc gcgacggtgg    9660
actcggcctt aaggcggccg cgtgtcataa cgcccgacgt gcacgccgtc gccgaggatg    9720
ctgatttgcg tttgcggccc gcggaagtgg aggcgcccgc catggcgccg ccgccggtga    9780
cgcggggcgt cttgcgctcg gtggttacga gttcttcgtc ggagtccgat ccgctggtcc    9840
agacgtcgtc gtcgccctgg gcggcaccct cgtcgtgccg gtcccaggtg tgtcggtact    9900
caagcttgcc ctggatgcga tactggctgg tgaaggtggg gtgctcgctg tactgaggcc    9960
cgcgctgcag cagcaagtcg atatcgaaaa agaagagcgc agccacggga tcgtactgac   10020
gcagttccac ggtctcgcgt atggcttgta cctccaggaa gatctgctgc ccgttcatca   10080
acaggttacc tgagatgctc aggcccggga tgctcttggg acacagcagc ccaaaatgct   10140
cgtgtgaggt aaaagccaca tccagcatga tgtgcgagat cttgcccggt ttgattatca   10200
tattttggg acacaacacc gtaaagccgt tgcgctcgtg ggggcgcatg aagggttgcg   10260
ggttgcgggt catcgtcagg tcctcttcca cgtcagagcc cagcgtgacg tgcataaaga   10320
gcttgccgga gggcacgtcc tcgcagaagg actccaggta caccttgacg tactggtcac   10380
ctatcacctg catcttggtt gcgcgcgtgt tctccatgga gcaaaccagc tcgtgcgcgc   10440
acaccacgtg ccgcagtgcc acgtccttgg tgggaaacac gaacgctgac gtgtagtaga   10500
cgtcgggctc tttccactgg ttctgctgac gcgtccaggc cagtcccgag accgtgagac   10560
gcgcctgcca catctgcttg cccgacgcgt gaatcacagc gtcagctacg gcaggtgtc   10620
ggtgtttgcg ctcggccgcc gacgggtagt ggtgcacgtt gatgctgggg atgttcagca   10680
tcttgagcgg cagcgcgtac acatagatcg acatgggctc ctggctgggg cagatgcttc   10740
ggcccgtggg gttgtgcacg ttgaccgaca cgttctccac ctcgctgccc gtaaagtacg   10800
tgtgctgcac ctgcagctga ttgtcgccgc ggtggcatgg cgtcgagtcg ggcgtgtact   10860
```

```
gcgataccaa gatcagcgag ggctggctca cgcgtacgtg gatacccgtc tgcaggagtc   10920
gcgtctcgtg cggcagcacc ggcgtatcgc cgcgactaaa cacggctttc agcacgtgcc   10980
ccgaaatggg acccagtacg gatatcattt cgggacaacg gcgaccgcgc gactccatgc   11040
tgcctgcgcg tacgggtgta ggcgactgag cggcgcgccc tctgcggccg ccgccttaca   11100
taggcaggca accaaacgcg gaacccgaaa taaaaacgtt ctacacagag acaaccgcgg   11160
attattgagt gtcttttttt attacaaaaa aaagaggcga agccccaccg tcaccacacc   11220
ccatcacaca ccaccaccga tttttttttg ttttaatccc gtatggcgcg gacgcctagt   11280
gtccgtttcc cattatcagg gtcctctgtt tagagatcgc cgcagaccat ggctaaagtg   11340
acaggactcg tcttctctgt cgtatttttcc gtaagcttac agtcttgcgg ttccgtctcc   11400
ggggacgcca gtcgcatggg cagcaggtcc tccagcgcga tggaagcgcc cagcaccgag   11460
agctgctgtt gcgacggcga atgggatgtg gaccgcgagt gtagcgtgga tttgacttgg   11520
tgcgtcattg ctgacaggca accccgattc agcgtatgct ttgacgagat aaaatagagg   11580
cgccccagga gcgcgtcccg tgggaacgtg gcgccgttct cgtcgctcac cagtacggtt   11640
aattccaacc aggagcgcgg tagccagacc gtaacgggca ttttgagtcc ctgacggttg   11700
tgtggtacaa aaacacccag ataaggcccg taaaagcggc ggtagatacg taacgtgtgc   11760
gagttcttca gcgtcaattc gtaagggacg cgcacctcca gtccctcgtc cgccgcgccg   11820
gagcgtggcg gtacaaagta aggcagtggc gcgtccgaaa agaagggtcg tcgcaccgtt   11880
tcgcgtcgca gccgcaggcg aaacgccact gggtcggctg gcgcctcggt gcggtcgcag   11940
gtcacgttga aacgtaatat gccgtcttgg tatagcgtga gtgacgacag cgtcaggtcc   12000
ggcggtgatt cgttcgggtc tagctccaat cgtccaaaga cggagggtcc caatgtcttg   12060
gccgtggttt ccgagaggcg cgccgagata cggctggtga gtccacgcgg ccccgagatg   12120
ccgccttcca ctcgatgcca gcacagcgcg tgtcgtacgc gcaccgtcag cgtgggcgtc   12180
agatccgcgt ccgttgattc cgcggtatca gcgacggaag ccgcgttctc cgttacgttg   12240
tttatatcca gcgtcggctc gaacgtgagt tctggcagat gcagcgccag acagtcgtgt   12300
aacgccgtgt gatgcgcggc tttacgtcgt agcggtagcc gtttcaacag cggcgtgatg   12360
atacggagcg cgaagagatt gagtgatagg cgcacgatgg ccatgcgcgt cagttgttgg   12420
tcaattaccg agcgcaggat atggcagcct gggcgtgcgg gaaagagaga gaaggccggg   12480
cgcacgtcag aatcctcgtt agagaccacg catagaatgc cgcgttcacg atcgtcgttg   12540
cggtcatcct cgtcctcttc tttcttctct tgttttttcct ttttttttctc gggctcgtgg   12600
gaagccgccg tttcttcttc ttgcaacgtc gcggggcgg tttgagactc gtcgttcgct   12660
tcccccaatt gcagcggcgt agagagcaga atctggaagg gatcccgcaa ttcttcgggt   12720
cggaggtcga ggtgcaactg gatcagatgg taggtgccgc ggtgcacccg aggctgacgg   12780
atgtcgtgtt tatccgtcag tgtgaggatg gtctgcggcg agccgctgta cttgtccagc   12840
tcgtccggcg ttttcaggag gagactgtcg tcgtcggtac tggcgacgcc catcatggtc   12900
gtggtggtag tggtggcgag gaaagtgagc ggcggcgccg acagagctcg gcgttggcgg   12960
cggcattttc cgctgtgtcg gctgctattg ctgccaacgc caccgccgcc gcctcgtctg   13020
gctcgtggcc ggcgggcccg attccgaagg ttggggtcga cgcgtggcat gcttggtgtc   13080
tgcgggcgcg agagggccgg ctcagccttt aaatatgcag gtcgcggatt tgttatcggg   13140
tgaaacgtca cacaccgtga agacgacctg ttcgcggatg aggtcatcca gctgtcgcag   13200
```

```
catgacgaaa agcgccgaca gccgcgcgat ctcgtcgtcg ggcgacacgt gctgcggccg    13260
cgcgggcgtg cgcggctcgc cgacgctgcg ctcgcgtcc agccgcatca gcagctcctg     13320
gcacttgacg agcagcatgg agctgtcctc tagcgccaac ttgcgcacgt aggtcatggt    13380
cagctccgag gctaggttgg ccaccatgga catggagagg caggcggtct tcatgtcgat    13440
cagcaggtgc tggtcgatga ccggatcggg gatggtgaag gtggcgtcgc gaaaagtaat    13500
ggtctgcagc tgctgcacgg cagcctttac ctcctcgtac gaacggtcga gcgagaagag    13560
gcccatgatg agtagtcgct ggttgatttc cagcgccagt ggcatgggta cgatccaggg    13620
cagcaccagc tcccactggc ccagcgtcag caggttctcg cgcgccagcg gtccgtggaa    13680
gagcggcggc agcacgcata gcgcgtcgcc cttctcccaa gtcacgggtc ccgtgttgag    13740
gacggtgtag agcagtccgt gcgtgggtac gtgtaggagg atctggttgc cttctacgcg    13800
ccgcatcaac gtcagcgtca tattgcgcag caggccgcgc agtcgtacgt agccgcgggt    13860
gtgatctacg aactggtgta ggcccagctg gtagtgcttg atgagatgta gacgttgcgg    13920
aatgggcaca acggccgcta ctagcttggt cagtttgcct acgtcggcga tgctgagctt    13980
gtggtcgaaa gtgcagaaga tgttggcctc catggccgcc atagcggcgg tgaaatcctg    14040
gccgcgacgg aggagaggca gagacgaaca acgtctgcac cgggcgcggc gtcagagcga    14100
gcgtggcgcg tccgggcccg cgtttgcgtc taggtgactc gccgctaacc tgcggtcgtc    14160
gccgtcctcc tcaccggacg gcctcacgag ttaaataaca tggattgctg cagcgggatg    14220
atttcgccta cgacgtagtt accaaagtgc gtttcggacg tagcaaaagc cccggcgcca    14280
cccttgagtt tggtctccat cagcgccagc gtggtggtgc tgaggatcgg tagcgcttcc    14340
tgcgtcagac ggcacgggtt ttcgatgagt tgttccgtgc cttcgacgca gacgtactgc    14400
gtgtccgtgt cgccgcggat gcagtccttg gcgcgtagca ggtactcgtc gatggttttg    14460
aagagcgttt tgttggccgc gataatctct tctgtgttaa agtactgcgc gcaagggctg    14520
tagaatttgg agttgtagcc tagacgttcg cgatgtcggg tgttgtagag tacgtcgctc    14580
agacagccgg cttgcgaggc ccaggggttg tgtgtggccg cgaaagtctg tgcgtccgct    14640
tcgcgatggt cgtagatggc cttggtggcg gcctccgtgt cgtacggatc gacggccagc    14700
atgcaggagg cacgcccgcg cgggttgttg gggatcttaa agtaattaac gtccatcgtc    14760
accggcgtaa ggattagttc gcacgcggcc ttttgtccgt gcaccgtggc ggcggcattg    14820
cgctcggaca tgctgccgaa cgtcagcata gagatggtct ccgtgtctaa cagttgcggc    14880
cgttctacgc cggccgcgtg ccggatccag cggtccacct cgtcgtgccg gtacacgttc    14940
atagggaaga cgcgaaagag gtcctgcacg cggacgccca tgtcggttcg cacgcggttt    15000
acgtaggcta cgcaggtatt tgacgtgtaa cccagaccca tgtctacggt gttaatgttc    15060
tgcgtgacgt ggtacgtagt gctgatgtcg cgttcctcct tggtcacgat agggttgttg    15120
atgataactg acgtgcatga tttgccgctg tagagcagca tgtccacctc gaaggtgtcg    15180
gtgcgtacgg ccgtgagtgc gaatcccggg tggatgtgcg ccttggtctg cagcaccagt    15240
gaaactggtg agatttttgta taacatgcg gccagcgtca tgactgagtg caacacgttg    15300
ggacaggtgg ccgagtaacg cgaaaagggc gagcgcagcc agttgtggta ctcgtgcgcg    15360
aaggctgtgg gtagcgggaa accaccgtcg tgacggtgat agtgcgggaa ctcggtcacg    15420
tagcgtttaa tgtcgtcgct caacgccgcg cagatggtgg ggtttgagta gaaacggtgg    15480
aaaggtacgg gtaggctgta ctcgatcaac gtcttaggcg ccgtcacgac gcagcagccg    15540
ttgtaaagca cgtgctgacg tgagataaag tccggcaggc cctgacgctg cgcgtggtcc    15600
```

```
agaggcgcgc gcacttcgag caccttgacg tgctcgccca cgaattgcac ggccaaaaac    15660
agttcacgac aggcctgcag cagcggcgta tgtgcgtcgg tggcgacgtc ctccaccagc    15720
tcggtcagca tctcgcctac ggcttgacgt tgcgccgcta tcgagtcttc ggggtgaca     15780 ccgcttgtgc tctctttcga cgtcgtacct gacgtggaga ccgcggtggc ggccggcatc    15840
aggagaaacg ccggtcggta aaagaggtct actagcagcg tcttgaggtt gagtcccagg    15900
ccgcaggccc ggttgttggt catggcgggc atgaggcaga gataaaagac cttttgtaac    15960
gtccattcgt cgtcggtggc acggtaatcg tccacaaaca gcggctcgtc ggcatccatg    16020
gcgcccaaac gcggtacgtc cgaaacgccg tggtgtcgcg cctcgatgtt ggccgggttc    16080
aacggttgcc ggtcggccac tacctgtacg ccttccatgt tacgcggcag gtgcgtaacg    16140 aagggggggcc acagccggtg gtcgtgcagc gcgttcacgt aagccgatag cggttcctca    16200
gccagttgac cgttgttaag tcccggcagc gctgagatgc gcgttaccag acgcagcacg    16260
gcgaccagat tgcggtagtg aaagagcaac tgcggtggta gggcgccatc agccaggtgt    16320
tcggcgatca acgtcaccag cgcgtagctg tgcgcaaaaa ccagcagctg acgtgtgtga    16380
aacatgttga cgatacaacg tgctacgaaa gtgcggatta gcaaaaaagc gtcgacgttg    16440
ccgtgtacca gcacgtcgac caggtagcaa agctcggggt aattgggggct tgtcacggtg    16500 gttttgaaaa gtcgcaacgt ctcttcgtag tcggtggtg gccgcagtcg catgtgttcc     16560
atgatctccc aggtgcgcag ttcgtggaag gggcccggtg ccagtccatc tggcaaatta    16620
ccgatgacga tacgcggtgt acacagcgcc accgtttcgc tgttttcctg gcagtgcgta    16680
aagtcgaaga aggggtgcag ctcggtgtag agcgtgatgt tgcccacctt gtagaagtcg    16740
gtgaccacaa agtcctgctt catttcgttc accgtgcgcg ggacctcgcg tcgtacgcgg    16800
taaaaatgcg gtatgcggcg cgccgcaccg cccatgggtt cctgctgaaa acgacactcg    16860
agcagtcgtt gcatgcgggg ttccgagggc ggtccgcgtt ccgtgaaggt ctgtagacag    16920
ggcgcgggct cgtgcagcac cgggtggcac agcgtcttga gcgcgtccac aaagtctatt    16980
ttttgtacgg cacggtcccg gtttagcagg taggccgtgg tgggcaacgc gttgcgaacg    17040
gtgtcgttaa gcttaacttt gctttccacc gtggtgtaac cgcgatcctc gggcagatac    17100
agccctacgg ggaagaaaaa cgtcaggtcc acgttacgtt ctagcggatc tttggtatcg    17160 gtgttttttgt agacgcgccg caagttttcc ataatcaccg ttttttcgcc cagtcggatc    17220
acgtccatgc tcagcggcgt taagctgtgc gccccggcct gcgaaagcga gtcgttgggc    17280
aaatgcggtt ggcccgaagt cagatgagcc ttgtacgagt tgaaatcggc caggatcgag    17340
tgataggata tggcagtgac ggcattttcg ggactgagta caaaattgcc gtaggtggcc    17400
ggcgccgaga ccgtttcttt ggtgatgtgg cttgagagca gcgacatgat gatctgcata    17460
acgttggccg tgcttaccat cacgccgctg atcttggccc ccgagctcgt ggtgtacgtg    17520
gtggggttgt ctaggatgct atcggtggcc gcttcggcca gacgcgtgag gaacttgagc    17580
acatagtcgc gatcgcgcgt gcgattcagc aaaaagagcg tggccagcat tttggccttg    17640
aagctctgca agatgttgct tcgctggatg cggttcagtg cctgtcgcgc cagtgtggcg    17700
ttttctacca gcgtctgcac cacaaagtac ggcggcgcct tgcgtagcag tgtctgtaaa    17760
aagctgtgaa tcaagccgcg ctccatggcg tcggccgtgt ttttaagcgc gcgcagcacc    17820
gtgtgcatgg cttccacgtt gaggatcttg tccaagatgg tgccctcgaa tgtctcgcgc    17880
agatacgtga ggcaggctgc gctgagctcg aaggggatgg tgatggggga tttttcactg    17940
```

```
tatttggtga ccataatggt ggtctgacga ctagtgggca aaccggcgcc gctggccaca   18000
cgcggcacct gcacgtggaa cagcattttg cccgtagtca gtttattgag gtcgtggaac   18060
ttgatggcgt gcgccgccgc ggccaagccg ctggtcaaaa aataaaccca ttccaggcga   18120
ttgcagaagg tgccgaagat ggcttcgaag tgaatattgt aacgctcggg gtcatcgccg   18180
tagtagatgc gtaaggcctc aaacatctcc tcgccggcgc tggtcttgac gtgcgtcaga   18240
aagtcagtgg gaatgcctac tttaggcagg agctcgagcg ccgaccagtt ctccatcgcg   18300
gcggcggcgt gagcgcgagg cgtcggagct cggggaaagc agcgcgaccc ggagaatggc   18360
cggcgctgcg ccgcgccgcc tcggctgtga cgctctaata gtcgttggcg gctccgctat   18420
gccgcgccgg gttttacacg tccccgtgca cgttcgcgcc tgcaacctca cccaagagct   18480
atcgacgggc gaggacgccc gcttttgtcg tccgcgaccc gttaacgtcg aacgggtgcg   18540
cgctgttttt gcggctctct accgtgcctg tccgatacac gtgaggaccg agcccgagcg   18600
tgtcaagctg gtactgggtc gtctgttact gggacccgtg gccgtaccct gttttttgcga   18660 cggtgaagtg gagggccacg gtgaacatct ggtacctacg acgcagtttt gtcgcgggcc   18720
gctgctctac gtgcaccgac gttgttgttg cggatccgtg accgccgggc gcgcgctgtc   18780
ctaccacgtt ctcgaaaacc acgtggccac gcatgtgcta cgcggattgc tctcgctgac   18840
ggaatggaat cgagaattgc cgagcctctt ttgcgactgt cctggcggcg gtggcgcctc   18900
gggaaccgag gaacgctacg ctatggcctg cctgccgcgc gacctcagcc tgcacctgga   18960
cgactatcct tacctgatgg tggaaatcgg acgcgtactc agtgtcagcg aggtagacga   19020
ctacgtaacc gccgtctccg gctacctggg cgaggccgcg gcgccgcgca tccaggttca   19080
ctacaagctg ctctttggac tcaacgtgcg tccgcaagcg ccgtgcgcgt tggacgctac   19140
acgcgacttt tttctgctgg agctgcaaaa gctttggctg ggcgttgaat atcaccacga   19200
agtcacgtcg gagttttttcg gtcgcgtact ggctcagctg catcgcgacc gcgcccgcgt   19260
catgatggcg cttcgcttgc ccgagcagac ggtgtgccac ctgagcacct tcgttctcag   19320
tcgcttcaag cgacaggtac tgtacttcaa gctacaggtg agctacggca agtgccggac   19380
tggtcacgct gacagaagtg ggggaggggg gaacggtgga aatcagggac accacaaccct  19440 actgtgttat cgacgcctta gcgtcacatt tgccgacaca gacacggtgt ggagaaacct   19500
tttctacgtt tattacgaac tagctcggga tctggggtcc catgggacgg aggaccgacc   19560
cgtaagccgc ggttacggtg tttcttgcgc ttcgaggacg tcgcgactgt caccgtcaga   19620
atcgacggtg gtttcggcga acggacacgc gctgtcttcc accgcgctcc cgacgacgag   19680
cgcgggtcac aagctgtcac tgccgcgcga cccggccgca gatcgcgttc gacgttacgt   19740
atgcattatc tcgcgtctca tgtacgctcg gtacggggag agatgcgcta aacactgtca   19800
acggcggtcg gagacgggag aagaggagga ggaagagacg ctggaatcgg gggagactga   19860
cgccacgccc ccatttgact ttacgggggca gcagctgcgc cgggcctatc aggaacaccg   19920
acgtcgtaaa catctagccg tgcagcgtta cgcgccgtgc cgtcgtaagc tcatcggcgg   19980
gatggagttt gccgaggtga cgggcgtgag tctagaccgc atcgccgtca acgctttcaa   20040
caccaaccgc gttatcaata tgaaggctgc gctctcgtcc atcgccgcgt cgggtctcgg   20100
cgtacgcgcg ccgcggcttc ccaagaacat gacccacagt tttgtgatgt acaagcacac   20160
ctttaaggag cccgcttgca ccgtcagcac ttttgtttcc aacgacgccg tctacatcaa   20220
ctcgctcaac gtcaatattc gcggttccta ccccgagttt ctgtactcgc tgggcgtgta   20280
ccggctgcac gttaatatcg atcactttttt tctgccggcc gtggtgtgca acagcaactc   20340
```

```
ctcgctggac gtgcatgggc tggaggacca ggcggtgatt cgctcggagc gcagcaaggt   20400
gtactggacc accaactttc cgtgcatgat ctcgcatact aacaacgtca acgtgggctg   20460
gttcaaagcg gctacggcca ttgtgccgcg cgtctcgggc gccgacctgg aagccattct   20520
gctcaaagaa ctctcgtgca tcaagaacat gcgcgacgtg tgcatcgatt acggtctgca   20580
ccgtgttttc acgcaactag agctgcgcaa ttcgtaccag atccccttcc tggccaagca   20640
gttagtgctg tttctgcgtg cttgcctgct caagctgcac ggtcgagaga gcggctgca   20700 gttggaccgc ctagtatttg aggcggcaca gcggggtctc tttgactaca gcaagaacct   20760
cacggcgcac accaagatca agcacacttg tgcgctcatc ggcagtcgtc tagccaacaa   20820
cgtgcccaag atcc                                                     20834

<210> SEQ ID NO 29
<211> LENGTH: 9094
<212> TYPE: DNA
<213> ORGANISM: Human cytomegalovirus

<400> SEQUENCE: 29
gtaggtaccc atggcgttgt tagtatcgaa ctggtcaaaa aattggggcg taccggtgac     60
ttgcaacgcg cgacggcgta gcgagacggc cacgcgcgag aaagagcaca cataggccat    120
ggcgcggtgc atgggttgcg agaaggtctc gggcggacgc ttctgcagat cgcagacgtc    180
gtcgcgtagc caggcgctca tttgaccggg cttcttgact agccgtttga gcgtgctgca    240
atggtcgccc cagccgtcct ggtggtccag gatgcagccc aggtccaggt tgttgagttt    300
gttgaagagt agctgacgca tgccgcccac cgtctccaga tagggatcgt gcggggttgac   360 gggtagcccg tgcaggtggt ggtacttcat gtagctgagc gtttcgtcga tgatggccag    420
caacgtgtgc aagttgggag cgttgtacac ggcgaagatc ttttccacca ccagcttgcg    480
cagcaacggt tcctccagcc aatcgaactg ttgacgaatg tgcaacaggt agtcggtgtg    540
catgagctcg tcgtgtgaca gcaggatgcg accgcgcggc tgatgatctt gcgggaaggc    600 ggtgggggacc ttgagatcgg cggggtaggg tgccagacgt agactctcgg ccgtgtagcg    660
ctgaaggtcg taaacgggcg aggtagaact cggtgaggta cccgacgagg cggcgccgcg   720
ctgcagacgc gctcttttttt tcttttcgat caaacggctg agttgctgta gttcgtcctc    780
gtccatggcg tccagttcgt cgtcaataag cgccagcatc tgttgttgtt gcggtccggc     840
ggacgatccg tgatgattat tggctgagga ggggtgagaa gaaccgaaag tcgtaggaca     900
actgggaact cggcgacgaa gatgcgtcga atcgccgccg tgatggtgcg gttcgccgtc    960
atcgttgtcg taagacttac cgtagtgggg gttaaggggc accgaggcgg acgcggccac    1020
gcgtcgcttg aaagaggagg acgccctatg tccgccacgg aagcccgcgg tgcccatgat    1080
gatgtgtccg ccggtgcccc cgagtgcgtg gcggagggag ggtggaaggg gaggaggata    1140
gtggtccgga tcgccttcgg tatcatcgtc tttgctgtag cggggtcgtc gtgcggggac    1200
gcagggtcgg tgatgatgcg aggcggcgcc gacggtatct tccgcgagat ggtgttcgct    1260
ggcggctgct ccgttccgtg tcgacggcga ggttggactt cgctcgcgtc ggaacttccg    1320
tggcacgggt tcgtaatcca gacagaagcg ccgtgcgcga cgggcgcggc gttcgcgctc    1380
gctcagggaa gataacgacg gagcgtcgtg acggccgcgt gagtgcagct ccatggccgc    1440
cgtcgctagg aaggtcacgt tcgggcacgc tgatgtatat atagatgaga ccgctgccgg   1500
ggggcgggtc accggcgccg tggaaagtga ggctcagacg gcggtcgccg gcggcacggg    1560
```

```
cgcgtcgggc ggtctgattt tgatggaaat gtggacgttt ttggcgttgg agtgacactt    1620
tttggtgaaa cagcggctcc agaggctggc ccagagcgcg tagctgtgct cggtgcgcag    1680
gtcgatgaac acctgcacgg tctcttgcgg gttgcggtgc gtgtagttga gacagcgaaa    1740
atcccgcgtg cgcgcgccgt cgcgccgctt gacggccacg cagcaggcgc cgtggggctg    1800
aaagaggagg acgtggggcg cggtaaactg ctcgctgacg tgcggttcgt agtgttgcgt    1860
gaggtgctcg agcagcggcg gccacacgcg ggtgacgacg agccgctgca agtccgtgtc    1920
ggaaatcgca gcggcagtgg cgccgtcgcc accgtacagg tgataggcga gcacctcggt    1980
gagaccgcgg cgtcgataac gcgtcacgtt aagcgagcgc gtctcgataa agttggcttc    2040
ggtcgagggg cagattttgt cgcgtacgct gagaatgacg cgtggcggcg gcgacagggg    2100
caacgcgggc aggtcgtgcg gcgggtggtg gtgaagcagg ttacgcagat ccagttgggc    2160
gcgcacaaag cctagcgggt gttcgcggta ggcgtcgggc acgatgaaca gcggcaacag    2220
acggcgatgc atgaaatagc cgtcgtcttg gtccatttta tacatgtagg gcagacgtac    2280
agagcgtcca tggtggtaga tgcctgtgtc taggctgctc tcgggatgcg agatggggtc    2340
cagcagcgtg tgcagttcgg cgtcgagaca gacggcgtga ttgagcacct gcgccacggc    2400
gcgtaaaacg ctggggtgta cggcgacggt gcaggcgggg aacggcgtga tgatgcgcag    2460
ccccagtttg cccttgcagc ggcagtaagg gggtgacgtg tcaacggagg acgttgtttt    2520
ttggaaaacg ccgttatccg ggacgttatt tttatcctct ttcccgtctt cgtcttcctc    2580
tgtgtcgcgc tcgtcccggt aatcgagata gtcgtcgtca tcgaaaggcg cgccggccgc    2640
gtccacgggc acgctgttgg gtgggcacgc gcttttgaag aaatagaccg ggtgccggtc    2700
ggggtgcgtg tagccaaaga ggctcgccca tacggtcatc cagacgcgtc gtagtccgcg    2760
acatagctca aagacggtgt gtcgcgccag accggagacg ccgtcgcgca gccgtaaatc    2820
aaagtcggcc acaaaattga agacgggcag acgttcgttg aagacttcgt gtcgcgtgta    2880
gtagaactgt gtctcggggc tggtgctggc cacgtcgtcg tcgtgtagcc acacggtctc    2940
ggtcagggcc tcgtccgaga aacgctgtc gggtacgtga cggagcaggt cacgcggaaa    3000
gaggctgcga tgccaggttt cggaggccac ggcgcagaag acgtgctggt cattgggcag    3060
gtgtacgcgg tagacgggca gcggtcgctc cagcagcggt gccagcgcgg gctcgggtag    3120
caggtagcga cgttgcgagt aacgcgttag cgtgccggtg gtgtaagtct gggctgtgcg    3180
tagcgaggcg catagacgta acaagccgga caggagcgt tccagcgggg agaagacaga    3240
ctcggaaagc gtgttgatgc gttcgagctg gcgcgccagc tgcgtggagg tgccgaagaa    3300
gcccgccagg tgcgtgccgt cgatgcggcc gccgtagccg gccagcccca agccgtgcgg    3360
gctggtcgcc gagtgggggg attcgtcgag acgcagtagg tgcgtctcca cgtagtcgtg    3420
tagaaagttg tcgagcgaga agtatttttg catgacgtcc agcagctcgg tggaaagccg    3480
gcggcccaga aaacccggtt cgcgcgtgca ctgcgcttcg ggcgccgcgt cagcgtcgta    3540
agccaccacg cgccggtact cgagcaaccg cgcgcgtgcc agccgcgtgc ggtaggccag    3600
gtagacgtag tgcacgcaga ccgtgtcggg cagacgcgca cgttcgcgga acgcgttgat    3660
ctgcgtgtcc acctgctcta gctcggtgta gtcgcggcgg ttgcgcgcga cggcgtacgc    3720
cacgaaagcg gacacgcgct gacggaaggg cgagcccagt agcagacgcg cgaactcgcc    3780
catggaggcg tgcgtgggga tgatggtgcc caggtcgcgc gtgcagaagc tgcgcacgta    3840
ctcctccacg gtggagatgg tgctgtactg gccctcgaat aggtagtagg ccatggtcag    3900
cagcacctgg ccctcggtgt gcccgaagac gctgatgaac cacgagggcg aggtggggca    3960
```

```
gaggaagacc tggttgagat gacgtagcac ggccgcgtgg tgaaagtaca ccaggtgctt    4020
gaattcgcgc acctcgccgc cgtgttcggg cgagagcacg ggcgtgcgga aaagatgccg    4080
gtagagcggt tgcgtctcgg cctcgtccag actggcgatg agcgccgaga gggggatggg    4140
ctggcgcgcg gccaggtagc gcgagagctg cagcgtttcg ttgttcacgg cgaagacggg    4200
cgccacccgc cgcgagtccg agcacttttg cgtctgtagg cagaagtaaa cacgtcgcga    4260
gacctggtgt ttgaccagca gggggaagac gcagtggtcc gtcggtgtct gcgagagtac    4320
gttggcgact atatgagcag aatcatactc tgttgcgaac agaacgagcg tcatcgtcgc    4380
gccggcacga tgcagctggc ccagcgcctg tgcgagctgc tgatgtgccg tcgcaaagcc    4440
gcgcctgtgg ccgattacgt gctgctgcag cctagcgagg acgtggagct gcgcgagctg    4500
caggcgtttc tggacgagaa ctttaagcag ctggagatca ccccggccga cctgcgaacc    4560 tttctcgcg acacggacgt ggtgaaccac ctgctgaagc tgctgccgct ctataggcaa    4620
tgccagagca agtgcgcgtt cctcaagggc tatctctcgg agggctgttt gcctcacacg    4680
cggccggcgg ccgaggtgga gtgcaagaaa tcgcagcgta tcctagaggc cctggacatt    4740
ctcatcctca aactggtggt gggcgagttt gccatgtccg aggccgacag cctggagatg    4800
ttgctggaca agttctccac ggatcaggcc tcgctggtgg aggtgcagcg cgttatgggc    4860
ctggtggaca tggactgcga gaaaagcgcg tacatgctcg aggccggcgc ggctgcgacg    4920
gttgcgccac tgacgccacc ggcggtcgtt caggggaaa gcggcgtccg cgaggacggg    4980
gaaacggttg ccgccgtgtc ggcctttgcc tgtccctcgg tttcggactc gctgatcccc    5040
gaggaaacgg gggtcacgcg tcctatgatg agtttggctc acattaacac cgtctcctgt    5100
cctaccgtta tgaggttcga ccagcggctg ctggaagagg gcgacgagga ggatgaagtg    5160
accgtgatgt cgccgtcacc cgagcccgtg caacagcagc cgccggtcga gcccgtgcag    5220
cagcagcccc agggacgcgg gtctcaccgt cggcgctaca aggagtcggc gccgcaagag    5280
acgctgccta cgaatcacga acgcgagatt ttggatctca tgcgacacag ccccgacgtg    5340
cctcgggagg cggtgatgtc accgaccatg gtcaccatac ctcctcccca gatacccttt    5400
gtgggttccg cgcgtgaact caggggcgtg aagaaaaaga acccacggc ggcggccttg    5460 ctgtcctccg cgtgaacagc ctggcacgtt ttggaaaacg tacgtgatca cggacacgac    5520
gagtacgggg tttctcatag acgtacttta ttaggtcagg gatgacgggg aggtttcggg    5580
ccgacgtcaa aaataacgtc attcgtgttg acagggcttt ctgcgtcgga gctcttttca    5640
tcttcttctg tctcgtcgac gtcatcgtct accggcgagg gtgtccgttg cagcaacgcg    5700
tgctcgggcg tgtgggtgaa accgatgtcg ggggtgggcg gcacgatcat ctgtcctagg    5760
gggtgactgc ccaccggcag ataggtaaag cggtgggtgg taaaaaccgc tttggctacg    5820
gtggtgtgtg gggagatgca gacggtggtg tgcgaagtgt tgaccaccgt cacgccggcc    5880
gcggtacccg ggagccagat ggtgggtcgg atgatgagat ccgattgact aaactggcgc    5940
acgcccacta tgagggcgca gataccgggc gcgtgcacgt aggccgcgtc aaaatagacg    6000
gtttgcgtgt gacccggacc gatcaccagc gtctgacggg tacgtaacga aaagaaacgg    6060
tgttcgttgg gcggcggcaa gttcatgagc tgccagggtt ctggtacaaa acaggggaaa    6120
acgccgatat cgccttcgat ggtgcccgga aagatggact gaaaagtgtc gttgaggttg    6180
acgacatcca actgcgggac ttgcagcctg gattccagca gctcgggcat gcaaacgaat    6240
tgcgcgtcca ggcatttgta aaaggtaatg ccgaaaaaac cttcggggat atagaggctg    6300
```

```
acgcccagcg aggtgggcac tttgcgctcg cgtgatagcc aaatgatgtg tttattgtaa    6360
aaggccagct gcgtgtggca ttgtttgacg atgaaactgg aaggcatcca cttgtaagga    6420
actttgagcg gtgacggtaa tggcgacgac gcttcatcct ctcccggatg ctgctctttg    6480
tcgtatttct cctcggtcga ttgggcagc gtaaatgtgg tttgaaaatc gctatcgcta     6540
gcgaaacgca cgcagtaacg catgttgacg gatttctcgg ctaggatgat ggagcctgat    6600
gacgatgcgg actcttcctt cattattaac gtaggggtct cccagaatcg ctgaaaacgg    6660
gagcgcggca gccgcgacag taccagttga gagtcgattc ggtcggtcaa catcgtaagc    6720
atcgtggcgg tggtgtgatg gagtggaaca cactagtatt aggtctttta gttttatcgg    6780
tagtggcaga gagttctggt aacaattcat ccacgtcaac ctctgcaact acatcaaagt    6840
cttctgctag cgtatcaact accaaactaa aacagttgc aacaacttct gcaacaacta     6900
cgacgactac gaccttatcg acaactagca ctaaactcag ttctaccacc cacgatccta    6960
atgtgatgag acgacatgcg aacgatgatt tttacaaggc gcattgcaca tcgcatatgt    7020
atgagctctc actgtccagc tttgcggcct ggtggactat gcttaatgct ctaattctca    7080
tgggagcttt ttgtattgta ctacgacatt gctgcttcca gaactttact gcaaccacca    7140
ccaaaggcta ttgagggtgg acagatttac agcccggcgg tgttccggcg gggtaaggtt    7200
tacatacgtg ggtgaccgga ggctaaagtt acgaatctca tctagaaaca gcagcgagtc    7260
tagatagtcc cacaggggat ctataaatgt tctctgaaac cccattgatg gtgacgtagg    7320
tgtagttttg ttactatcgg aagctgtttt gttttccacg aacatggttt cgttgtaata    7380
taaggagctc atgtcgagag taccgtaaat agtgtacggc gtttcgttac ggattagtac    7440
gtgcgtgttt ttcataaatt ctgacacggc ggttcggttg cggcttggtt cacaaaaagg    7500
attttgccgg taacgtagag tggtatacac ccacgttgct aggtccctta actgtgtggc    7560
cataatggac ttcataaagc tgctatcagg acgataagca attgtagacg tggaaacccg    7620
ccttgcggcg gtagtaatac tataagtcac gttagtagtg acgttgagag cggcagacgt    7680
tgtataggaa aagtatggcg tagtagtact ctgagttttc ttagcttttt tttcgaattg    7740
ttccttaacg ggcgcttgtt tacgttttag ttttcgcata gtgttttta acttggtgcc     7800
gttaatatac ttggggacgc gaaatagatt ccggctcatg gcgttaacca ggtagaaact    7860
gtgtgtacag ttgcgttgtg cgtaacgtaa aagcagggcg gttaaaccta gaaaataaat    7920
cgtttgacta tctacgttaa ccttagtcgg acccacgtac aatttggtgt tccaacgcgg    7980
tacattgaaa aacatgggt tgaacgtggt gaaattaccg caaccttgtt cgccagtatc     8040
attacgtttg gaaacgttta gcatttcgga aagacaagtc atggaaggca cagtaccaca    8100
aggtgggggt ctgaatgtta tcgttttagc cgtatgattg tactgtgagt aaacgtattt    8160
tgcgggtttt ctaagctggg tactataaaa atcaaaccac agataggtta tactataatt    8220
ctgaatgggg cccgctaaaa tgtagtattg tggaaactct gtcatgttca tagtgagatt    8280
tttaaccggt tgtttactta cattgtattt tgtagaaata gtcgtttcta gttgtctcaa    8340
aatttctaac ttaagctgat ctaatttata tttgcctatc ttagacagta ccaagcccct    8400
ccaaggacga ttataaagcg cttttgacat aactttacag tttatgaaag aaacaagcaa    8460
gaaagatata gatattagaa acaccatctt agggacgtct ctcaccatca tctctttttct   8520
ccccatgaca gaggaggaga ccccgcaccg tccgtctgcc ttgtggtttg gcttgcctgc    8580
gtgtactcac tgctgattct ggtcgttttg ctgctcatct accgttgttg catcggcttc    8640
caagacgacc tagtctcccg caccttggct gtgtaccaag cttgtatcca gggcccgata    8700
```

-continued

```
tgtaaccaga cccataacag tacctcgtaa ataaagacgc acagacctca cgcatatagt    8760
accatcacac cgtgtggcgt gtactttatt acaacgagca agagtgcccc taagtattgg    8820
ggcccgtacc gttttagaag attttgtgtg aatgtcttta actttctgt cccttttctc     8880 ataaactgtc aggttctaca gtcagcatgt cttgagcatg cggtagagca gatagatgcc    8940
gatgatggcc gatagcgcgt agacggacat catgaggaga cgactgtcgg tggcgtccac    9000
gacgacgtca gttacttcta ggaccgtacc gtttttcaaa agcatgaggt agtgagttcg    9060
cggagatgag accaccactt cgttgtaggg atcc                                9094
```

SEQ ID NO 30

LENGTH: 2624

TYPE: DNA

ORGANISM: Human cytomegalovirus

<400> SEQUENCE: 30

```
ggatcttgac ggttgggggg atagccatcc gagctgtcgg aatcctcgtc gcccgagaaa      60
agatcccctc tggtctccgt gagcggcctc acgtcccacg cgctgtcccg acggacccct    120
cccgggctgg ccttggtcac ctgcggggag acgagactga aagccgcgtg acgctgttgt    180
tgttgcggga tgttcaaggg accgctggtc ggtttctgac tgcccgagga taacaggccg    240
ctgaaaatgc tggaaacacc gccaccacta gcggcgccct tgccgctagt tcccggtttc    300
ttgatgggcg taaagatgtt tttctcgtca tcatcatcgt cgtcgtcctc atcggcactg    360
gagccaaaga gcctccggga ggcgctcggt ttacgtgccg ggggcggtgg ttgctgctga    420
cgttgctgca ggttctgctg cctctcctcc caagccttca gctgctgttt ctcacgctgc    480
accacctcgt cgtccacccg tttctgccgc tcgcgacgct tttcctcttc gtcgtaatag    540 ccgacgccg ccgaacgggc agcgtgggct tcggcggccg gtgccagaga accatgggcc    600
tcgaagcgga acggtttgtg tcccttccag ggactggcga tccagctcca gccgtccagc    660
ggctgcgtgg ggacatgttt cttgggtacc gacgagaagg ccgaaccgcc gccgagcgag    720
aggagattgg cgtcatcgtc aaactccaac gacggcgagc gcgcgcccaa aaacgtgtgc    780
gccgactgtg ggaagctgtc cacgtagata tcaaagtcct cgatgagcag ctccaacagc    840
gtgtcggccg agtcgccgtt ttccacggcg tgcttgagga tattgcgaca gtagttggaa    900
tcaaaggaaa ggcacatgcg cagctccttg accagcagct tgcagcgctc ctgaatgcgc    960
gccagacatt tgcgctccag ctcctcccaa gacctgcgca cgttcatgat gagacggccc    1020
gtgtacacga gcttgttgac ggcgttgacc agcgccgtgt tggcgtgccg gtccaggtta    1080
aggtcgagcg gtttcacgca gaacatgtta cggcgcacac cctccaggtt tcttcaatg    1140 cgctgcacct ccgtatcctt gaggtgcaca aaggcgatgg gttccgtctg gccgatggct    1200
gtgaccagcg tctcgcgcac cgacatcttg gccagaatga ccgcgcttac gagcgcgcgt    1260
tccacgatct cggcatcgtg gcgcacgtcc gtatcgaatt cggtacggtc tagcacagcc    1320
aggtggtcac gcgccttacc acgatcaccg aacgggtaag tgtagccgcg acgcgccacg    1380
gccacgcaac gcacctcgaa ctcctcgagc actgaggaga ggtcgggggtt gtgaaaacgc    1440 agctcgcggt agtatcccaa ccaaagcatg agctcgttga acagcaccgt acgccggtgc    1500
aggcgttttt cgccacattt tttcaggatc ttggggtgtg cctcgagatc cacgtcgggc    1560
```

```
ttttgcgtga  gatggcgcag  aaagttgacc  agggctacca  catcgcgccg  ctgtagaccg    1620
ataaactgca  aactcatgct  ggcttttctc  cagaacccgg  aagcgtcgtc  gccccggact    1680
gcgcccgcgg  tctgctattc  gcccacgatg  acaccatca   tccacaactc  ggtgagcgcc    1740
ccacctagag  ggagggggg   tagtttaata  gcggaggcgg  atacgcggtt  ttcttttaag    1800
cgccgctgac  ttgtttcttc  tgttttttcg  ccccgtgtgc  tgttccgccc  agacccgcaa    1860
caacactcct  ccgcacatca  atgacacttg  caacatgaca  gggccgctat  cgccattcg     1920 aaccaccgaa  gccgtactca  acacattcat  catcttcgtg  ggcggtccac  ttaacgccat    1980
agtgttgatc  acgcagctgc  tcacgaatcg  cgtgcttggc  tattcgacgc  ccaccattta    2040
catgaccaac  ctctactcta  ctaattttct  cacgcttact  gtgctaccct  ttatcgtact    2100
cagcaaccag  tggctgttgc  cggccggcgt  ggcctcgtgt  aaatttctat  cggtgatcta    2160
ctactcaagc  tgcacagtgg  gctttgccac  cgtagctctg  atcgccgccg  atcgttatcg    2220
cgtccttcat  aaacgaacat  acgcacgcca  atcataccgt  tcaacctata  tgattttgct    2280
attgacatgg  ctcgctggac  taattttttc  cgtgcccgca  gctgtttaca  ccacggtggt    2340
gatgcatcac  gatgccaacg  ataccaataa  tactaatggg  cacgccacct  gtgtactgta    2400
cttcgtagct  gaagaagtgc  acacagtgct  gctttcgtgg  aaagtgctgc  tgacgatggt    2460
atggggtgcc  gcacccgtga  taatgatgac  gtggttctac  gcattcttct  actcaaccgt    2520
acagcgcacg  tcacagaaac  aaaggagtcg  taccttaacc  tttgttagcg  tgctactcat    2580
ctccttcgtg  gcgctacaaa  ctccctacgt  ctctctcatg  atct                      2624

SEQ ID NO 31

<211> LENGTH: 5170
<212> TYPE: DNA
<213> ORGANISM: Human cytomegalovirus

<400> SEQUENCE: 31
agtaaaaagt  agatgatgga  gatgatagcg  tagaccacga  agacggctaa  caccatgtgg      60
cctgtacgca  cgaaaaagtt  gtttccgaag  ccgtagcaca  gggccatggc  taccacggtg     120
gtgttgaaac  caagcgctac  ctctaccagg  ttgacgatga  gcgtgcggaa  ctgcaccgta    180
cctttgagct  tggggtgcag  acgcgagaag  aaaaagagtg  agcgtttgta  gctgcggtac    240
tgcgtgacca  tgctcacgtt  gaaaatggtc  aggcagaaaa  agtgcacggc  ggccatgaag    300
gcgatcatgc  tgggcagccg  aaatgacatg  gtcagtgtga  atagttggaa  cgtgtccatg    360
ctgagaatga  agaggaaggc  tgtgaggctg  tcgcccatgt  acgaaatgtc  gcgtgtcgac    420
tggtttaggc  tcatgccttt  gtccttgcgc  atgctgatct  tgatccagca  taccaggtag    480
tagatggtca  cggctaaaaa  gacgagctgc  atgaacacgg  cgtagcacac  caactgcacc    540
gagtctaaga  aaagcatagg  cgtgtgcagg  tgcattacgt  tgtaggccga  catgttgagc    600
ctttcaaagt  ccacgacgtg  atagtagacg  caggggtagc  ccaggtgcgg  aaaattgctc    660
agcactagat  gcacgctgac  gttgacaaaa  gtcagcacca  tgaaaacgat  agaagcgctc    720
catgtccgtg  tattcacctt  atccacgtgc  gagggggcca  tggcgatagc  ggcggcccgc    780
tcgctcggga  ggcgatgggg  gcgcgccgat  gacgacaggc  tcgcgggtcg  ttaaatacta    840
cgatgggagc  cgccgcggct  cacgacgcgg  tttgagcacg  tccgggcggt  cggtgaaaaa    900
agaccccgcg  ggccttcgcg  actctcttct  gtccgaggat  gaccgctcag  ccgccgctgc    960
accaccgcca  ccacccgtac  accctgttcg  ggaccagctg  tcatctcagc  tggtacggcc   1020
```

```
ttctagaggc ctcggtgcct atcgtacaat gtctgttttt ggatctgggt ggcggccgtg      1080
ccgagccgcg gcttcacacg ttcgtggtgc gcggtgaccg tctaccgccg gctgaggtgc      1140
gtgctgtgca tcgcgccagc tagggtgcgc tggcctcggc cgtgactacg gacgccgatg      1200
agcgtcggcg cggcctagag cagcgtagcg ccgtgttggc gcgcgtgttg ctagaaggca      1260
gcgcgttaat ccgcgtgttg gcgcgcacct tcacgccggt gcagattcag acggacgcta      1320
gtggcgtgga gattttggag gccgcaccgg cactgggcgt ggaaaccgca gcgctgtcga      1380
acgcgcttag tcttttccac gtagccaagc tagtggtcat cggctcgtat cccgaagtgc      1440
acgagccgcg tgtggtcacg cataccgcgg aacgcgtctc cgaagagtat ggcacccacg      1500
cgcacaaaaa attgcgtcgc ggttactacg cctacgattt ggccatgtcg tttcgcgtcg      1560
gcactcacaa gtatgtgctg gagcgcgacg acgaggccgt cctggcacgc ctctttgagg      1620
tgcgcgaggt gtgttttttg cgcacctgtc tgcgtctggt cacgcctgtc ggtttcgtgg      1680
ccgtggcagt gaccgacgag cagtgttgtt tattgctgca gtcggcctgg actcacctttt    1740 acgacgtgct tttccgtggt ttcgctgggc agccgccgct acgcgactac ctggggccgg      1800
acctctttga cgggcgcc gcccgttctt tcttttttcc cggtttcccg cccgtgcccg        1860
tctacgcggt ccacggtctg cacacgttaa tgcgcgagac ggcgttggac gcggcggctg      1920
aggtgctctc gtggtgcggc ctgcccgaca tcgtgggctc ggccggcaag ctggaggtgg      1980
aaccctgcgc gctctcgctc ggcgtgcccg aggatgagtg gcaggtcttc ggtaccgagg      2040
ccggcggcgg cgccgtgcgt ctcaatgcca cggcttttcg cgagcgaccg gccggcggcg      2100
atcgtcgctg gctgttgccg ccgctgccac gtgacgacgg cgacggtgaa acaacgtcg      2160 tggaagtcag cagcagcacc ggcggtgcgc acccgccgag cgacgacgcc actttcaccg      2220
tgcacgttcg cgacgccacg ctacatcgag tgctcatcgt ggatttggtc gagcgcgtgc      2280
tggccaagtg tgtacgcgcg cgcgacttca atccctacgt gcgttatagt catcgactcc      2340
acacttatgc ggtttgtgaa aagtttattg agaatctgcg ttttcgctcg cgacgcgctt      2400
tctggcagat ccagagtctg ctgggctaca ctccgagca cgttacgtca gcctgcgctt       2460
cggccggcct tttgtgggtt ctgtcgcgcg gccaccgcga gttttatgtc tacgacggct      2520
attcgggtca cggacccgtc tcggccgaag tgtgcgtgcg gactgtggtc gactgttatt      2580
ggcgcaaact ttttggcggc gacgatccgg gtcccacctg tcgtgttcaa gagagcgcgc      2640
ccggcgtgct gttggtctgg ggcgacgagc ggttggtggg tcccttcaac ttcttctacg      2700
gcaacggcgg cgccggtggt agtccgctcc acggggtggt gggtggtttc gcggcgggac      2760
attgcggtgg cgcttgttgc gcgggctgcg tcgtcactca ccgccattct agcggcggcg      2820
gtggtagtgg cgtgggcgac gcggaccacg cgagtggcgg cggtctagat gccgctgccg      2880
ggagtggtca taacgcggt agtgatcggg tttctcccctc cacgccgccc gcggcgttag     2940
gtggctgttg ctgcgcagcc ggtggcgact ggctctcggc cgtgggtcat gtcctgggcc      3000
ggctgccggc gctgttacgg gagcgcgtga gcgtgtccga gctggaagcc gtgtaccgcg      3060
agatcctctt tcgtttcgtg gctcgccgca acgacgtgga cttttggtta ctgcgcttcc      3120 agccggtga aaacgaagta aggccgcacg ctgggtgat tgactgcgcg cccttccacg        3180
gcgtgtgggc cgagcagggc cagatcatcg tacagtcacg cgatacggcg ttggcggccg      3240
atatcggcta cggcgtctat gtggacaagg cctttgccat gctcacgget tgcgtggagg      3300 tctgggcgcg agagttattg tcgtcctcca ccgcttccac caccgcttgt tcttcttctt      3360
```

```
ccgttctctc ctccgccttg ccgtccgtca cttcgtcctc ttcgggcacg gcgacggtgt    3420
ctcctccgtc ttgttcttct tcgtcggcga cttggctcga ggagcgcgac gagtgggtgc    3480
gctcgctggc ggttgacgcg caacacgctg ctaagcgggt ggcttccgag ggcctgcggt    3540
ttttccggct caacgcttaa cgagtcacgt aggggaacta cgtgggtaag tgacgtggat    3600
actagtaaaa aaagtgcgtc aaagctctta gcgtgtgacg tggatactag taaaagggac    3660
gtcaaagctc actacgtgtt gcgtgttttt ttttttttcta tgatatgcgt gtctagttcg    3720
cttctcactc ttcctctcct cgttcccagc gcggcggcag cttgggggt gagggcaaat     3780 tggggtagtt ggcgttgagc acgtctagca ggcccaggcc cacgggccaa ccgtccacgg    3840
tcttgcgctc ggtcagcttg aggctgaacg agtgtgcctc gtcctgaccg gtaaggcgga    3900 aaagaagcg tgctaccagc tgcaggcagg tatgccgcgt ctgctggaag agcacgaagg     3960
tagcgggcac gtactgcaca atgtgcggct ctttttcctc aaagagcagg tagagcgcgc    4020
tgcagatcag ccgcctggcg ctgtggtgca gcagccggcc gaagctttcg cgcacgttca    4080
ccgcgtccag gtactggagc aggtcgtgca ggcacttgcg cgttaagttg caattttcca    4140
cgcacgaaat aacggtacag agcgcgaagt gcagcaggtt gtcggctttg acgatgccgc    4200
agcggtgttt gagccgcaga tccgagagcc tcacctgcgt gacggcgtct tcggtctcga    4260
gcaaaaacac ggcggagtag cctagaaagg ccgaggtgca cagcaactcg ctgcggtact    4320
cggccatgga gaccagcagc ccgtgctccg tgtgcagcca cagcttgtcg ccgcgcaccg    4380
taaagtcgag cacttgcggc tccatgatca tcacattctg tctagtgaaa tccgtatgga    4440
cctccagcac gccgcggatc atcagggcct ccatttcgaa atcggccgac acgctctggg    4500
ccgcgccgct cctcgtctgc cgtgatcaag cggcgcggcg cggaccttc aagtgttcct     4560 gggccgccgc tcgaggcagt tcccctttct ggcactccgc ccgccgcttc gcggctcatt    4620
tggcgccgac gcgccttctc gcggctgcaa atcagctcca cgtatcggca aaacttgctg    4680
tcgtcgtagg cggcggccac gatctcgccg aaggagagct gcaggtaggc ctcgggtacg    4740
gggtccagcg tgcccagcgc caggatgtga cacagatagg gcagggtcac gcgctctacc    4800
gtgtaattgg agtagacgat ggcctcttcg gccccttgat gcgtgaccag acgccgtagg    4860
cgaaaggtac ggaaatactc gttttcccac aactgcgtga ggaagcgttc cagcgactcg    4920
gtgccgggca cgaactgcga gaagaagctg ttggccacca ggcggttgtc ttccaccgcc    4980
agcggacgga agggcgccgc gtcgcgcgcc ttgcgcacgg cctccaacac gggcaggtgg    5040
tagagttcgg cgtcgcgcgc gcccaggctc atggagtcct cgcgccgcga ggcgtagcgc    5100
gtgagcaggt cgcgcagttc gcgcacgcga ttctcccagg tctggttaag cgtgcgcagg    5160
tcctggatct                                                           5170
```

ATTENUATION OF CYTOMEGALOVIRUS VIRULENCE

REFERENCE TO RELATED APPLICATIONS

This application is a division of U.S. application Ser. No. 09/724,935, filed on Nov. 28, 2000, now U.S. Pat. No. 7,204,990, which is hereby incorporated by reference herein in its entirety for all purposes.

TECHNICAL FIELD

The present invention is related generally to methods and compositions for treating or preventing cytomegalovirus (CMV) infections, such as congenital CMV disease, CMV retinitis, CMV mononucleosis, and the like, and methods of attenuating pathogenic cytomegalovirus isolates and strains, genetically engineered cytomegaloviruses and combinations thereof, methods for altering the phenotype of CMV viruses, attenuated viral vaccine compositions, and uses thereof. More particularly, the present invention is related to methods and compositions for prophylaxis and therapy of human cytomegalovirus infection, including the use of methods that functionally inactivate a subset of cytomegalovirus genes present in pathogenic isolates of human cytomegalovirus.

BACKGROUND

Cytomegalovirus (CMV) is a widespread herpesvirus in the human population, with between 0.2 and 2.2% of the infant population becoming infected in utero and another 8-60% becoming infected during the first six months of life (Reynolds et al. (1973) *New Engl. J. Med.* 289:1). Although CMV infections are most commonly subclinical, CMV-induced sensorineural hearing loss and fatal cytomegalovirus infections ("cytomegalic inclusion disease") are important public health problems. Moreover, CMV is one of the more common opportunistic infections associated with Acquired Immune Deficiency Syndrome ("AIDS") and frequently produces disease, with recurrent infection occurring in HIV-positive individuals, typically taking the form of retinitis or ulcerative lesions in the colon and esophagus, and occasionally producing extensive necrotization of the bowel with a grave prognosis (Rene et al. (1988) *Div. Dis. Sci.* 33:741; Meiselman et al. (1985) *Gastroenterology:* 88:171). Cytomegalovirus (CMV) infection is the major infectious cause of mental retardation and congenital deafness. CMV is also responsible for a great deal of disease among the immunosuppressed, producing general and often severe systemic effects in patients with AIDS, in organ transplant recipients who have been iatrogenically immunosuppressed, and in bone marrow transplant patients.

It is clear that cytomegalovirus infections are a significant human health problem. Therefore, it is desirable to develop prophylactic and therapeutic methods and compositions to prevent cytomegalovirus infection and/or inhibit recurrent infectious outbreaks from persistent latent infections, particularly for treating CMV retinitis, CMV mononucleosis, and related CMV pathology in human patients.

One approach that has been used to treat herpesvirus infections is to inhibit CMV viral DNA replication. For example, viral DNA replication can frequently be inhibited by agents that inhibit virally-encoded DNA polymerase. The most notable examples of such inhibitors of viral DNA polymerase are acyclovir, ganciclovir, citrusine-I, and the acyclic guanosine phosphonate (R,S)-HPMPC (Terry et al. (1988) *Antiviral Res.* 10:235; Yamamoto et al. (1989) *Antiviral Res.* 12:21). However, these compounds are not completely selective for viral thymidylate synthetases or DNA polymerases and therefore can disadvantageously cause inhibition of host DNA replication at high doses. Moreover, the development of mutant viruses which are resistant to the inhibitory effects of these compounds have been reported, and appear to result from mutations in the viral DNA polymerase (Coen et al. (1982) *J. Virol.* 41:909; Coen et al. (1980) *Proc. Natl. Acad. Sci. (U.S.A.)* 77:2265; Larder et al. (1987) *EMBO J.* 6:169). Thus, while CMV infections, such as CMV retinitis, can be initially treated with foscarnet and ganciclovir, after a period of time CMV replication and progression of the pathological viral infection recurs.

Passive immunization with antibodies (e.g., immune globulin) has been tested in combination with ganciclovir for therapeutic efficacy in humans. Such antibody preparations are obtained from the serum of donors, who possess a high antibody titre to the virus as a result of an earlier infection. One disadvantage of such conventional antibody preparations is the limited number of suitable donors and the poor reproducibility or quality of the various preparations, including potential contamination with pathogens and pathogenic viruses. Unfortunately, the use of intravenous immune globulin in combination with ganciclovir apparently does not produce significantly improved efficacy as compared to ganciclovir treatment alone (Jacobson et al. (1990) *Antimicrob. Agents and Chemother.* 34:176). The safety and pharmacokinetic profiles of anti-cytomegalovirus monoclonal antibodies are discussed in Aulitzky et al. (1991) *J. Infect. Dis.* 163:1344 and Drobyski et al. (1991) *Transplantation* 51:1190. However, none of the reported human anti-CMV monoclonal antibodies have been shown to possess significant therapeutic efficacy in treating CMV infections (e.g., retinitis) in humans.

Attempts to use recombinantly produced hCMV glycoproteins as a subunit vaccine to provide protective immunity against hCMV infection and pathogenesis have not proven to be effective, but remain candidates for additional evaluation.

Thus, there exists a need in the art for effective methods and compositions for inhibiting human cytomegalovirus replication, attenuating CMV virulence in vivo, neutralizing CMV virions, and for preventing and treating human cytomegalovirus infections, and especially CMV infections in preborns, newborns, and immunosuppressed patients such as AIDS patients. For example but not limitation, a suitable attenuated human CMV vaccine which elicits satisfactory immunoprotection against CMV infection is needed in the art. The present invention fulfills these and other needs.

SUMMARY OF THE INVENTION

A basis of the present invention is the surprising and unexpected finding that: (1) clinical isolates of pathogenic CMV variants contain a genomic region ("virulence region") which typically is not present in CMV strains which have undergone extensive laboratory passaging of the virus in cell culture (hereafter termed "highly passaged strain variants") and (2) functional disruption (e.g., deletion or insertional inactivation and the like) of genes in this genomic region produces a substantial attenuation of CMV virulence and/or pathogenicity in vivo. Furthermore, the virulence region of a clinical isolate of CMV is frequently deleted, rearranged, or substantially changed over the course of passaging the virus in cell culture.

In one aspect of the invention, the virulence region is obtained from an early passage Toledo strain and is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates, many early passage CMV strains, and non-isolated pathogenic CMV variants.

The Toledo genomic region which is present in pathogenic CMV isolates and which is typically substantially absent in highly passaged CMV strains (e.g., AD169, high-passage Towne) has been sequenced and several open-reading frames have been identified (PCT Publication WO96/30387, U.S. Ser. No. 08/414,926, U.S. Ser. No. 08/644,543 filed 10 May 1996, each incorporated herein in their entirety by reference). Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants to generate a "Toledo region-attenuated CMV variant"; such Toledo region-attenuated CMV variants have altered phenotypes which generally make them candidates for use in live attenuated virus vaccines for prophylaxis and/or treatment of CMV disease. The invention is, in part, further based on the heretofore unrecognized finding that pathogenic clinical isolates of CMV have a distinct genome as compared to the commonly used laboratory-passaged strains of human CMV (e.g., AD169, highly-passaged Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which typically lack all or part of the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a virulence region of a CMV genome having substantial identity to at least 300 bp, typically at least 500 bp, of a 15 kb sequence present in the genome of the Toledo strain of CMV and absent from the genome of the AD169 strain of CMV and/or absent from the genome of highly-passaged Towne (i.e., more than 50-100 passages). In an aspect, the method functionally inactivates at least one open reading frame present in a genomic region of a CMV genome having substantial identity to at least 300 bp of a 13 kb sequence present in the genome of the Toledo strain of CMV and absent from the genome of the Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO: 1). In an embodiment, the method functionally inactivates at least the open reading frame corresponding to UL 148 as identified herein. In a variation, the method functionally inactivates open reading frames in the region spanning UL138 to UL148. In an embodiment, the method functionally inactivates UL138, UL139, UL140, UL141, UL142, UL143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Typically, such Toledo region-attenuated CMV variants comprise at least 500 bp of the Toledo genomic region or a homolog region having at least 80 percent sequence identity; frequently they comprise at least 1.0 kbp of the Toledo genomic region or homolog virulence region; often they contain at least 5.0 kbp to 8.0 kbp of the Toledo genomic region or homolog virulence region, and can comprise up to a complete Toledo genomic region or homolog virulence region. It is possible for a synthetic virulence region to be comprised of portions of two or more virulence regions (e.g., such as a chimeric virulence region comprising part of the Toledo genomic region from a first clinical isolate with a complementing portion of the Toledo genomic region of a second clinical isolate).

In an aspect, the invention provides a method for attenuating a CMV strain or isolate containing an encoding polynucleotide sequence encoding a polypeptide which is at least 80 percent sequence identical to a polypeptide encoded by UL138, UL139, UL140, UL141, UL142, UL143, UL144, UL145, UL146, UL147, and/or UL148 of the Toledo genomic region; the method comprising functionally inactivating (e.g., deleting or introducing a nonsense or missense mutation) said encoding polynucleotide sequence to produce a Toledo region-attenuated CMV variant. In a variation, all open reading frames (ORFs) in the CMV isolate that are at least 80% sequence identical to the corresponding sequence of the Toledo genomic region are functionally inactivated. In a variation, all open reading frames (ORFs) in the CMV isolate that are at least 80% sequence identical to UL138, UL139, UL140, UL141, UL142, UL143, UL144, UL145, UL146, UL147, and/or UL148 of the Toledo genomic region are functionally inactivated. In an alternate variation, only one or a subset of the open reading frames (ORFs) in the CMV isolate that are at least 80% sequence identical to the corresponding sequence(s) of the Toledo genomic region are functionally inactivated. Such Toledo region-attenuated CMV variants comprise at least 500 bp of a Toledo genomic region and can comprise up to a complete Toledo genomic region (including a chimeric Toledo genomic region composed from distinct clinical isolates or strains).

In an aspect, the invention provides a recombinant CMV virus, comprising a genome having at least 500 bp of a virulence region wherein at least one ORF has been functionally inactivated by a genetic alteration which is predetermined and/or which does not occur in known isolates or strains of CMV regardless of passage history.

In an aspect, the method of attenuating virulence comprises functional inactivation of open reading frames by predetermined structural mutation (e.g., deletion, insertion, missense or nonsense mutation, and the like) of at least one open reading frame, or a predetermined mutation of a transcriptional control sequence that controls transcription of the open reading frame, or predetermined mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by mutation; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by mutation; in one embodiment the structural disruption results from deletion of the UL138-UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AD169. The Towne genome comprises a region no present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 (EMBL accession number X17403) nucleotide numbering convention, operably linked to (2) Towne DNA (DNA substantially identical to a Towne strain, preferably identical to it) from about nucleotides 143,824 to 189,466 according to the AD169 (EMBL accession number X17403) nucleotide numbering convention, operably linked to (3) Toledo DNA (DNA substantially identical to a Toledo strain, preferably identical to it) from about nucleotides 189,466 to about 209,514 corresponding to (i.e., according to) the AD169 (EMBL accession number X17403) nucleotide numbering convention, operably linked to (4) Towne DNA (DNA substantially identical to a Towne strain, preferably identical to it) from about nucleotides 200,080 to 229,354 according to the AD169 (EMBL accession number X17403) nucleotide numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ M.$^{-1}$, typically at least about $1 \times 10^8$ M.$^{-1}$, frequently at least $1 \times 10^9$ M.$^{-1}$ to $1 \times 10^{10}$ M.$^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a highly-passaged Towne genome and at least one open reading frame of a Toledo genome region, typically present in or adjacent to the $U_L/b'$ region of the composite CMV. In an aspect, the composite CMV is a highly-passaged Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV. In a variation, a low passage Towne genome (i.e, less than 40 passages in culture) is used in place of a highly-passaged Towne genome. In an alternate variation, a virulence region from a low-passage Towne genome is emplaced in a Toledo genome so as to thereby replace at least 1 kbp of the virulence region of the Toledo genome with at least 500 bp, typically approximately the same length, of a corresponding region (e.g., substantial sequence identity) of low-passage Towne.

In an aspect, the invention provides a chimeric CMV virus, comprising a genome having a plurality of polynucleotide sequences, linked in conventional phosphodiester linkage, wherein at least two of said polynucleotide sequences are derived from different clinical isolates or strains of CMV. Said chimeric CMV virus can comprise a genome having a plurality of polynucleotide sequences, linked in conventional phosphodiester linkage, wherein a first CMV genome sequence of at least 500 bp and less than a complete CMV genome length (e.g., less than 250 kbp) is at least 98 percent sequence identical to a first CMV isolate or strain, and at least one additional CMV sequence of at least 500 bp and less than a complete CMV genome length (e.g., less than 250 kbp) is at least 98 percent sequence identical to a second CMV isolate or strain which has a genome having a polynucleotide sequence of at least 500 bp which is less than 60 percent sequence identical to any portion of the genome of said first CMV isolate or strain and/or which is absent or substantially absent in the genome of said first CMV isolate or strain. Said chimeric CMV virus comprises a genome having sufficient genetic information to replicate as a virus, typically as an infectious virus, in suitable host cells or a suitable host organism or replication system (e.g., SCID/hu thy/liv mice, human lung fibroblasts, and other systems known in the art). Generally, said chimeric CMV virus has a genome that comprises genetic information which is substantially sequence identical, generally at least 80 percent sequence identical, usually at least 95 percent sequence identical or more, to a high-passage Towne genome; said chimeric CMV virus genome typically further comprises genetic information which is substantially sequence identical, generally at least 80 percent sequence identical, usually at least 95 percent sequence identical or more, to at least 1 kbp of a virulence region of a clinical isolate of CMV or a low-passage strain of CMV other than low-passage Towne; in an embodiment, a complete virulence region (e.g., Toledo genome region) of a clinical isolate or low-passage CMV strain is present.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete low-passage Towne genome. Typically, the chimeric genome comprises at least 500 bp containing at least one ORF having at least 95 to preferably 100 percent sequence identity to a virulence region (e.g., Toledo genome region) of a clinical isolate or low-passage strain of CMV other than low-passage Towne.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete Toledo genome excepting at least 1 kbp of the virulence determining region of Toledo (Toledo genome region), and preferably excepting at least 5 kbp to the entire approximately 15 kbp virulence-determining Toledo genome region. Typically, the chimeric genome comprises at least 500 bp containing at least one ORF having at least 95 to preferably 100 percent sequence identity to a virulence region of low-passage Towne.

In specific embodiments, the invention provides exemplary CMV chimeric viruses composed of genome portions of high-passage Towne and genome portions of Toledo; the exemplary CMV chimeric viruses are designated herein as Chimera I, Chimera TI, Chimera III, Chimera IV, and Towne/Tol 11. In an aspect, the invention encompasses these specific embodiments and variants of each exemplified Chimera wherein the boundaries (splice junctions/recombination joints) between the various Towne and Toledo genome portions vary from the specific exemplified Chimeras by less than 20 kbp, typically less than 10 kbp, usually by less than 5 kbp, and in many embodiments by less than 1 kbp from the specific examples provided herein.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucleotide probe, and the like. Detection of polypeptide species is typically done by immunoassay using a specific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

A further understanding of the nature and advantages of the invention will become apparent by reference to the remaining portions of the specification and drawings.

BRIEF DESCRIPTION OF THE DRAWINGS

FIGS. 1A-1R. Nucleotide sequence of Toledo genome region isolated from Toledo strain of HCMV) (SEQ ID NO: 1).

FIGS. 2A-2H. Deduced amino acid sequences of open reading frames UL130, and UL132 through UL151 (SEQ ID NOs:2-22, respectively). Conventional single letter abbreviations are used.

FIG. 8. Southern blot showing that previous variants of the Towne strain hybridize to the Toledo $U_L$/b' region. Twn•Merck indicates Towne strain from the Merck clinical trial. Twn•MA, Twn•MA#5 and Twn•MA#8 are variants of Towne obtained from Microbiological Associates. Twn•Aviron is highly-passaged Towne obtained at Aviron.

FIG. 9. Schematic depiction of generation of chimeric CMV virus genomes by cotransfection of cosmids containing portions of Towne and Toledo genomes.

DEFINITIONS

Figure 3:
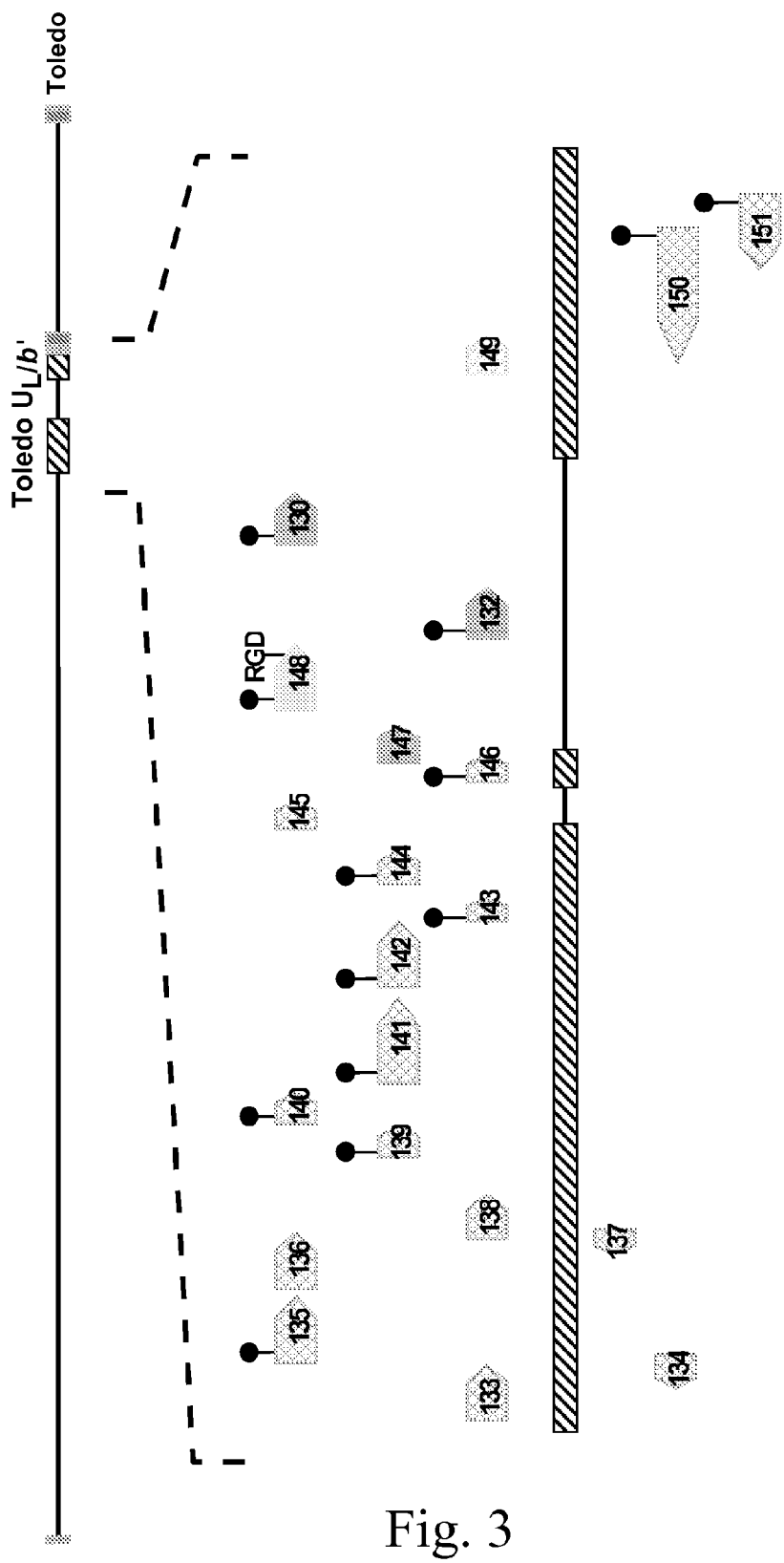
FIG. 3. Schematic representation of open reading frames and their location in Toledo genome region. Top line schematically portrays entire Toledo genome with $U_L/b'$ identified. Bottom line shows enlarged view of $U_L/b'$ region. Arrows indicate polarity and length of open reading frame. Solid circles indicate potential glycosylation sites.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences" sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATAT".

The following terms are used to describe the sequence relationships between two or more polynucleotides: "reference sequence", "comparison window", "sequence identity", "percentage of sequence identity", and substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1A-1R (SEQ ID NO. 1), or may comprise a complete cDNA or gene sequence. A full-length cDNA or gene sequence is defined as a polynucleotide containing the sequence(s) necessary to encode a complete protein product, including a translation initiation codon and a translation termination codon, unless linked to another encoding sequence in a format for production as a fusion protein. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (*U.S.A.*) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25 50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of an open reading frame shown in FIG. 1A-1R.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "analog", "mutein" or "mutant" as used herein refers to polypeptides which are comprised of a segment of at least 10 amino acids that has substantial identity to a portion of the naturally occurring protein The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class TI-restricted antigen recognition.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described herein below. Agents are evaluated for potential activity as specific protein interaction inhibitors (i.e., an agent which selectively inhibits a binding interaction between two predetermined polypeptides but which does not substantially interfere with cell viability) by inclusion in screening assays.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (eg, $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15-25 or more nucleotides, although it may contain fewer nucleotides. Short primer molecules generally require cooler temperatures to form sufficiently stable hybrid complexes with template. In some embodiments, the primers can be large polynucleotides, such as from about 200 nucleotides to several kilobases or more. The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, *Aspergillus* and insect cells. One preferred embodiment employs bacterial cells as the host. Alternatively, the product polynucleotide may serve a non-coding function (e.g., promoter, origin of replication, ribosome-binding site, etc.).

DETAILED DESCRIPTION

Commonly-assigned U.S. patent application U.S. Ser. No. 08/414,926 filed 31 Mar. 1995 is incorporated herein by reference.

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. *Molecular Cloning: A Laboratory Manual,* 2d ed. (1989) Cold Spring Harbor Laboratory Press, Cold Spring Harbor, N.Y.).

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Stockton Press, New York, N.Y. (1989); *PCR Protocols: A Guide to Methods and Applications*, eds. Innis, Gelfland, Snisky, and White, Academic Press, San Diego, Calif (1990); Mattila et al. (1991) *Nucleic Acids Res.* 19:4967; Eckert, K. A. and Kunkel, T. A. (1991) *PCR Methods and Applications* 1:17; and U.S. Pat. Nos. 4,683,202 and 4,965,188, each of which are incorporated herein by reference) and exemplified hereinbelow.

It is evident that optimal PCR and hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology*, Volume 152, *Guide to Molecular Cloning Techniques* (1987), Academic Press, Inc., San Diego, Calif.; *PCR Protocols: A Guide to Methods and Applications*, eds. Innis, Gelfland, Snisky, and White, Academic Press, San Diego, Calif. (1990); Benton W D and Davis R W (1977) *Science* 196:180; Goodspeed et al. (1989) *Gene* 76: 1; Dunn et al. (1989) *J. Biol. Chem.* 264:13057 which are incorporated herein by reference.

A basis of the invention is the unexpected discovery that there are significant genomic differences between clinical isolates of CMV and highly-passaged CMV strains, including differences between low-passage Towne and high-passage Towne, as well as differences as compared to Toledo strain; the identification of these genomic differences, including definition of novel genomic region(s); and the phenotypic significance and biological function of said genomic differences and specific ORFs within said novel genomic regions. Based, in part, on these unexpected discoveries, it is possible to construct and use chimeric CMV viruses which have predetermined genome compositions comprising at least a portion of a genome of a first CMV isolate or strain and at least a portion of a genome of a second (or subsequent) CMV isolate or strain, so as to form a complete, replicable recombinant chimeric CMV genome, with and the resultant chimeric CMV genome being capable of replication in a suitable host replication system and being useful for a variety of uses, such as human or veterinary vaccines, commercial reagents for laboratory use (e.g., as restriction enzymes are sold), use in screening systems to identify novel candidate drugs to inhibit replication or pathogenesis (e.g., virulence, tropism, host range, etc.) of pathogenic, clinically relevant CMV virus types, and other uses such as diagnostic reagents, gene expression vectors, anti-tumor agents, heterologous gene expression systems, and the like.

Overview

An approach of the invention starts with identification of DNA sequences which confer virulence on human cytomegalovirus (HCMV). These sequences can be manipulated to produce a new, more efficacious HCMV vaccine strain with predicted characteristics. Introduction of the virulence genes into an overattenuated strain can improve its immunogenicity and deletion of the virulence genes from a virulent strain can render it safe in humans by decreasing its virulence. Specifically, deletion of genetic information from a clinical isolate called Toledo is used to attenuate an HCMV virus, and in one embodiment, a segment from a laboratory strain called Towne, especially a highly-passaged Towne variant, is transferred to the deleted region of Toledo to act as a "spacer". Deleting genetic information has utility in improving a clinical isolate such as Toledo as an immunizing composition. Removing these sequences from Toledo, which has been shown to cause disease in people, can result in an attenuated virus which may be a safe vaccine candidate.

The Towne strain of HCMV has been used as a vaccine in humans. In some clinical settings, Towne has been used to prevent the disease consequences associated with infection by HCMV (reviewed by Marshall and Plotkin In: *The Human Herpesviruses B*. Roizman, R. J. Whitley, & C. Lopez Eds. Raven Press, New York). The Towne strain is believed to be overattenuated as a vaccine candidate and consequently, is poorly immunogenic. This loss of immunogenicity may have been the result of an extensive passage history in tissue culture. Genetic information in the virulence region may have been lost during passage, particularly after about Passage 40. Variation in DNA content among isolated strains does exist based on crude hybridization experiments. Other investigators have reported minor regions of sequence heterogeneity between two so-called laboratory strains of HCMV, the Towne and AD169 strains. Heterogeneities can exist within HCMV strains depending upon the extent of passages in their culture history.

The public health impact of HCMV infections have not been well controlled by current treatment strategies or available antiviral chemotherapies. Preventive vaccine strategies are likely to prove efficacious because of the observations that seropositive renal allograft recipients are protected from severe HCMV disease and maternal immunity protects the fetus from disease after intrauterine infection. HCMV (Towne) was developed as a vaccine strain by serial passage 125 times in W138 human diploid fibroblasts (Towne 125). It has been administered to humans without significant adverse reactions. However, in one study, vaccinees were directly challenged by wild-type virus and found to resist only low challenge doses of 10 plaque-forming units or less. The consensus view is that the Towne strain may be overly attenuated. One positive feature of the Towne strain is that it has never been shown to reactivate.

One important obstacle to the development of a vaccine for HCMV is the lack of an animal model system that can be used to test the safety and efficacy of vaccine candidates. Therefore, cell culture systems or surrogate animal models such as the SCID-hu (thy/liv) mouse have to be developed to test vaccine strains. Replicative differences in HCMV strains have been described in a variety of cell types and in the SCID-hu mouse model. These differences correlate to the virulence and passage history of the virus. Thus, low passage, virulent clinical isolates, such as Toledo, can replicate better in the human implant of SCID-hu (thy/liv) mice and in cultures of human endothelial cells than cell culture adapted, highly-passaged avirulent laboratory strains such as Towne or AD169 (Brown et al. 1995; Waldman et al., 1991). This observation can be exploited to measure the "virulence" of a strain by assessing its growth characteristics in the SCID-hu mouse, in vivo in humans, or by other means. Recombinant vaccine candidates such as the ones described here which have deleted or incorporated DNA sequences are believed to replicate less well than the virulent parent in a suitable virulence assay. This observation would be indicative of an attenuated vaccine candidate. Deletion of the Toledo $U_L/b'$ region from the low passage, virulent HCMV Toledo genome results in a virus with reduced replicative ability in the SCID-hu mouse. This recombinant virus should have a concomitantly reduced virulence which allows administration of the virus without causing the undesired clinical manifestations exhibited by the Toledo virus in humans.

The invention identifies, maps, and sequences differences between the virulent Toledo strain and the avirulent highly passaged Towne strain, for the purpose of transferring novel genetic information to Towne to restore its immunogenicity or, alternatively, to remove information from Toledo to render it safe as a vaccine candidate. One major region of difference mapped to the internal portion of the L component. This large 13 kbp region present in Toledo but not highly passaged Towne is located at the border between the unique long (UL) and the inverted repeats bordering the UL region termed IRL or b'. We have deduced the coding information resident in the Toledo sequences and have extensively compared the information resident in AD169, highly passaged Towne and Toledo. We have made recombinant viruses which have either inserted the $U_L/b'$ region from the virulent Toledo strain, into the corresponding region of Towne, and have also deleted this region from Toledo and replaced it with a selectable marker and reporter gene or with the corresponding $U_L/b'$ region from Towne. Deletion of the virulence genes from Toledo decreased the ability of the recombinant to replicate within the SCID-hu (thy/liv) mouse, a model for CMV virulence. The new recombinant viruses exhibit growth properties in the SCID-hu mouse that indicate that vaccine candidates with attenuated virulence can be generated by deleting the $U_L/b'$ region from the Toledo virus. We have also demonstrated that we can add the Toledo region to the Towne virus which will presumably result in increased immunogenicity for the highly passaged Towne virus while retaining its safe profile for humans.

FIGS. 1A-1R show the nucleotide sequence of Toledo genome region isolated from Toledo strain of HCMV (SEQ ID NO. 1). FIGS. 2A-2H show the deduced amino acid sequences of open reading frames UL130, and UL132 through UL151 (SEQ ID NOS 2-22, respectively).

A basis of the present invention is the surprising and unexpected finding that: (1) clinical isolates of pathogenic CMV variants contain a genomic region which typically is not present in CMV strains which have undergone extensive laboratory passaging of the virus in cell culture, and (2) functional disruption (e.g., deletion or insertional inactivation and the like) of genes in this genomic region produces a substantial attenuation of CMV virulence and pathogenicity in vivo. The genomic region is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates and non-isolated pathogenic CMV variants which have a genomic region of at least 500 bp having at least 80 percent sequence identity to the Toledo genomic region of the Toledo strain having the sequences disclosed herein and in WO96/30387, incorporated herein by reference. The Toledo genomic region which is present in pathogenic CMV isolates and which is typically substantially absent in laboratory passaged CMV strains (e.g., AD169, Towne) has been sequenced and several open-reading frames have been identified. Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants. The invention is, in part, further based on the heretofore unrecognized finding that pathogenic clinical isolates of CMV have a distinct genome as compared to the commonly used laboratory-passaged strains of human CMV (e.g., AD169, Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which lack the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a genomic region of a CMV genome having substantial identity to at least 300 bp, typically at least 500 bp, of an approximately 15 kb sequence present in the genome of the Toledo strain of CMV and absent from the genome of the AD169 strain of CMV. In an aspect, the method functionally inactivates at least one open reading frame present in a genomic region of a CMV genome having substantial identity to at least 300 bp of a 13 kb sequence present in the genome of the Toledo strain of CMV and absent from the genome of the highly-passaged Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO: 1). In an embodiment, the method functionally inactivates at least the open reading frame corresponding to UL 148 as identified herein. In a variation, the method functionally inactivates open reading frames in the region spanning UL138 to UL 148. In an embodiment, the method functionally inactivates UL138, UL139, UL140, UL141, UL142, UL143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Inactivation is typically accomplished by genetic engineering and involves predetermined mutations (which may include additions, transpositions, or deletions), generally of the specific type which are not known to occur naturally in CMV strains even after extensive passaging.

In an aspect, the method of attenuating virulence comprises functional inactivation of open reading frames by structural mutation (e.g., deletion, insertion, missense or nonsense mutation, and the like) of at least one open reading frame, or a mutation of a transcriptional control sequence that controls transcription of the open reading frame, or mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by predetermined mutation, often produced by site-directed mutagenesis or in vitro recombination; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by predetermined mutation; in one embodiment the structural disruption results from deletion of the UL138-UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted by predetermined mutation. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AD169. The highly-passaged Towne genome comprises a region not present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame in inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 (EMBL accession number X17403) nucleotide numbering convention, operably linked to (2) Towne DNA (DNA substantially identical to a Towne strain, preferably identical to it) from about nucleotides 143,824 to 189,466 according to the AD169 (EMBL accession number X17403) nucleotide numbering convention, operably linked to (3) Toledo DNA (DNA substantially identical to a Toledo strain, preferably identical to it) from about nucleotides 189,466 to about 209, 514 corresponding to (i.e., according to) the AD169 (EMBL accession number X17403) nucleotide numbering convention, operably linked to (4) Towne DNA (DNA substantially identical to a Towne strain, preferably identical to it) from about nucleotides 200,080 to 229,354 according to the AD169 (EMBL accession number X17403) nucleotide numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ M.$^{-1}$, typically at least about $1 \times 10^8$ M.$^{-1}$, frequently at least $1 \times 10^9$ M.$^{-1}$ to $1 \times 10^{10}$ M.$^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a Towne genome and at least one open reading frame of a Toledo genome region, typically present in or adjacent to the $U_L/b'$ region of the composite CMV. In an aspect, the composite CMV is a Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucleotide probe, and the like. Detection of polypeptide speceis is typically done by immunoassay using a specific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

EXPERIMENTAL EXAMPLES

Overview

The growth advantage of Toledo in the SCID-hu mouse model resides in the genetic information encoded by the additional sequences (Toledo genomic region) we have identified. One gene in particular, UL148, has been mutagenized in Toledo by insertion of a selectable marker (gptILacZ) and the Toledo-based recombinant has been shown to replicate less well than Toledo in the SCID-hu assay. The genetic information of the corresponding region of the avirulent Towne virus has been deduced by nucleotide sequence analysis and demonstrated to lack an open reading frame in Towne. UL148 can be considered to be representative of a "virulence determinant" for Toledo. The new Toledo sequence identified at the inverted repeats has been analyzed to reveal novel genes in Toledo. Deletion of genes encompassing UL138 to UL148 in recombinant viruses have been tested for growth properties in the SCID-hu (thy/liv) mouse. These recombinants have been shown to replicate to levels similar to the Towne virus and represent attenuated vaccine candidates, since Towne has been shown to be safe and avirulent in humans. Such recombinants should show increased immunogenicity owing to their greater similarity to low passage virulent strains over that shown by highly-passaged Towne in humans. In addition, these strains should not exhibit the fully virulent phenotype shown by unmodified Toledo in humans due to the alterations we have introduced into their genomes.

This invention describes new recombinant HCMV viruses not previously described which are attenuated in virulence relative to low passage, virulent isolates by virtue of deletion of sequences shown to be present in low passage, virulent isolates but which are lacking in laboratory strains. The identification of these sequences was essential in order to prepare transfer vectors capable of shuttling deletions (or insertions such as selectable markers) resulting in an effective removal of coding information. Knowledge of the ORF usage on these DNAs permits deletion or insertion of one DNA into the other to specifically disrupt existing coding information. In addition, this invention identifies sequences which can be used as "spacer" DNA for substitution into deleted regions of HCMV clinical isolates for purposes of attenuation.

Cosmid Subclones of Towne and Toledo

Cosmid subclones of the CMV(Towne) and CMV(Toledo) genomes were constructed according to the method of Kemble et al. (1996) *J. Virol.* 70:2044, incorporated herein by reference. Human foreskin fibroblast (HF) cells were infected with either Towne or Toledo and following the development of extensive CPE, DNA was isolated from nucleocapsids by a procedure similar to that used for the preparation of HSV nucleocapsids (Denniston et al. (1981) *Gene* 15:365, incorporated herein by reference). The DNA was partially digested with Sau3AI, fractionated by agarose gel electrophoresis, and ligated to the BamHI site of BamHI, XbaI digested arms of the SuperCos•A1 cosmid vector. SuperCos•A1 was derived from SuperCos-1 (Stratagene, San Diego, Calif.) by the insertion of an oligonucleotide incorporating SrfI and PacI recognition sequences flanking a unique BamHI site. The position of the cosmid subclones relative to the viral genome was identified by Southern and DNA sequence analyses.

Overlapping Cosmids for Virus Regeneration

Mapping the extent of the viral insert within the cosmid subclones was used as a basis to form specific Towne/Toledo chimeric viruses by choosing the appropriate cosmids from each virus. The ends of adjacent cosmids should overlap (~200 bp or more) such that homologous recombination is permitted in eucaryotic cells.

Figure 5:
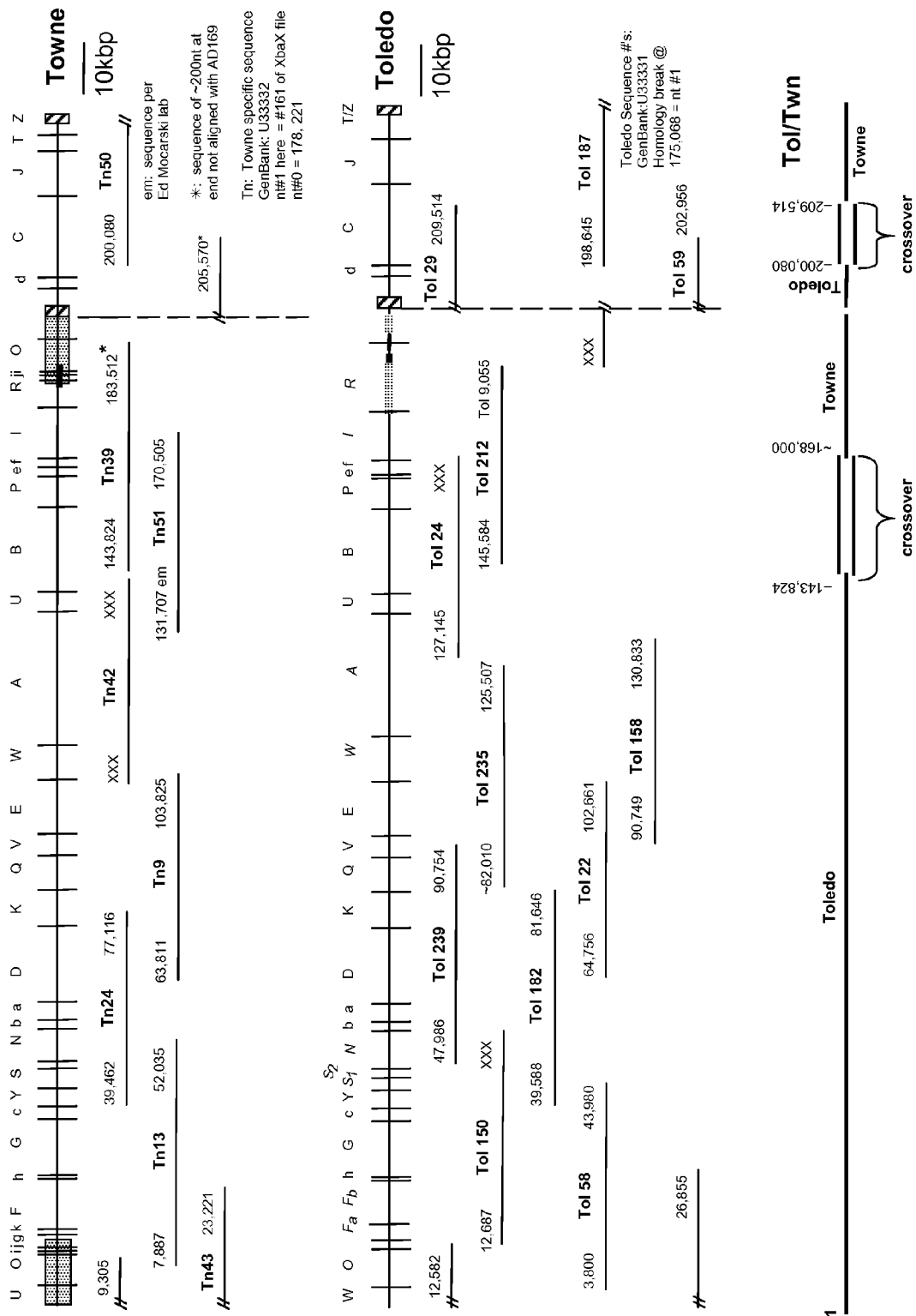
FIG. 5. CMV Towne and Toledo cosmids used to regenerate specific chimeric CMV viruses. The location of the cosmid insert are indicated beneath the appropriate viral genome. The numbers at the end of the insert denote the endpoints determined by DNA sequence analysis; the numbers correspond to AD169 genomic sequence in GenBank (EMBL accession number X17403). "XXX" "denotes an end which was refractory to DNA sequence analysis. These ends were mapped by restriction enzyme and Southern blot analyses. The vertical dashed line represents the location of the internal "a" sequence of the virus. The lower line depicts the structure of the Tol/Twn 39/50 genome. The thick gray line denotes sequences derived from Toledo and the thin black line depicts sequences contributed from highly-passaged Towne strain. Regions of overlap could be derived from either virus and are repregented by a region of a thick gray and a thin black line together. The Tol/Twn 39/50 genome does not contain the Toledo genomic region.

To construct a Toledo based virus which lacked the Toledo $U_L/b'$ region and in its place contained the Towne $U_L/b'$ region, the following set of cosmids was used: Tol29, Tol58, Tol182, Tol22, Tol158, Tol124, Tn39, and Tn50. The resulting virus was designated Tol/Twn 39/50 (see FIG. 5). Other viruses were regenerated by cosmid cotransfection which lacked portions of the Toledo $U_L/b'$ region. Toledo based viruses were generated by the cotransfection of the Toledo cosmids, Tol29, Tol58, Tol182, Tol22, Tol158, Tol24, Tol 212, Tol187 OR To159, Tol150, Tol239, Tol235, Tol158, Tol24, Tol212, Tol187. Towne/Toledo chimeras lacking portions of the Toledo $U_L/b'$ region were regenerated by cotransfection of Tn43, Tn13, Tn24, Tn9, Tn42, Tn51, Tol212, Tol187. Because Tol 212 and Tol187 did not overlap, deletions resulted in the viruses regenerated from these cosmid sets which lacked varying portions of the Toledo $U_L/b'$ region.

Preparation of Cosmids for Cotransfection

A set of overlapping cosmid clones constituting the appropriate viral genome were individually digested with PacI to release the intact viral insert from the cosmid vector. The restriction enzyme was inactivated by heating at 65° C. for 20 minutes, the cosmids were combined and the DNA precipitated with ethanol. A $CaPO_4$ precipitate was formed from approximately 8 to 16 µg of this mixture and transfected using general transfection methods. The DNA was transfected into approximately $1 \times 10^6$ low passage (<15 passes) HF, LF (human embryonic lung fibroblast) or IFIE1.3 (a gift of Ed Mocarski; these cells are immortalized HF cells that express the CMV major immediate early protein) cells. All these cells are permissive for CMV replication.

For HF and LF cells, approximately $1 \times 10^6$ cells were plated onto a 25 cm$^2$ flask 3 to 5 hours prior to the addition of the DNA-$CaPO_4$ precipitate. At this point, the precipitate was adsorbed directly to the cell monolayer for 30 minutes prior to the addition of media. 2 ml of media was added and incubation continued for 4 hours at 37° C.

For IFIE1.3 cells, the cells were trypsinized approximately 16 hours prior to the addition of the DNA-$CaPO_4$ precipitate and seeded at a 1:2 density. At the appropriate time post seeding, the DNA-$CaPO_4$ precipitate was added in addition to 2 ml of media and incubated at 37° C. for 4 hours.

Following the 4 hour incubation, the DNA-CaPO.sub.4 precipitate was removed, the cells incubated at 37° C. for 3 min in 15% glycerol in Hepes buffered saline, rinsed one time with media and fed with 5 ml of media. The media on the cells was changed every 3 to 4 days and plaques appeared in 10 to 21 days.

Construction of Recombinant CMV by Insertion of a gpt/LacZ Marker

Figure 4:
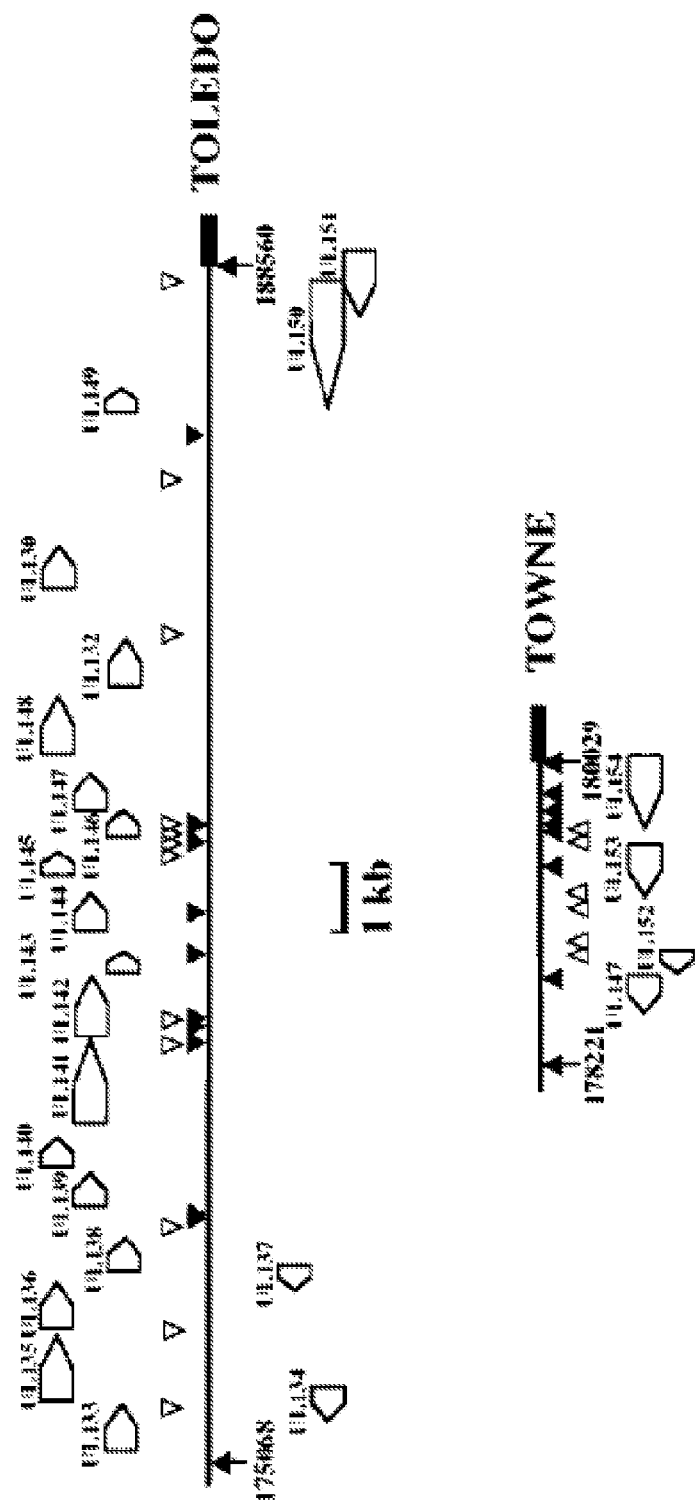
FIG. 4. Schematic comparison of the novel genome regions of Toledo and highly-passaged Towne as compared to AD169.

Two plasmids encompassing the Toledo $U_L/b'$ region and derivatives thereof were constructed which contained a marker gene. A segment of DNA encompassing AD169 bases 156251 174483 was removed from pON2601 (Cha et al. (1996) J. Virol. 70:78, incorporated herein by reference) and a PacI linker was introduced at AD169 base 174484 to yield a subclone of pON2601. FIGS. 3 and 4 show a schematic drawing of the open reading frames in the Toledo $U_L/b'$ region using sequence numbering from the Toledo $U_L/b'$ region DNA insert. A 4.8 kb DNA fragment containing the *E. coli* gpt and lacZ genes driven by the HSV thymindine kinase and β actin promoters (Prichard et al. (1996) *J. Virol.* 70:3018, incorporated herein by reference), respectively, was then inserted into the NsiI site in Toledo UL148 within the pON2601 subclone. The resulting plasmid containing the gpt and lacZ insert in UL148 was designated pGD6. Toledo open reading frames UL138 to UL148 were removed from pGD6 by a BamHI collapse to produce the plasmid pGD7. Toledo recombinant viruses Tol pGD6 and Tol pGD7 were constructed using plasmids pGD6 and pGD7, respectively, as described (Prichard et al. (1996) op.cit.).

Analysis of Recombinant CMV in SCID-hu (thy/liv) Mice

SCID-hu (thy/liv) mice were derived by implanting human fetal thymus and liver beneath the kidney capsule of a female C.B.-17 scid/scid IcrTac mouse (McCune et al. (1988) *Science* 241:1632, incorporated herein by reference). The SCID-hu (thy/liv) mouse model serves as an animal model that can distinguish virulent from avirulent strains of CMV based on their replication levels within the human implant (Mocarski et al. (1993) *Proc. Natl. Acad. Sci. (U.S.A.)* 90:104 and Brown et al. (1995) *J. Infect. Dis.* 171:1599, each incorporated herein by reference). Several weeks following implantation, the human implant on the murine kidney was surgically exposed and an inoculum of $10^4$ PFU of the appropriate virus was injected directly into the human tissue in a volume of 10-25 µl. The murine kidney/human implant was placed back into the animal in its natural position and the animal was recovered. 2 weeks following infection of the human tissue, the animal was sacrificed and the implant was removed and added to 2 ml of 4.5% skim milk/50% media.

The excised implant was homogenized with an automated Dounce apparatus (Glas-Col, Terre Haute, Ind.) and the suspension was stored at −80° C. until the titers were determined. The suspension was thawed at 37° C., sonicated on ice by three cycles of 10 sec on/10 sec off and centrifuged to remove the debris. The supernatent was recovered and the titer of CMV present was determined on confluent monolayers of HF cells. 7 to 10 days after plating the virus, the monolayers were fixed and stained with Giemsa and plaques enumerated.

Figure 6:
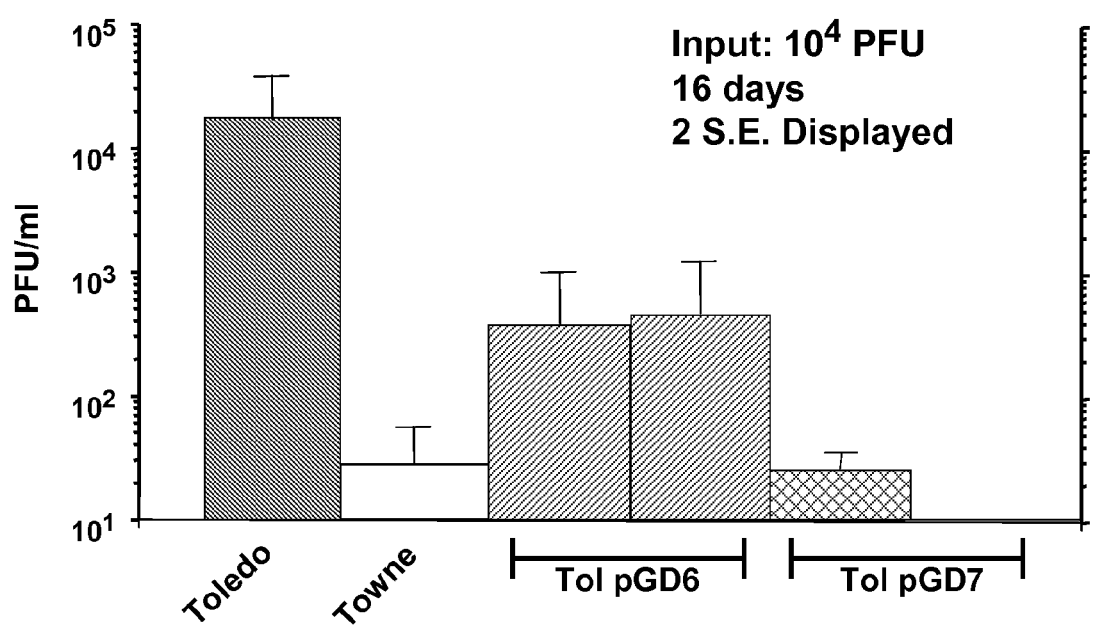
FIG. 6. Analysis of the gpt/LacZ recombinant viruses in the SCID-hu (thy/liv) model. Two independent isolates of Tol pGD6 and Tol pGD7 were tested in the model. 3 mice were used per group and the mean of the data is displayed. Error bars representing 2 standard errors from the mean are also displayed.
Figure 7:
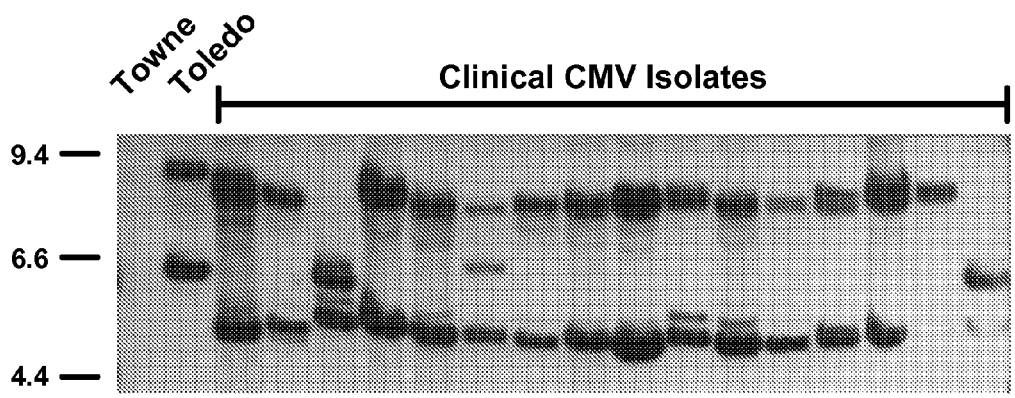
FIG. 7. Southern blot showing that a variety of clinical isolates of CMV contain sequences homologous to the Toledo $U_L$/b' region. The Towne lane contains genomic DNA from Aviron's highly-passaged Towne strain (Towne AV).
Figure 10:
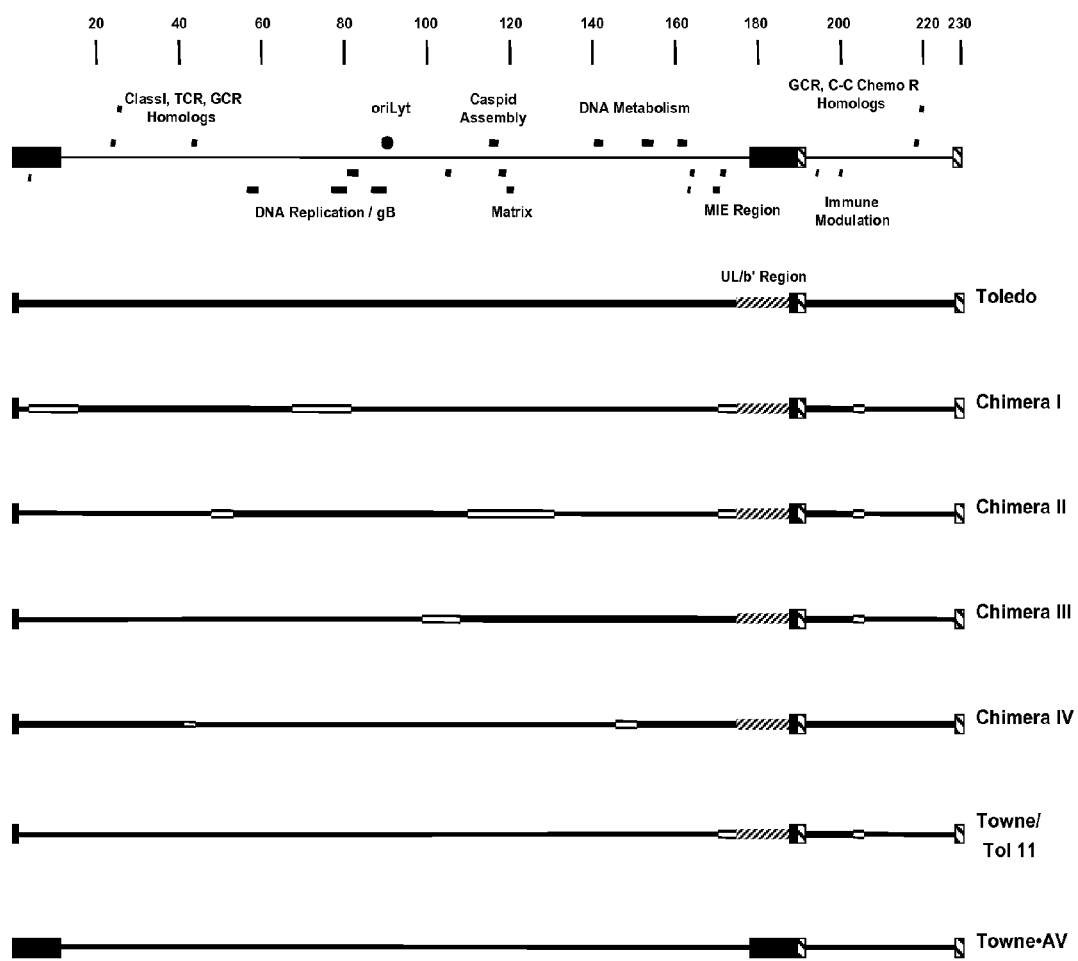
FIG. 10. Schematic depiction of the specific exemplary embodiments denoted Chimera I, Chimera II, Chimera III, Chimera IV, and Towne/Tol 11. Toledo genome is depicted as "Toledo"; highly-passaged Towne genome is depicted as "Towne•AV"; selected reading frames of importance, proposed function/homologues of selected ORFs, and scale (in kbp) is shown on the top line.

FIG. 6 shows results from this experiment. The virulence of the Toledo strain CMV is attenuated by functional disruption of Toledo genome region open reading frames.

The difference in virulence between the Towne and Toledo strains appears to have resulted from genetic differences generated during the adaptation of Towne to growth in dipoid fibroblasts in culture. Both Towne and Toledo were originally isolated from the urine of a congenitally infected infant. Towne was subsequently passaged over 125 times in culture resulting in genetic alterations in the viral genome and an avirulent virus. The virulent Toledo virus, in contrast, was passaged approximately 5 times in diploid fibroblasts in order to produce material that could cause disease in humans.

Figure 11:
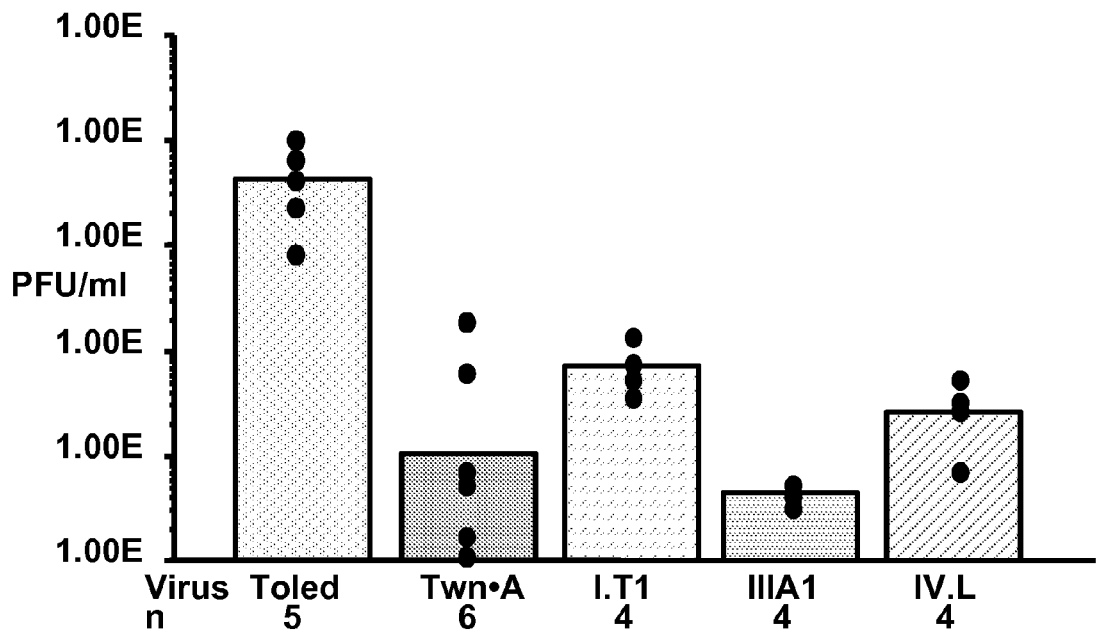
FIG. 11. Replication of Toledo, highly passaged Towne, and Chimeras I, III, and IV (in order, respectively) in SCID-hu mice having a thymus/liver implant.
Figure 12:
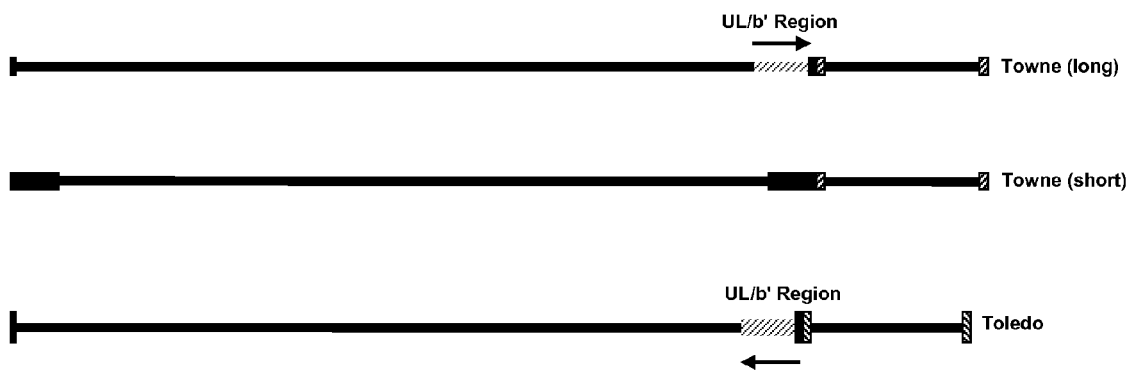
FIG. 12. Schematic comparison of low-passage (long) Towne genome and high-passage (short) Towne genome.

These linked genetic and biological differences can be used to create a live, attenuated HCMV vaccine. The rationale for tissue culture adaptation of Towne was to generate a live, attenuated vaccine strain. Towne has been shown to be safe and somewhat immunogenic. Towne, however, is overattenuated. The immune response induced by inoculation with Towne does not protect against subsequent HCMV infection as effectively as that generated by natural infection. Vaccine candidates can be generated by replacing genetic elements of the overattenuated Towne strain with homologous portions of the virulent Toledo strain. Through the analysis of these "chimeric" viruses, a skilled artisan can select those that have the level of desirable characteristics of Towne and be attenuated to a more efficacious degree.

Our first four chimeric viruses, as a set, will contain the entire Toledo genome introduced into the Towne genetic background. Each individual chimera of the set will contain approximately 40 55% of the Toledo genome; the remainder will be derived from Towne. Each of these chimeras will contain the $U_L$/b' region derived from Toledo. Genes within this region of the Toledo genome can affect cell tropism of HCMV. The viruses, designated chimera I, II, III, and IV were constructed from the cosmids listed in Table 1 (see also FIGS. 9 and 10).

TABLE 1

Cosmids used to generate specific chimeras.

| Viruses | | | |
|---|---|---|---|
| I | II | III | IV |
| Tn46a | Tn46 | Tn46 | Tol29 |
| Tol58b | Tn45 | Tn45 | Tol58 |
| Tol182 | Tol239 | Tn23 | Tn23 |
| Tn47 | Tol22 | Tn47 | Tn47 |
| Tn44 | Tol158 | Tol184 | Tn44 |
| Tn26 | Tn26 | Tol24 | Tn26 |
| Tn20 | Tn20 | Tol212 | Tol212 |
| Tol11 | Tol11 | Tol11 | Tol122 |

Large quantities of each cosmid were prepared by purification of the *E. coli* produced material over a Qiagen column as described by the manufacturer. 10 micrograms of each cosmid was digested with the restriction enzyme Pac I (New England Biolabs) to physically separate cosmid vector from viral sequences. Following digestion, the enzyme was inactivated by incubation at 65° C. for 20 minutes and the appropriate cosmids were combined, precipitated with ethanol in the presence of 0.3M sodium acetate, rinsed in 70% ethanol, and air-dried briefly. The resulting DNA was solubilized in approximately 100 microliters of 10 mM Tris pH 7.5/1 mM EDTA. Various amounts of the cosmid mix was transfected by the calcium phosphate technique into permissive fibroblast cells, specifically human lung fibroblasts (LF, prepared in our laboratory), human neonatal foreskin fibroblast (HF, a gift of Dr. Ed Mocarski, Stanford University), MRC-5 (ATCC) or IFIE1.3 cells (a gift of Ed Mocarski, Stanford University). The IFIE1.3 cell line constitutively expresses the HCMV ie 1 gene product and has been transformed with the human papilloma virus E6 and E7 genes transduced by a retrovirus vector. 3 to 5 hours after transfection the cells were shocked by incubation in 15% glycerol/Hepes buffered saline for 3 minutes at 37° C. and fed with DME/10% fetal bovine serum. 7 to 10 days after transfection plaques with distinct HCMV CPE were evident.

Plaques derived from the chimeras were allowed to grow until 100% of the monolayer exhibited CPE. At this point, DNA was extracted from the supernatent and cellular fractions and analyzed by restriction enzyme digestion. The structures of the viruses can be deduced by the cosmids used for construction of the chimera and confirmed by comparing the EcoRI digestion pattern to the maps derived for Towne and Toledo (see FIG. 10). Table 2 describes the composition of each of the chimeras, the nucleotide limits are derived from sequence analysis of the end of each cosmid insert and its homology to the AD169 strain of HCMV, which has been sequenced in its entirety (EMBL accession number X17403). All of the chimeras had restriction enzyme patterns consistent with the proposed structures.

TABLE 2

Genetic composition of the chimeras.

| Chimera | Towne DNA | Toledo DNA | Crossover Region |
|---|---|---|---|
| I | 1-3799 | 15750-67568 | 3800-15749 (SEQ ID NO.: 23)) |
| | 81647-170499 | 175069-203136 | 67569-81646 (SEQ ID NO.: 24) |
| | 205803 to S term. | | 170500-175068 (SEQ ID NO.: 25) |
| II | 1-47985 | 53244-~110000 | 47986-53243 (SEQ ID NO.: 27) |
| | 138834-170499 | 175069-203136 | ~110000-130833 (SEQ ID NO.: 28) |
| | 205803 to S term. | | 170500-175068 (SEQ ID NO.: 25) |
| III | 1-~99000* | 108094-203136 | ~99000-108093 (SEQ ID NO.: 29) |
| | 205803 to S term. | | 203137-205802 (SEQ ID NO.: 26) |
| IV | 43981-145583 | 1-41356 | 41357-43980 (SEQ ID NO.: 30) |
| | | 150754-S term | 145584-150753 (SEQ ID NO.: 31) |

*Sequence at end of cosmid was undefinable. Nucleotide number is not exact crossover region is the region of cosmid overlap. The contribution of each virus to this region has yet to be defined.

Two other chimeras are constructed based on an observation derived from the sequence analysis of several different members of the beta-herpesvirus family including HCMV, human herpesvirus 6 (the causative agent of roseola) and murine cytomegalovirus. Representative members of each of these viruses have been sequenced in their entirety and a "core" set of genes corresponding to HCMV UL23 to UL122 are conserved among these evolutionarily divergent entities (Chee, et al. 1990; Gompels, et al. 1995; Rawlinson, et al. 1996, incorporated herein by reference). These core genes contribute to DNA replication, virion structure, and other basic features of the virus. Genes outside this core region are involved in virus-host and virus-immune system interaction and may determine specific properties of virus biology. Replication of the Chimeras was tested in SCID-hu mice having a thy/liv sandwich under the kidney capsule; representative data is shown in FIG. 11.

Two additional chimeras are constructed: one which has the core derived from Toledo with the remainder of the genes derived from Towne and an inverse construct in which the core is derived from Towne and the remainder of the genes are from Toledo. These viruses are constructed through the use of overlapping cosmids and derivatives of the cosmids. Table 3 outlines the constructs that can be used to generate these two chimeric viruses.

TABLE 3

Construction of chimeras containing conserved core regions.

| Towne Core/Tol Noncore | Tol Core/Towne Noncore |
|---|---|
| Tol29 | Tn43 |
| Tol58 nts: 3800-27862 | Tn45 nts: 7854-27862 |
| Tn45 nts: 27500-53243 | Tol58: 27500-43980 |
| Tn23 | Tol182 |
| Tn47 | Tol22 |
| Tn44 | Tol158 |
| Tn26 | Tol24 |
| Tn20 | Tol212 nts: 145584-17200 |
| Tol11 nts: 170852-188890 | Tn39 nts: 170852-183512 |
| Tol122 | Tn15 |

All of these viruses are used to inoculate healthy adult human volunteers. These individuals are assessed for symptoms of HCMV disease, including fever, malaise, and abnormal liver enzyme levels. Hallmarks of viral infection are also assessed by measuring HCMV specific antibody titers before and after inoculation as well as viral culture for the isolation of infectious virus from bodily fluids. A successful vaccine candidate is identified as a strain that maintains the safety profile of Towne while stimulating a greater immune response to the virus.

FIG. 12 shows schematic depiction of the Toledo genome in comparison with highly passaged Towne (short genome) and low-passage Towne (long genome).

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

The invention claimed is:

1. A chimeric cytomegalovirus (CMV) virus which comprises: (a) the polynucleotide sequence of a Toledo genome from nucleotides 1 to 41356; (b) the polynucleotide sequence of a high-passage Towne genome from nucleotides 43981 to 145583; (c) the polynucleotide sequence of a Toledo genome from nucleotides 150754 to S-term, wherein the high-passage Towne genome has been passaged at least 50 times and wherein the nucleotide number of the Towne and Toledo genomes is according to the numbering convention of the AD169 genome.

2. A chimeric CMV virus which comprises: (a) the polynucleotide sequence of a of a Toledo genome from nucleotides 1 to 41356; (b) a crossover region comprising SEQ ID NO.: 30; (c) the polynucleotide sequence of a high passage Towne genome from nucleotides 43981 to 145583; (d) a crossover region comprising SEQ ID NO.: 31; (e) the polynucleotide sequence of a Toledo genome from nucleotides 150754 to S-term, wherein the high-passage Towne genome has been passaged at least 50 times and wherein the nucleotide number of the Towne and Toledo genomes is according to the numbering convention of the AD 169 genome.

3. An immunogenic composition comprising the chimeric virus of claim 1.

4. An immunogenic composition comprising the chimeric virus of claim 2.

5. A method of inducing an immune response comprising administering to a human an immunological composition of claim 3, in an amount sufficient to stimulate an immune response in said human.

6. A method of inducing an immune response comprising administering to a human an immunological composition of claim 4 in an amount sufficient to stimulate an immune response in said human.

* * * * *